United States Patent
Khalil et al.

(10) Patent No.: US 11,746,104 B2
(45) Date of Patent: Sep. 5, 2023

(54) CHALCONE-BASED CHEMOTHERAPEUTIC COMPOUND FOR TRIPLE NEGATIVE BREAST CANCER

(71) Applicant: QATAR UNIVERSITY, Doha (QA)

(72) Inventors: Ashraf Khalil, Doha (QA); Ala-Eddin Al Moustafa, Doha (QA); Dana H. Elkhalifa, Doha (QA); Feras Alali, Doha (QA)

(73) Assignee: QATAR UNIVERSITY, Doha (QA)

( * ) Notice: Subject to any disclaimer, the term of this patent is extended or adjusted under 35 U.S.C. 154(b) by 0 days.

(21) Appl. No.: 16/440,861

(22) Filed: Jun. 13, 2019

(65) Prior Publication Data

US 2020/0392119 A1    Dec. 17, 2020

(51) Int. Cl.
| | |
|---|---|
| *A61K 31/03* | (2006.01) |
| *A61K 31/035* | (2006.01) |
| *C07C 225/22* | (2006.01) |
| *C07C 317/32* | (2006.01) |
| *C07D 405/10* | (2006.01) |
| *C07D 413/10* | (2006.01) |
| *C07D 295/033* | (2006.01) |
| *A61P 35/00* | (2006.01) |
| *C07C 317/30* | (2006.01) |
| *A61K 45/06* | (2006.01) |

(52) U.S. Cl.
CPC ............ *C07D 405/10* (2013.01); *A61P 35/00* (2018.01); *C07C 225/22* (2013.01); *C07C 317/30* (2013.01); *C07D 295/033* (2013.01); *C07D 413/10* (2013.01); *A61K 45/06* (2013.01)

(58) Field of Classification Search
CPC .... A61K 31/03; A61K 31/035; C07C 225/22; C07C 317/32; C07D 405/10; C07D 413/10; C07D 295/033; A61P 35/00
USPC ...... 514/748, 754, 235.8; 564/305; 568/334, 568/306
See application file for complete search history.

(56) References Cited

U.S. PATENT DOCUMENTS

| | | | |
|---|---|---|---|
| 4,904,697 | A | 2/1990 | Sunkara et al. |
| 7,112,698 | B2 | 9/2006 | Potter et al. |
| 7,563,789 | B2 | 7/2009 | Anderson et al. |
| 7,714,025 | B2 | 5/2010 | Rose et al. |
| 8,236,985 | B2 | 8/2012 | Aboagye et al. |
| 2002/0143064 | A1 | 10/2002 | Chiron et al. |
| 2005/0203170 | A1 | 9/2005 | Mailliet et al. |
| 2016/0166592 | A1 | 6/2016 | Bae et al. |

FOREIGN PATENT DOCUMENTS

WO    WO-2013025484 A1 *    2/2013    ......... A61K 31/4025

OTHER PUBLICATIONS

Janet Sabina, X., J. Karthikeyan, G. Velmurugan, M. Muthu Tamizh and A. Nityananda Shetty, "Design and in vitro biological evaluation of substituted chalcones synthesized from nitrogen mustards as potent microtubule targeted anticancer agents" New J. Chem., 2017, 41, pp. 4096-4109. (Year: 2017).*
English translation of the publication: Fang, X., L. Zhou, Z. Cheng, M. Yang and B. Yang, "Synthesis, Crystal Structures and Antitumor Activity of Novel Nitrogen Mustard-Linked Chalcones" Chin. J. Org. Chem. 2013, 33, pp. 523-529. (Year: 2013).*
Janet Sabina, X., J. Karthikeyan, G. Velmurugan, M. Muthu Tamizh and A. Nityananda Shetty, "Design and in vitro biological evaluation of substituted chalcones synthesized from nitrogen mustards as potent microtubule targeted anticancer agents" New J. Chem., 2017, 41, pp. 4096-4109. (Year: 2017).*
Polo, E., et al., "Ultrasound-assisted synthesis of novel chalcone, heterochalcone and bis-chalcone derivatives and the evaluation of their antioxidant properties and as acetylcholinesterase inhibitors", Bioorg. Chem. 90 (2019), 103034, pp. 1-11. (Year: 2019).*
Fang, X., L. Zhou, Z. Cheng, M. Yang and B. Yang, "Synthesis, Crystal Structures and Antitumor Activity of Novel Nitrogen Mustard-Linked Chalcones" Chin. J. Org. Chem. 2013, 33, pp. 523-529. (Year: 2013).*
English translation of the publication: Fang, X., L. Zhou, Z. Cheng, M. Yang and B. Yang, "Synthesis, Crystal Structures and Antitumor Activity of Novel Nitrogen Mustard-Linked Chalcones" Chin. J. Org. Chem. 2013, 33, pp. 523-529. (Year: 2020).*

(Continued)

*Primary Examiner* — Joseph R Kosack
*Assistant Examiner* — Sagar Patel
(74) *Attorney, Agent, or Firm* — SQUIRE PATTON BOGGS (US) LLP

(57) ABSTRACT

Provided herein are compounds, compositions, and methods useful for the treatment of breast cancer, particularly triple negative breast cancers. In certain aspects, provided herein are compounds of formula (I):

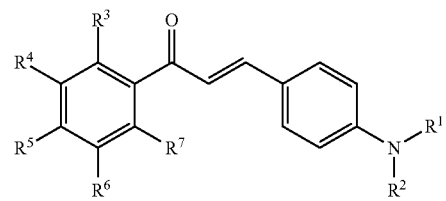

or a pharmaceutically acceptable salt or solvate thereof. In certain aspects, provided herein are compositions comprising any of the compounds provided herein. In certain aspects, provided herein are methods for the treatment of cancer in a subject in need thereof comprising administering to the subject an effective amount of any of the compounds or compositions provided herein.

12 Claims, 38 Drawing Sheets

(56) References Cited

OTHER PUBLICATIONS

Qiu et al., "Synthesis of dihydropyrazole sulphonamide derivatives that act as anti-cancer agents through COX-2 inhibition", Pharmacological Research (2016), 104: pp. 86-96. (Year: 2016).*
Bukhari et al., "Synthesis and biological studies of a novel series of4-(4-(1H-imidazol-1-yl)phenyl)-6-arylpyrimidin-2-amines", Med. Chem. Res. (2013), 22: pp. 5248-5254. (Year: 2013).*
STN Registry RN 1002183-74-5 (Entered date: Feb. 8, 2008) (Year: 2008).*
STN Registry RN 940853-37-2 (Entered date: Jul. 2, 2007) (Year: 2007).*
D. Elkhalifa et al., "Design, synthesis, and validation of novel nitrogen-based chalcone analogs against triple negative breast cancer", European Journal of Medicinal Chemistry 187 (2020) 111954, available online Dec. 7, 2019, journal homepage: http://www.elsevier.com/locate/ejmech; https://doi.org/10.1016/j.ejmech.2019.111954, 15 pages.
M. N. Gomes et al., "Chalcone Derivatives: Promising Starting Points for Drug Design", Molecules 2017, 22, 1210; doi:10.3390/molecules22081210, www.mdpi.com/journal/molecules, 25 pages.
Rizeq et al., "Novel Nitrogen-Based Chaicone Analogs Provoke Substantial Apoptosis in HER2-Positive Human Breast Cancer Cells via JNK and ERK1/ERK2 Signaling Pathways", International Journal of Molecular Sciences; Sep. 6, 2021; vol. 22, 9621; pp. 1-17. https://doi.org/10.3390/ijms22179621.

\* cited by examiner

Figure 2. Chalcones synthetic route

Figure 3.1a
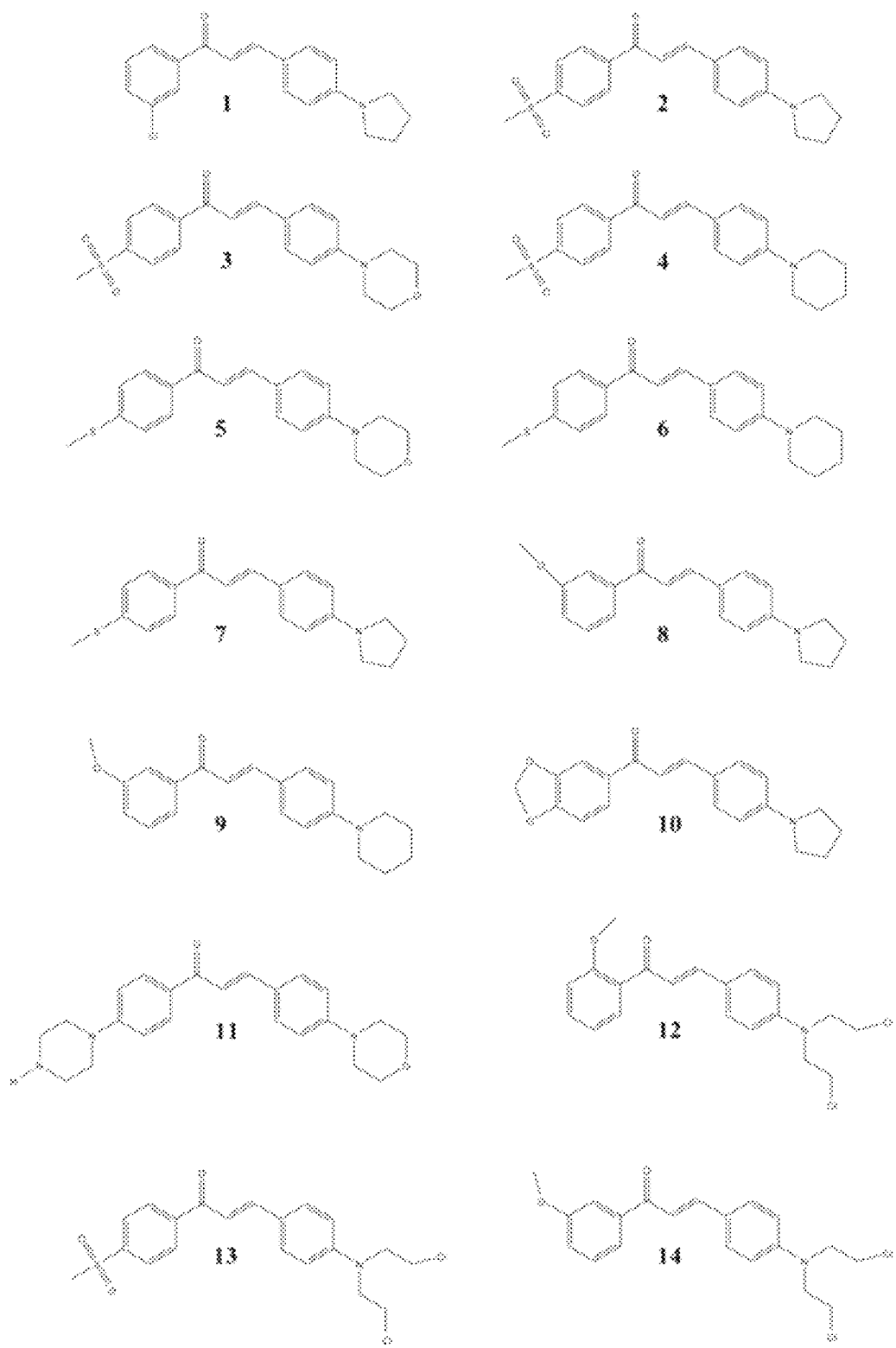
Figure 3.1a. Chemical structures of the synthesized chalcone analogs (1-14)

Figure 3.1b
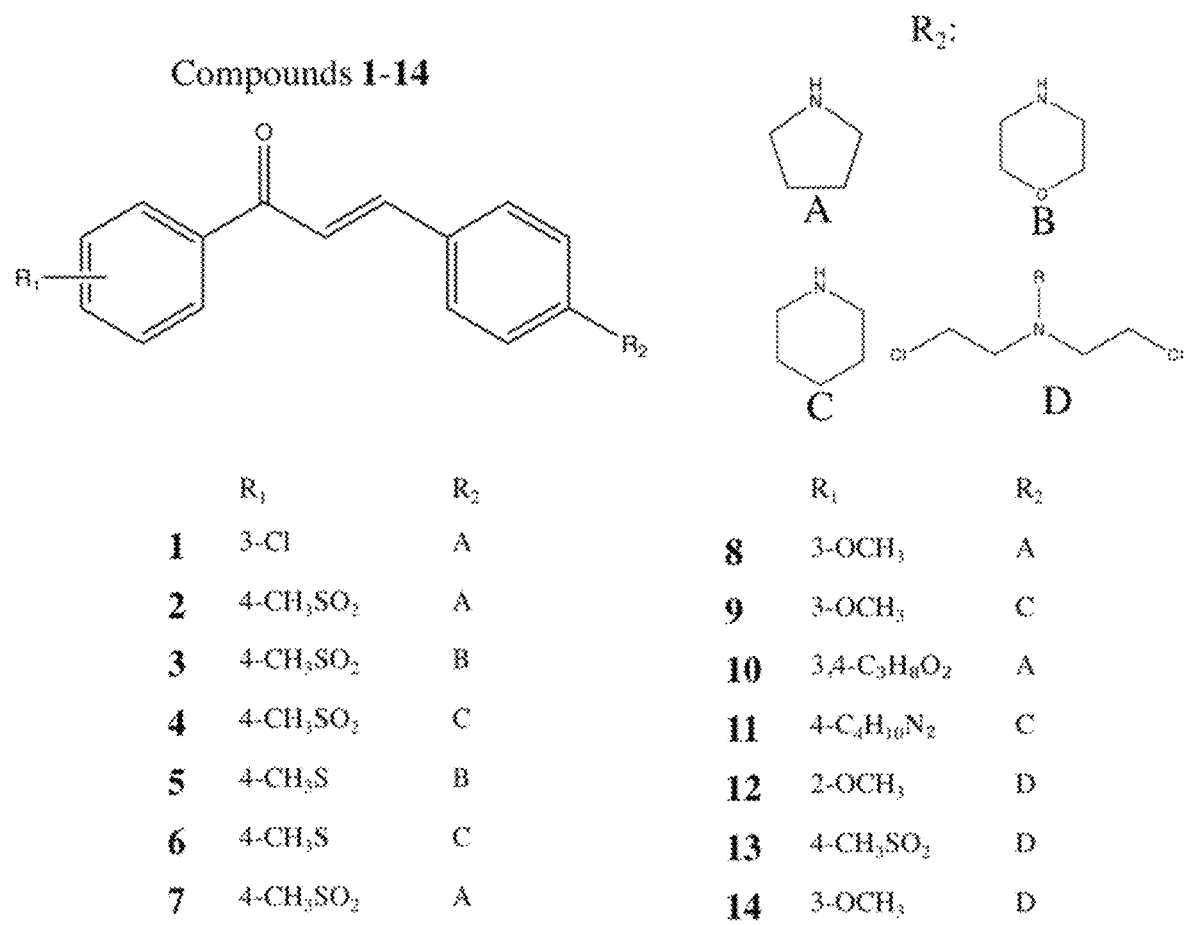
Figure 3.1b. Chemical structures of the synthesized chalcone analogs

Figure 3.2
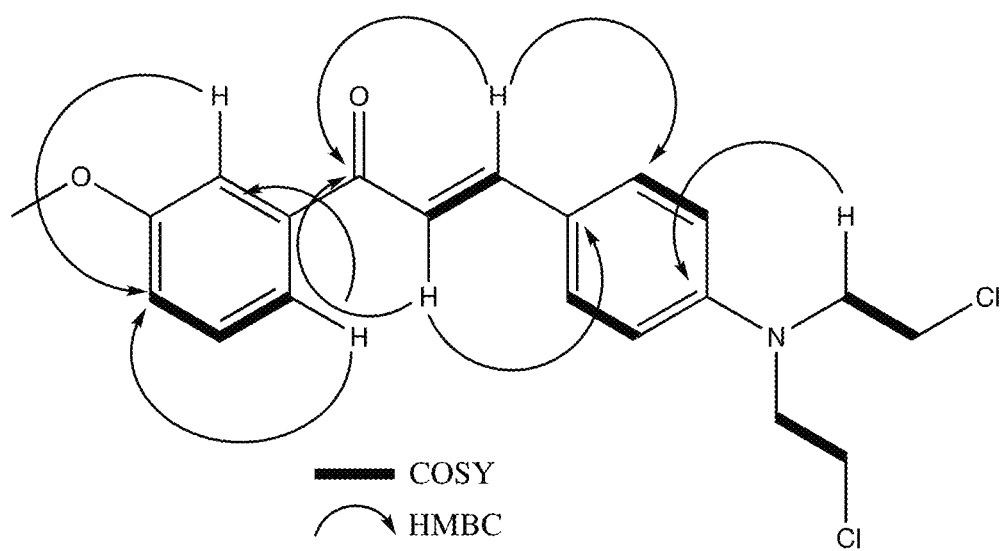
▬ COSY
⌒ HMBC

Figure 3.3
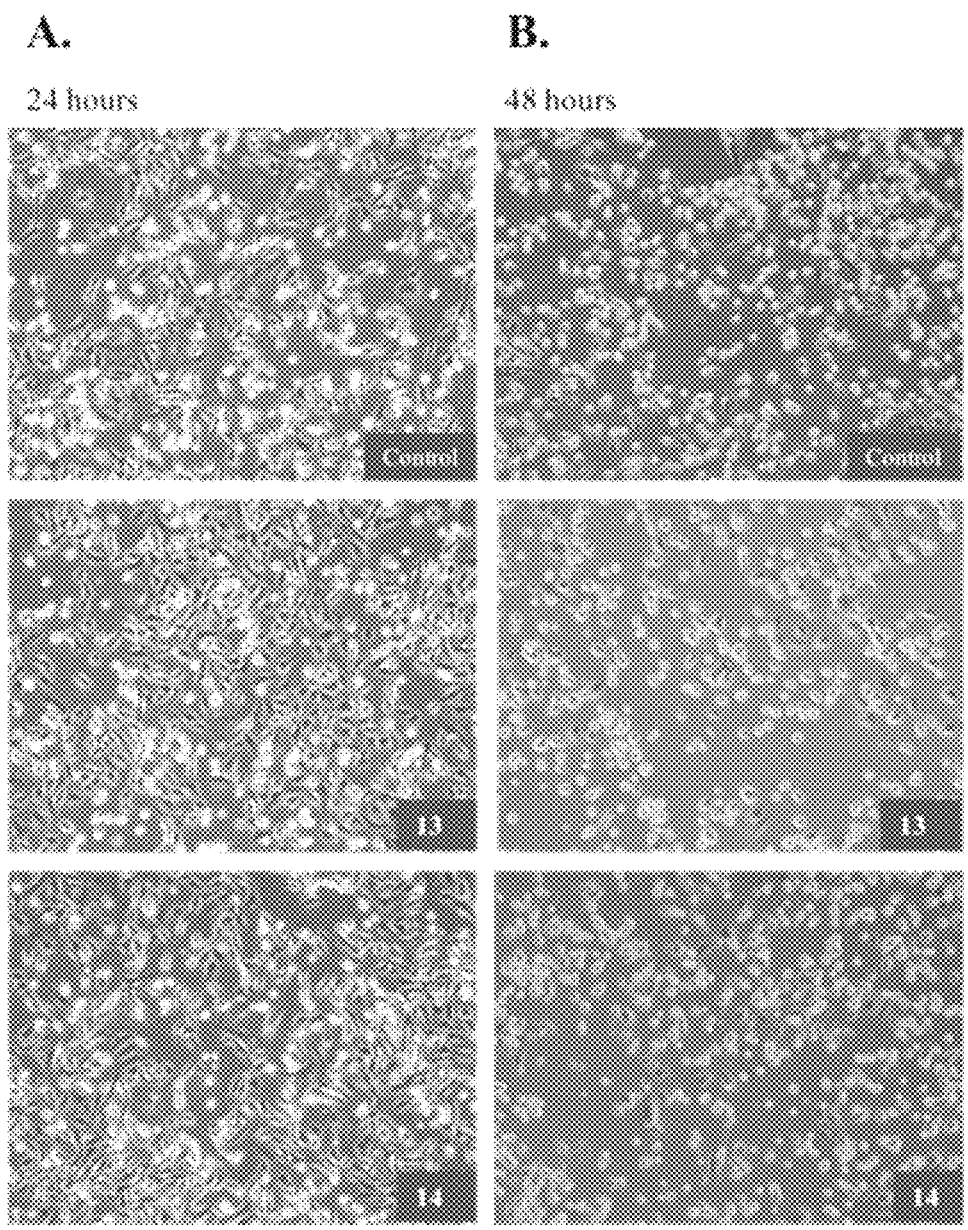

Figure 3.4
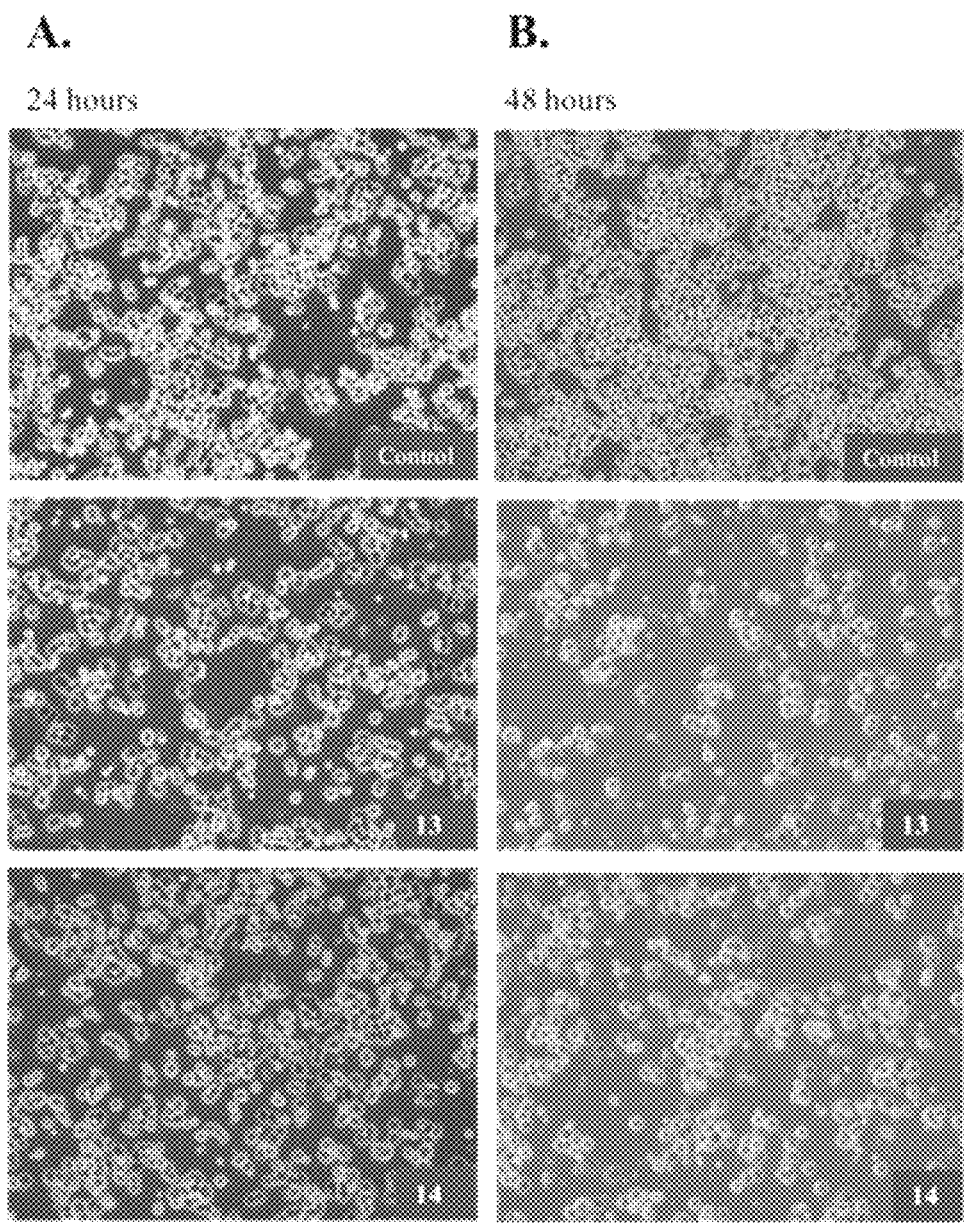

Figure 3.5
A.
24 hours
B.
48 hours
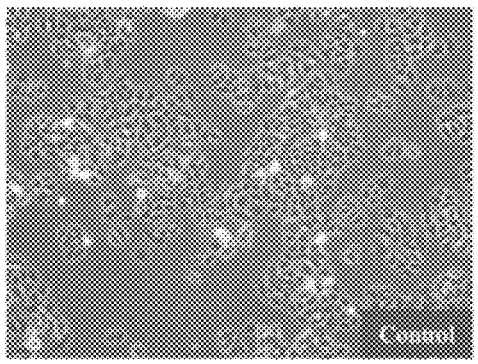
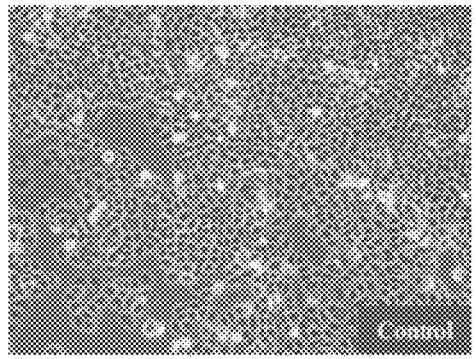
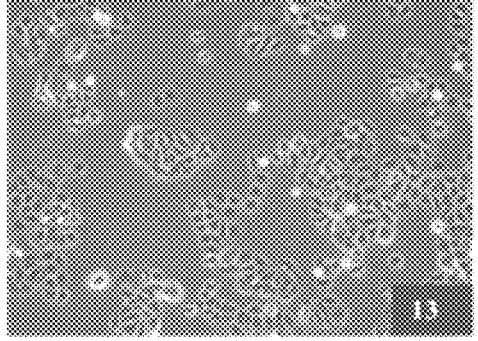
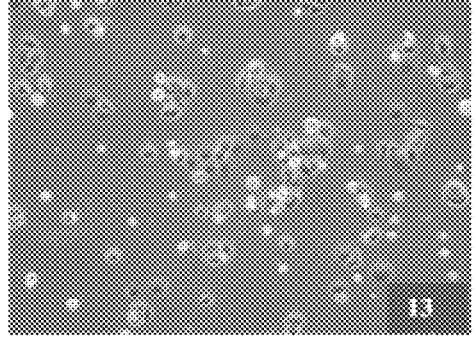
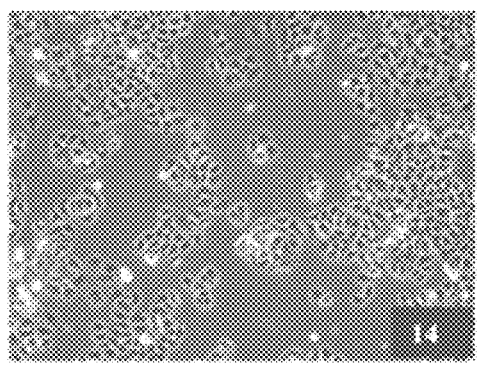
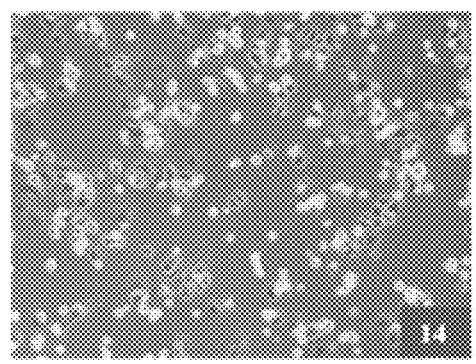

Figure 3.6
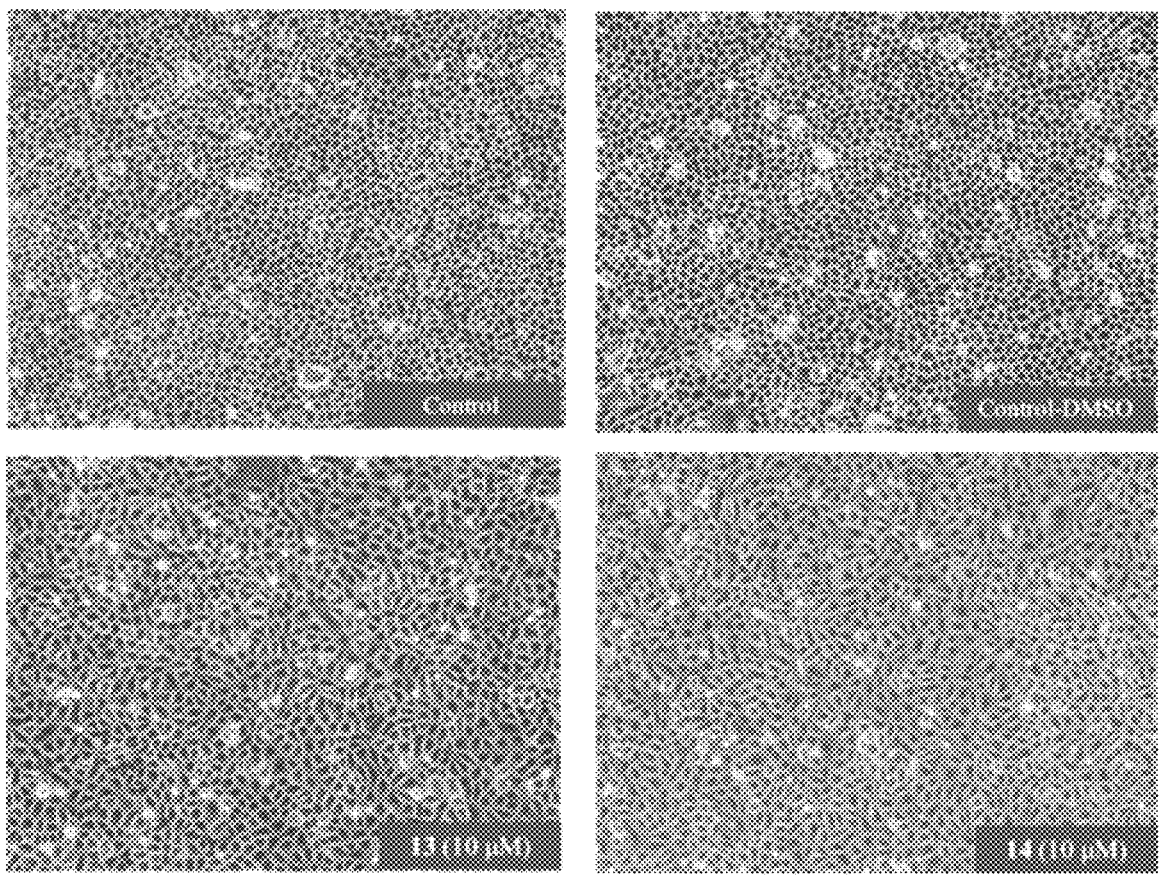

Figure 3.7
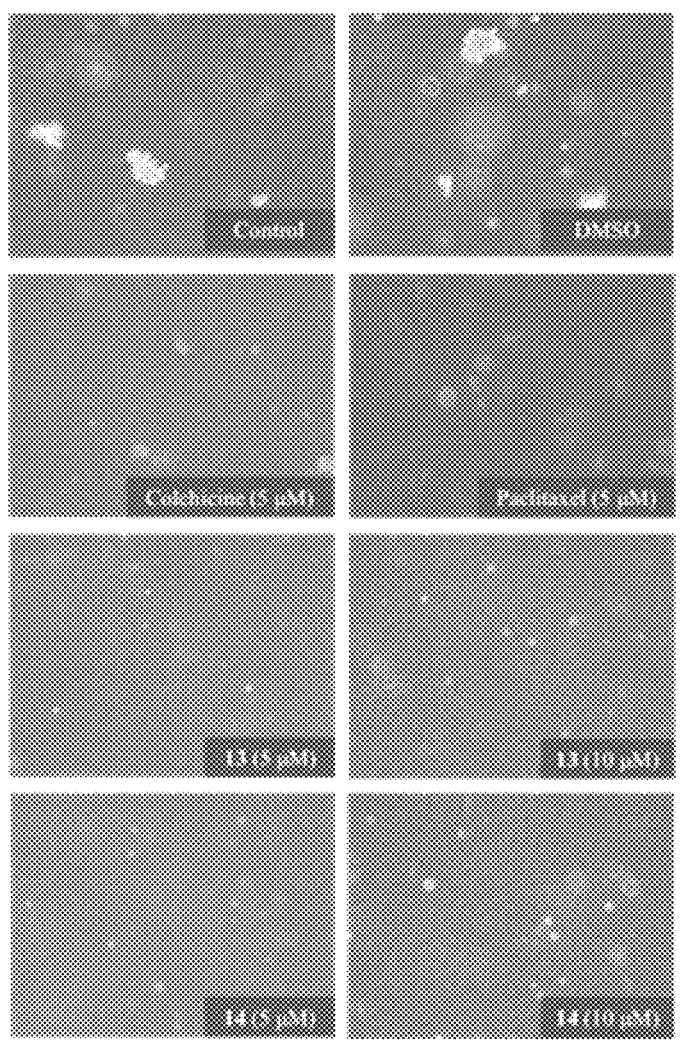
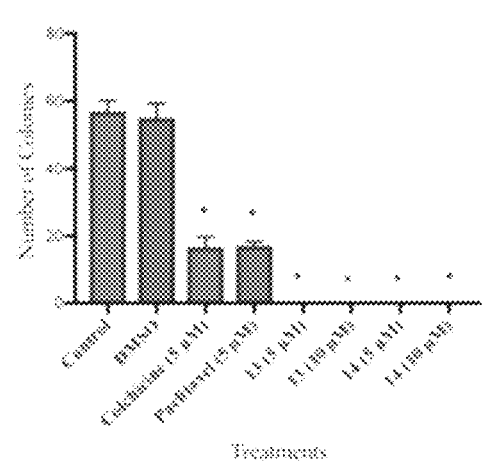

Figure 3.8
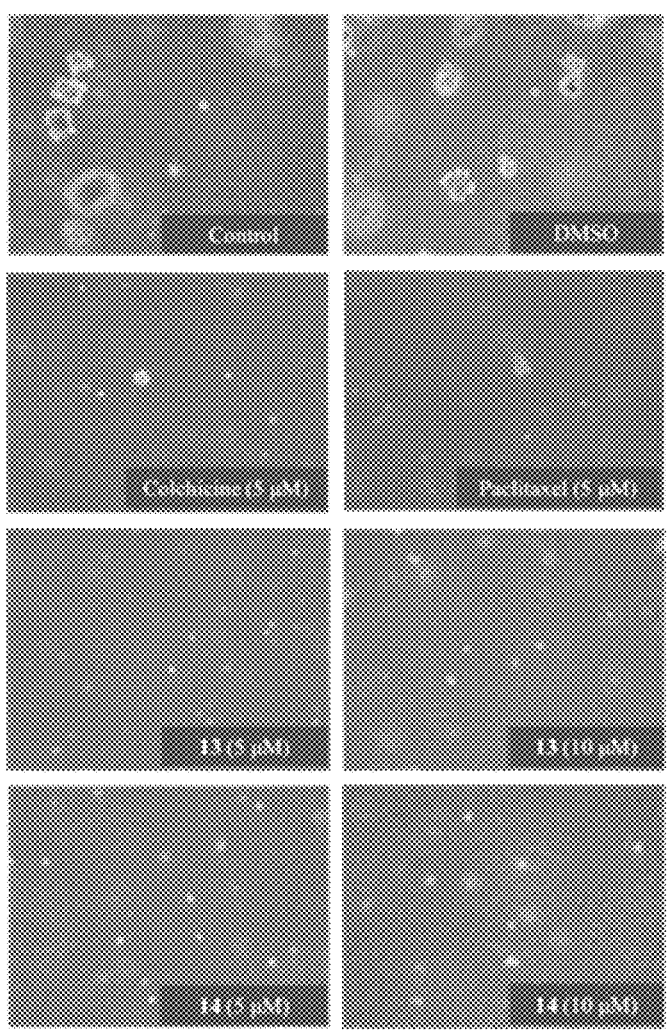
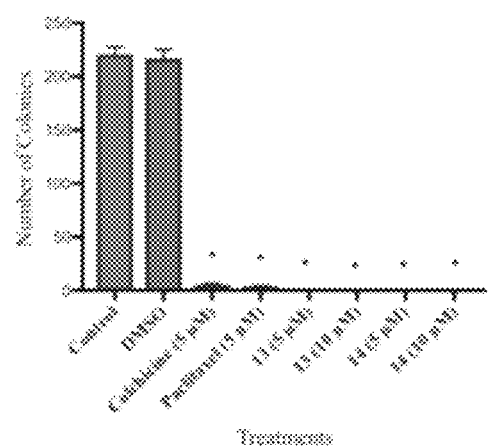

Figure 3.9
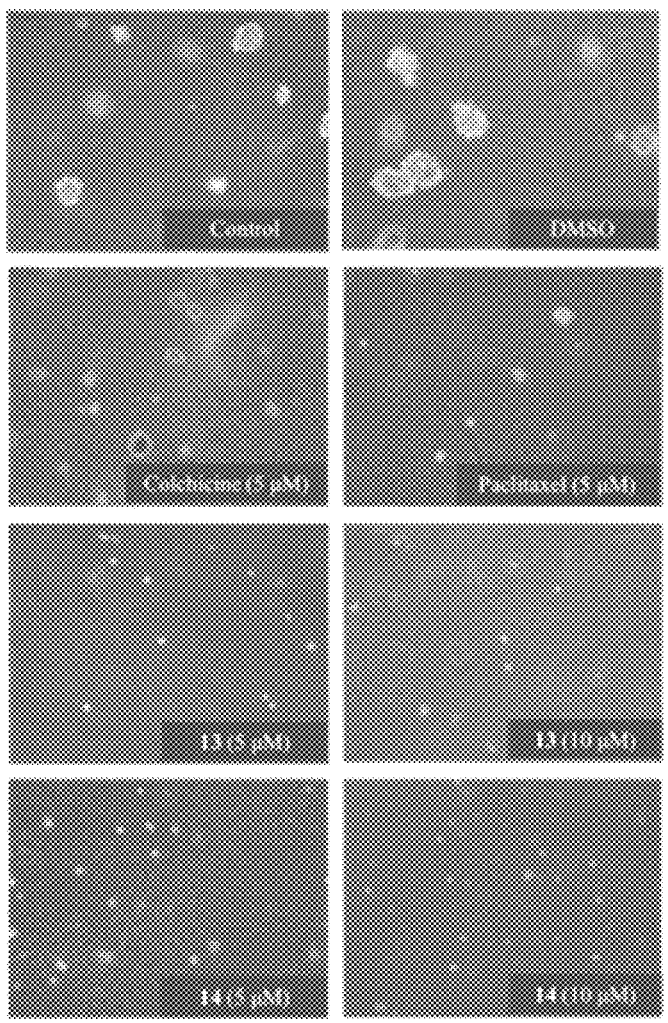
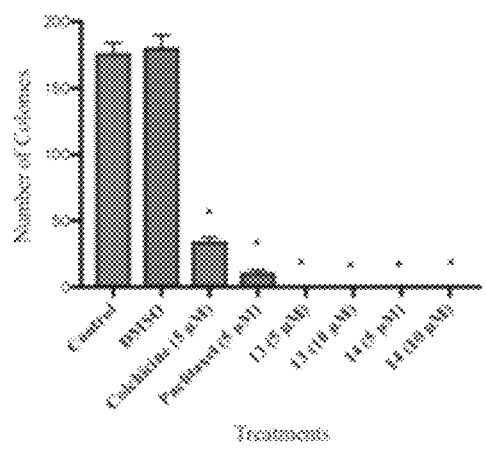

Figure 3.10
A.
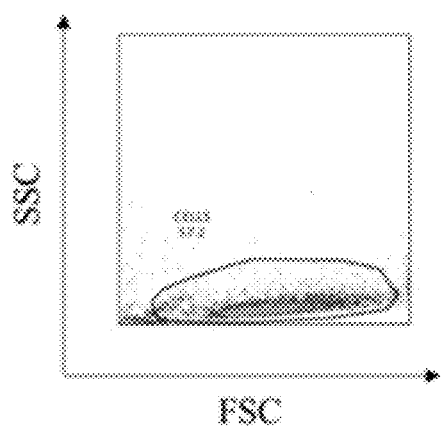
B.
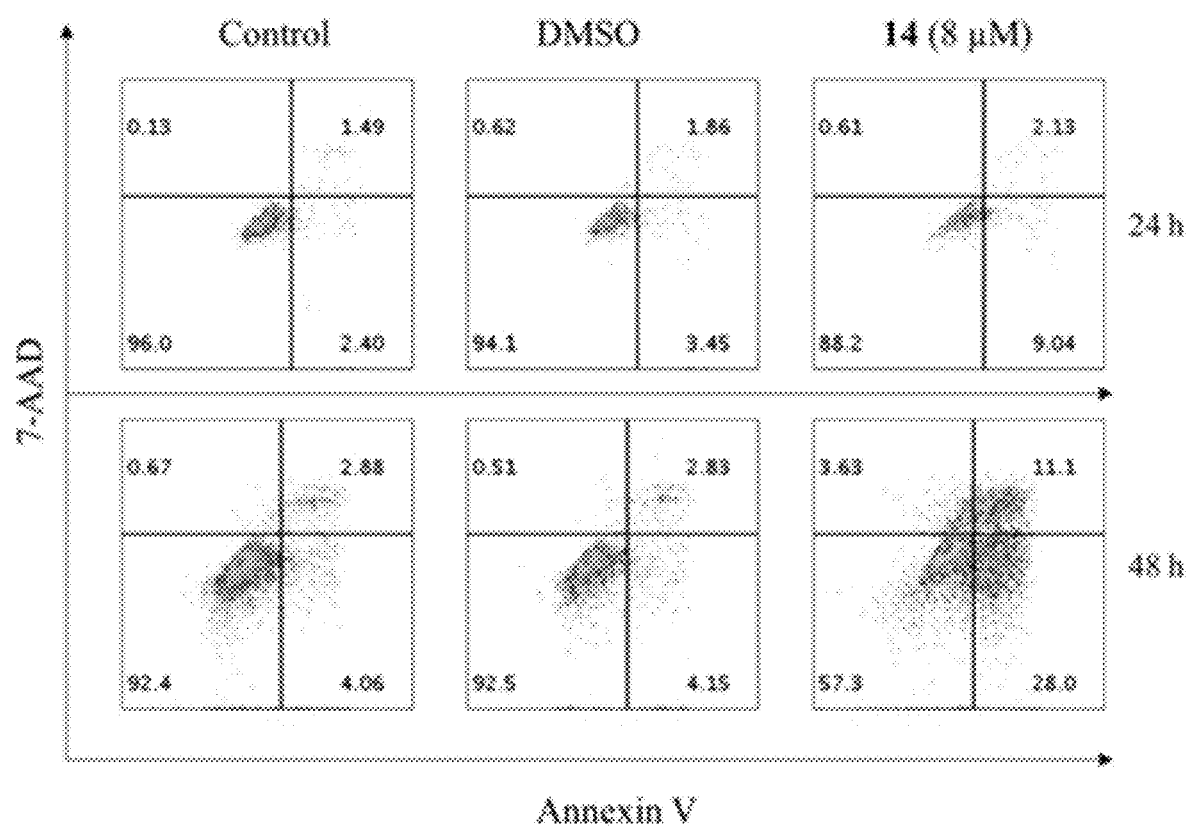

Figure 3.11
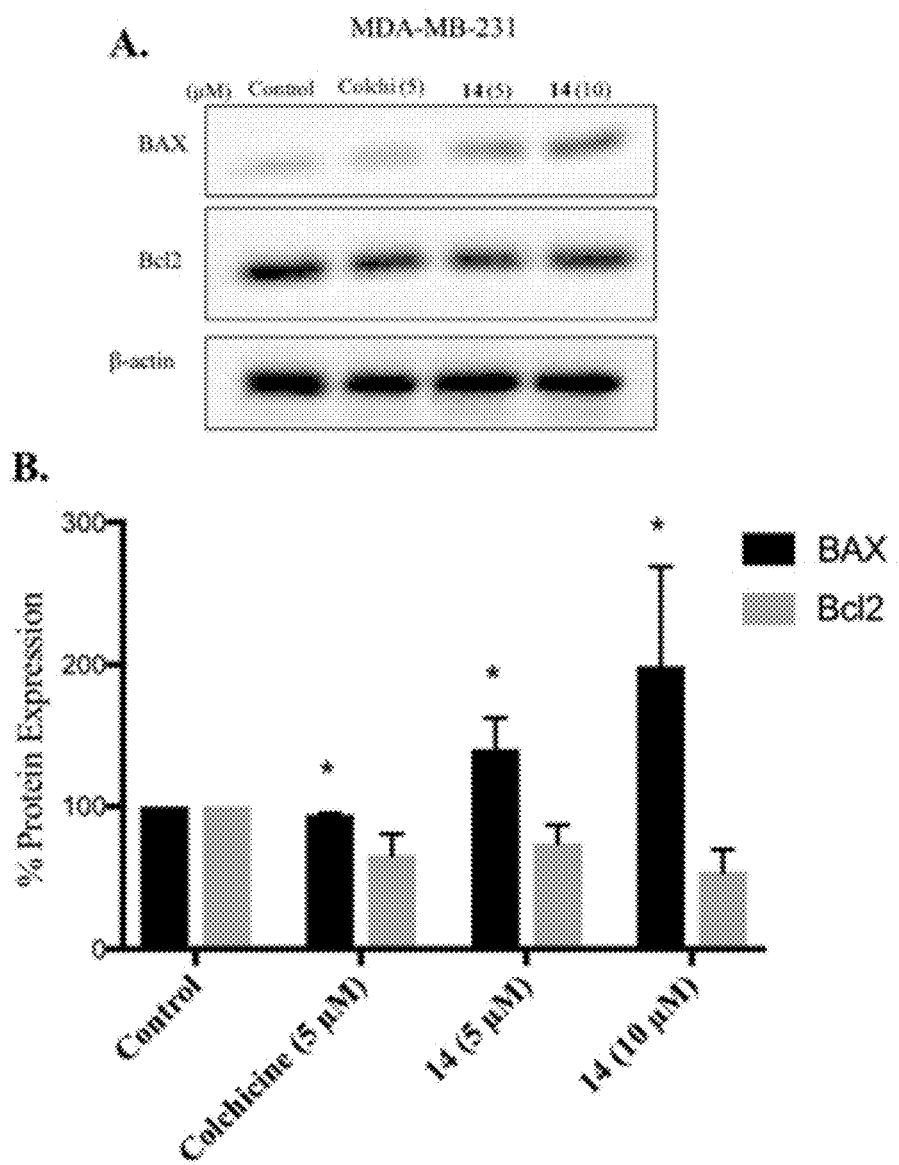

Figure 3.12
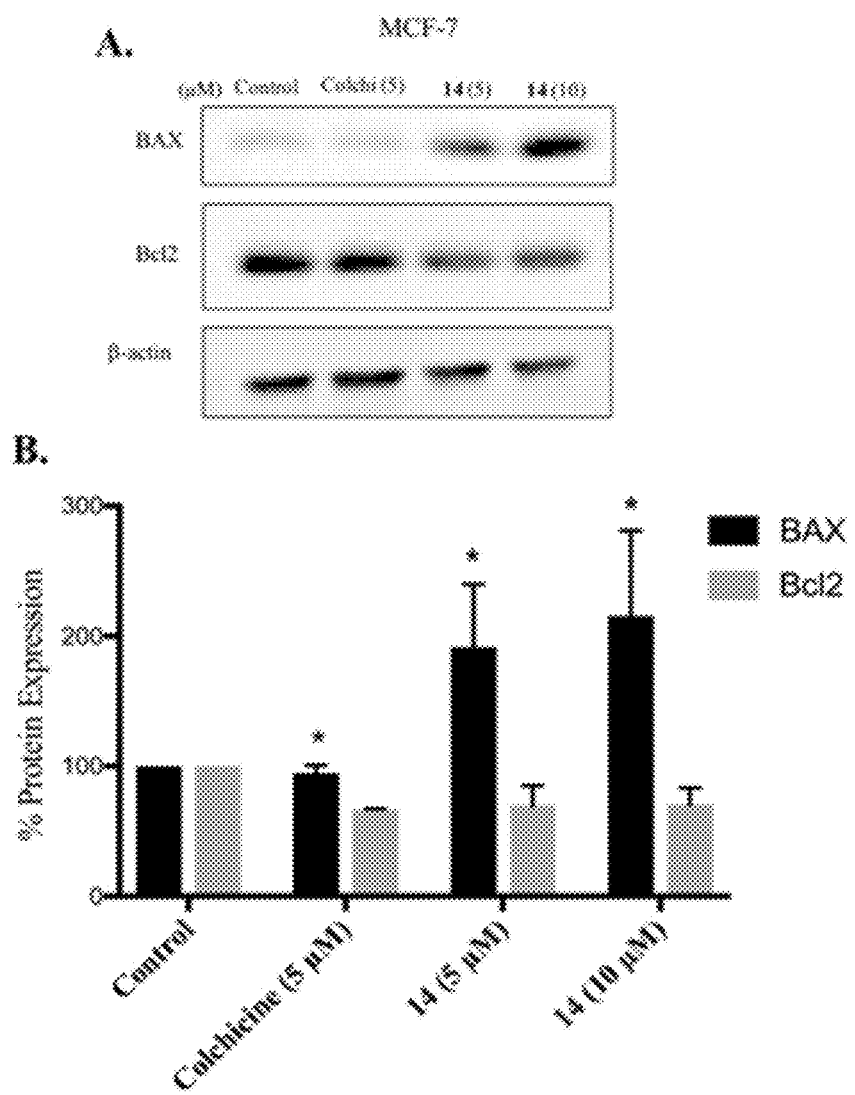

Figure 3.13
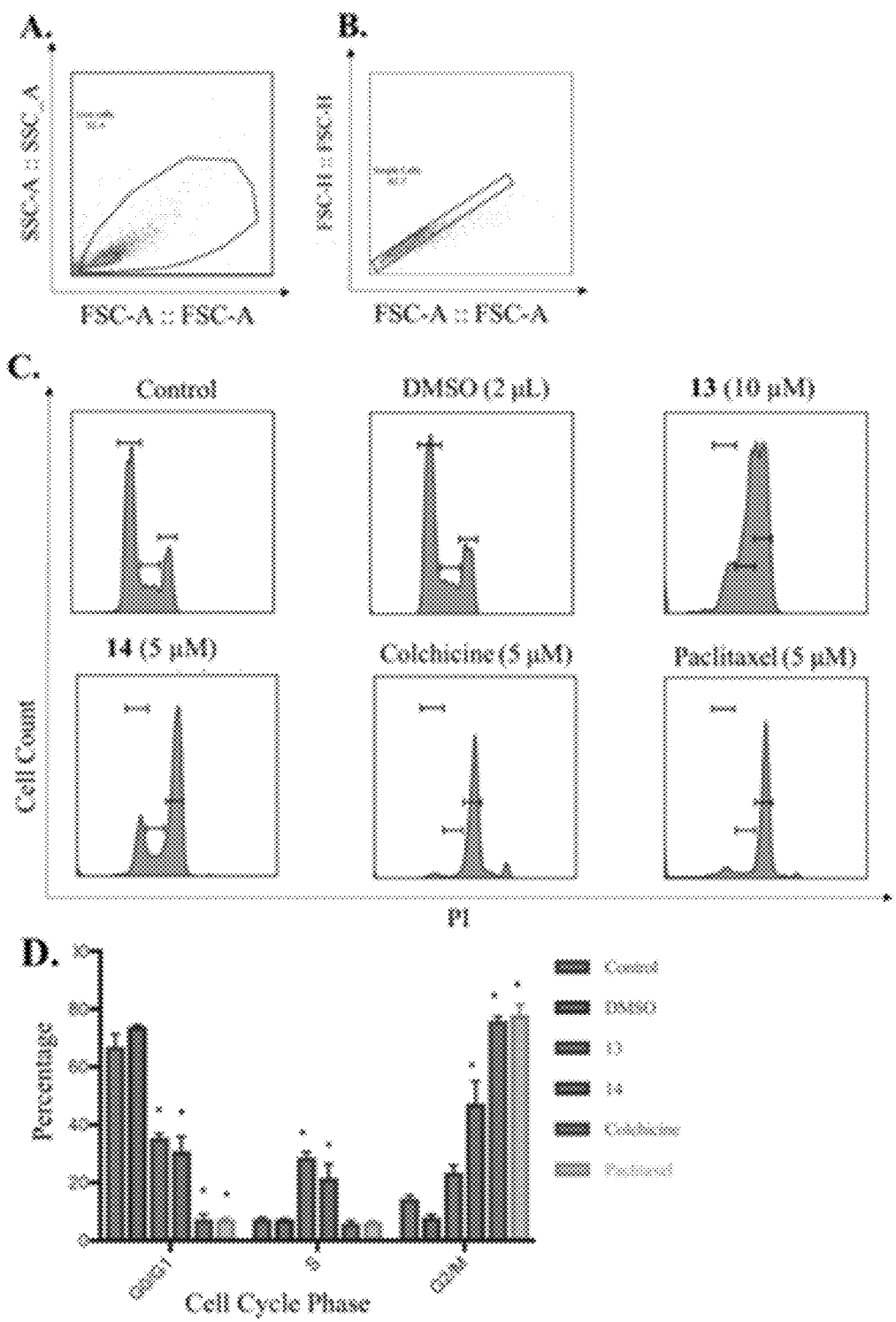

Figure 3.14
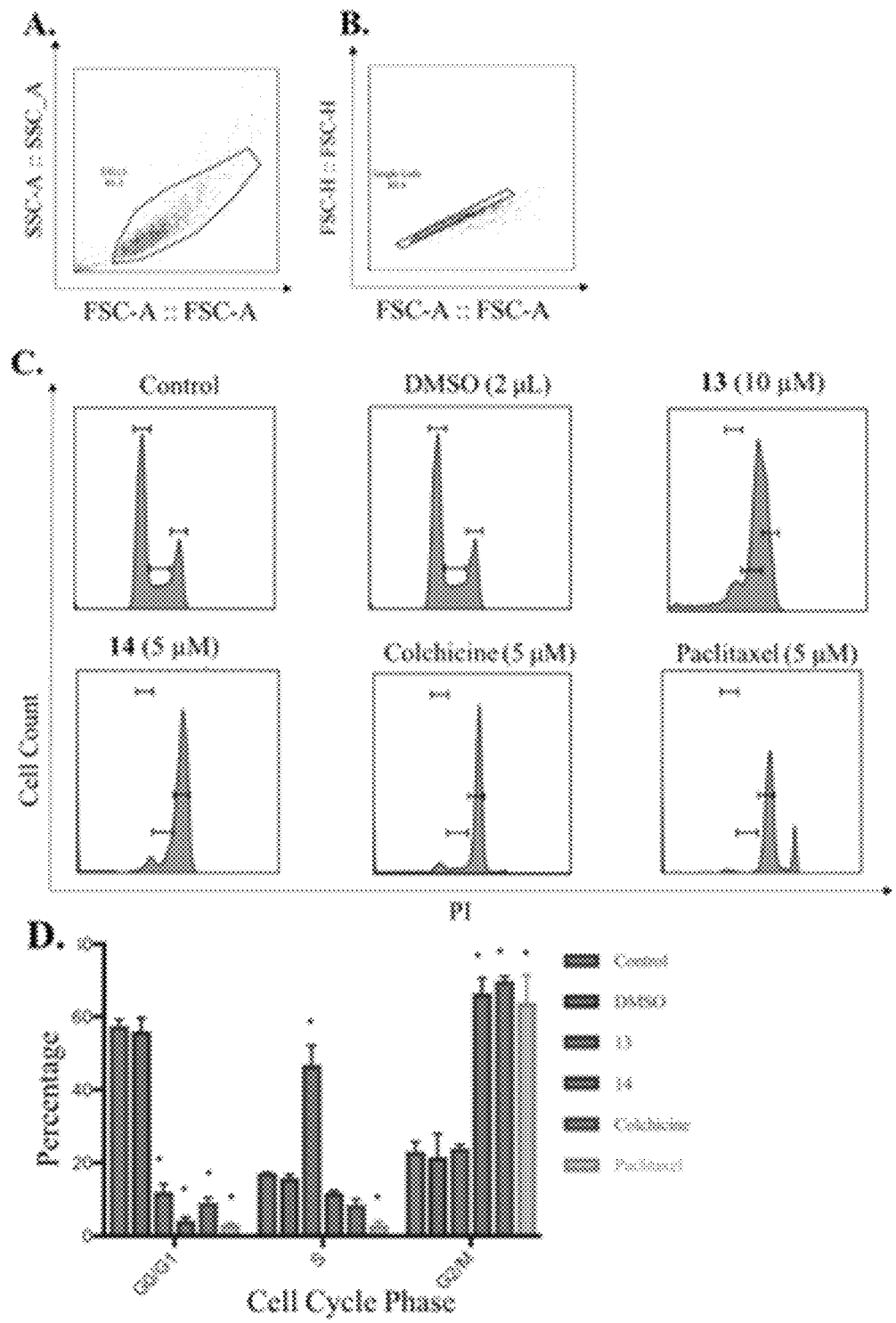

Figure 3.15
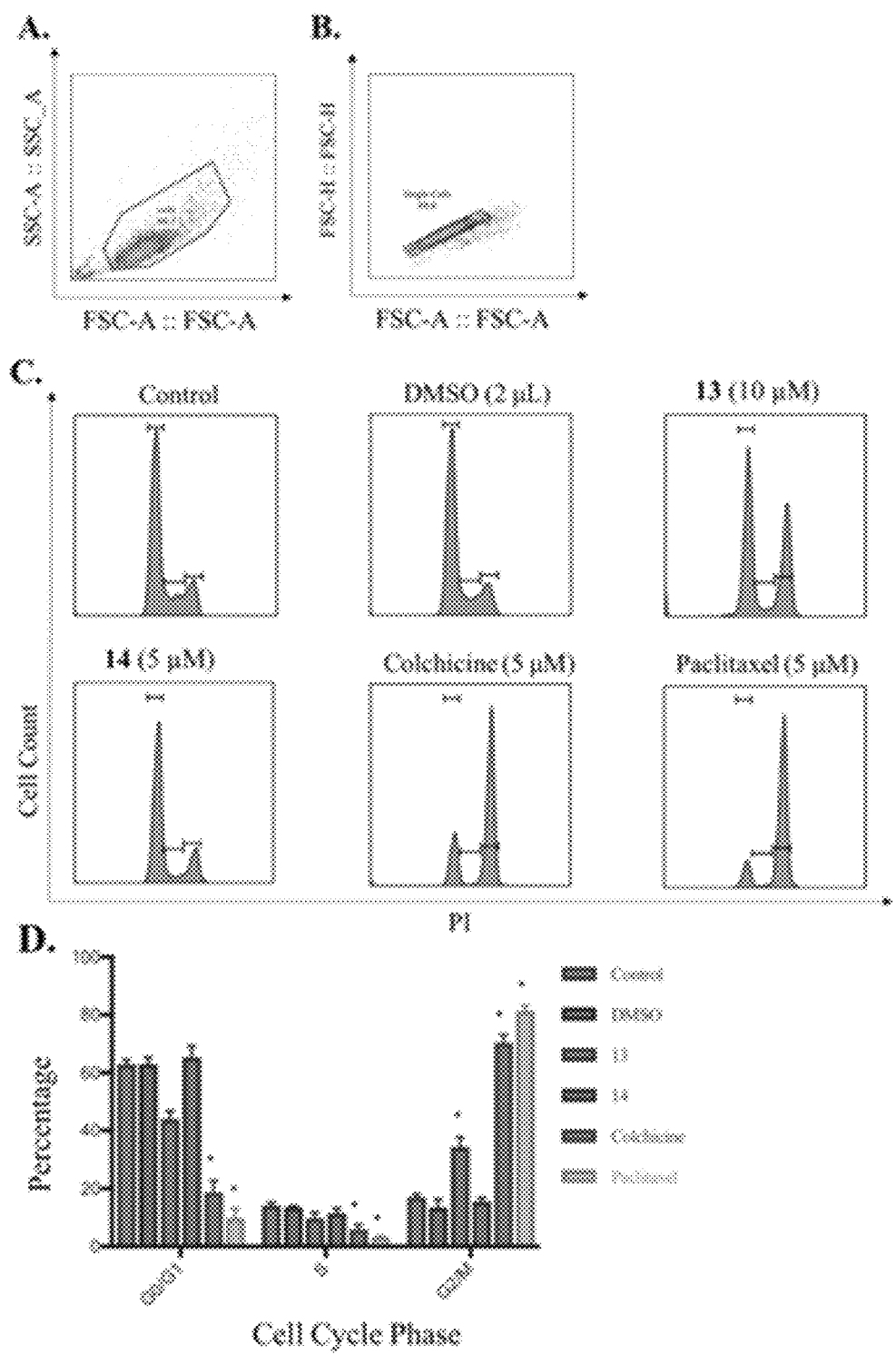

Figure 3.16
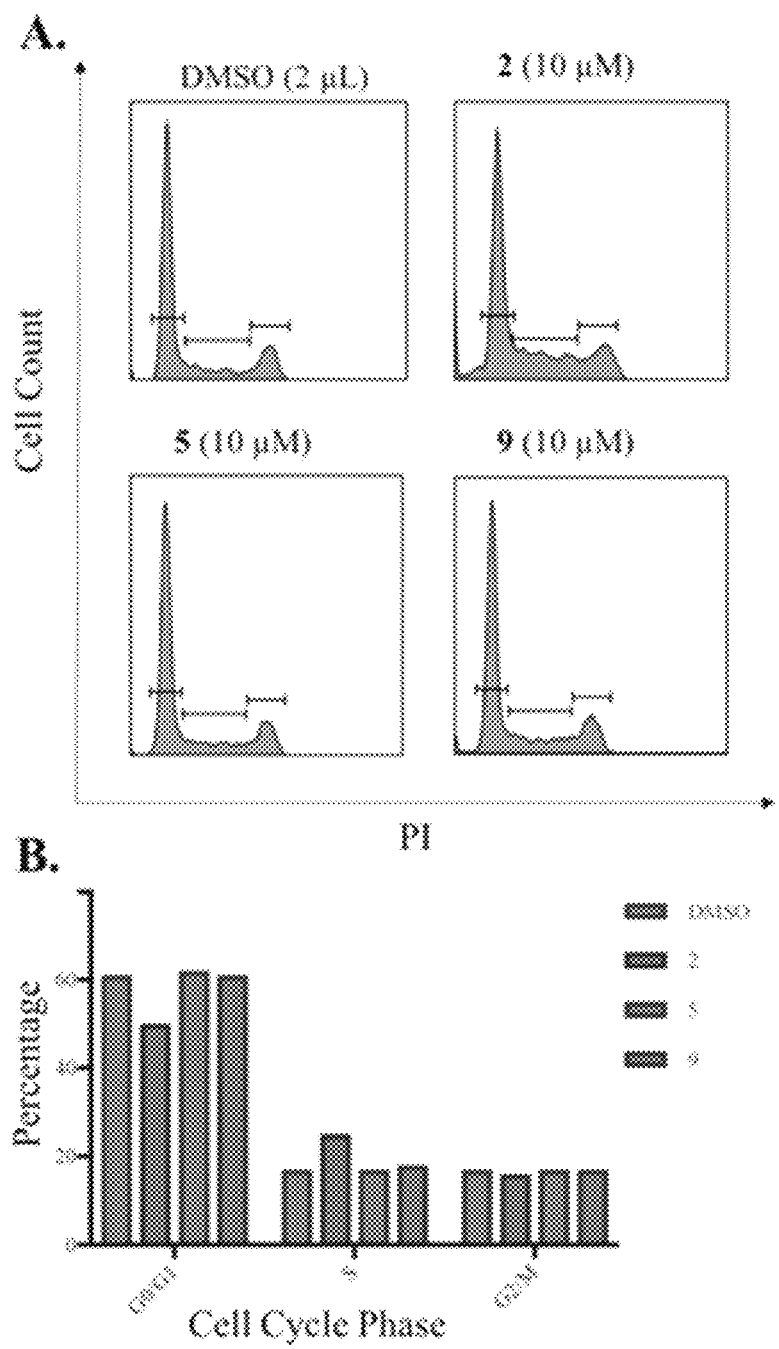

Figure 3.17
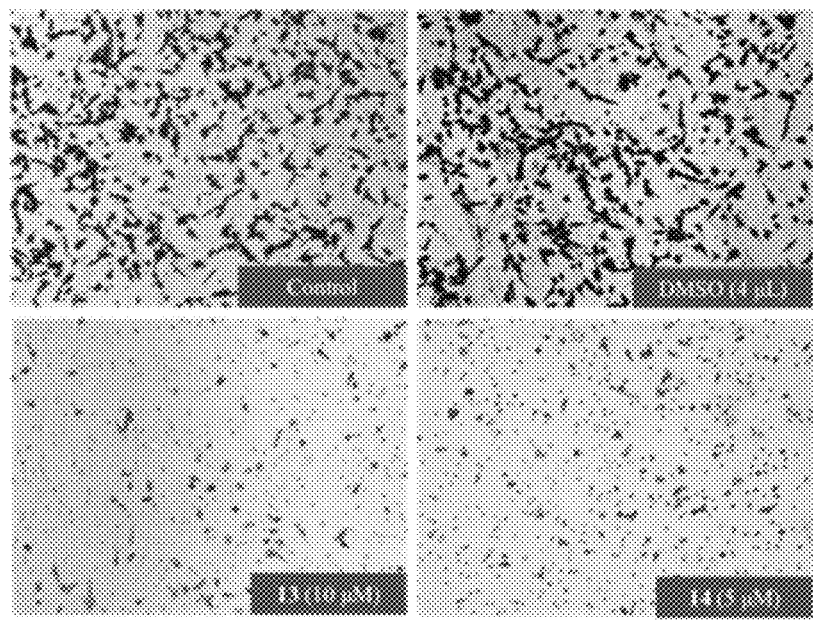
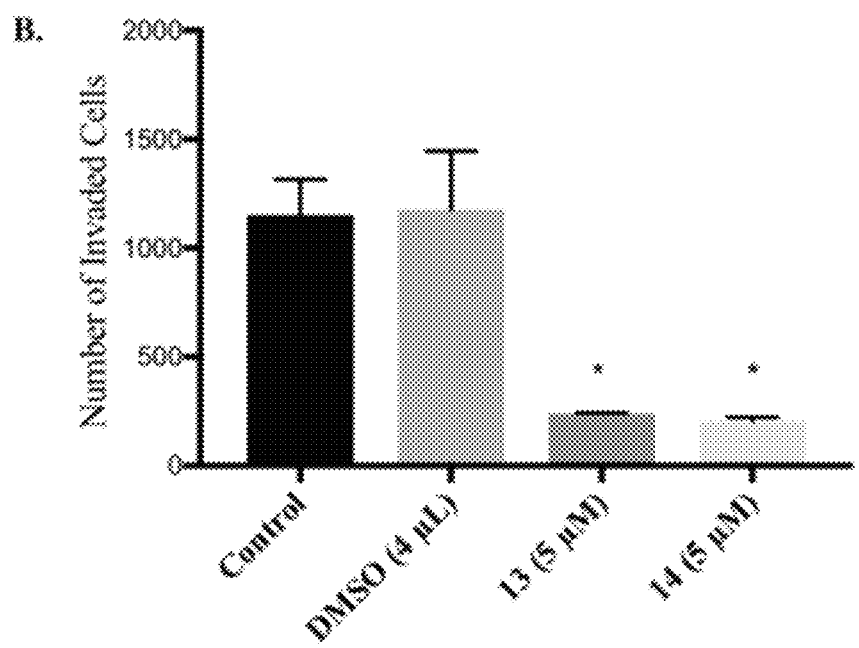

Figure 3.18
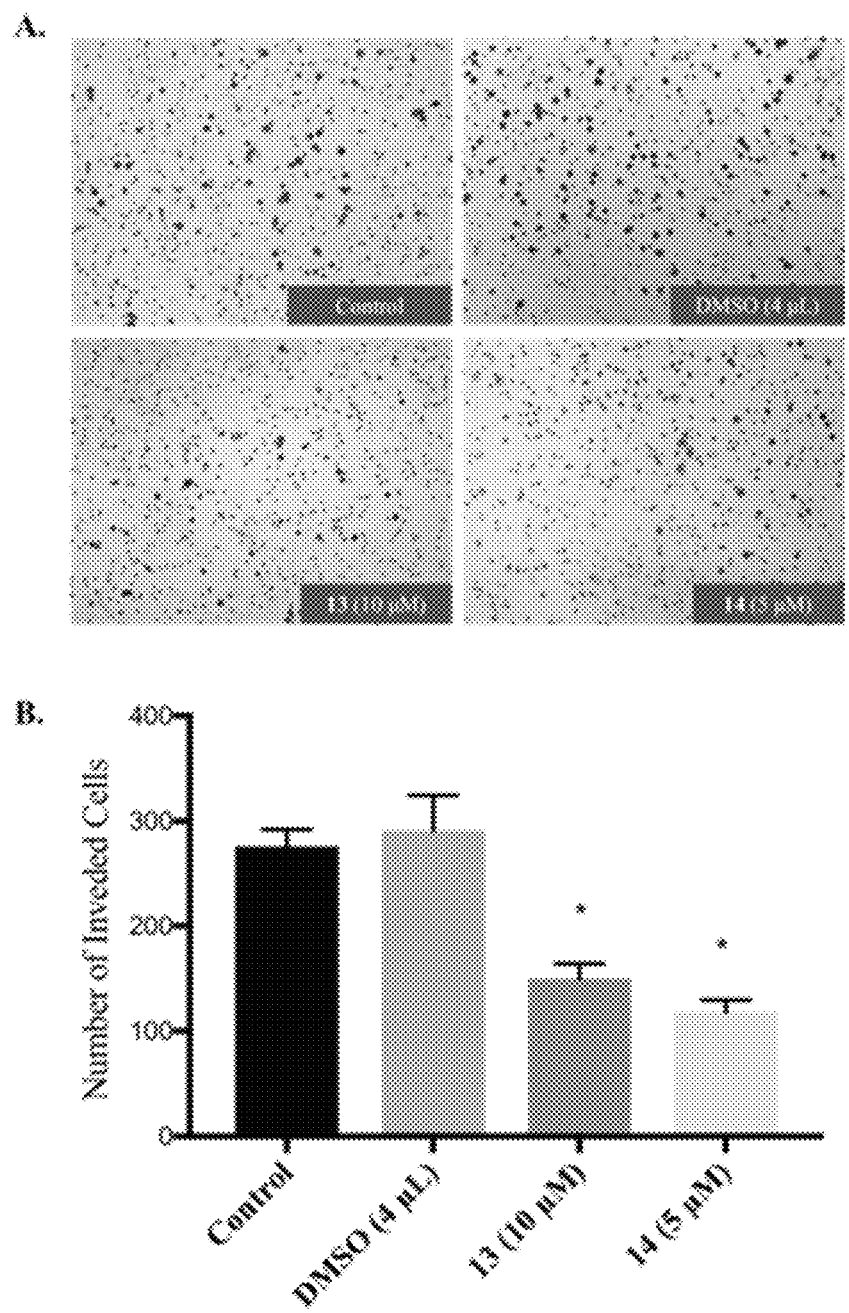

Figure 3.19
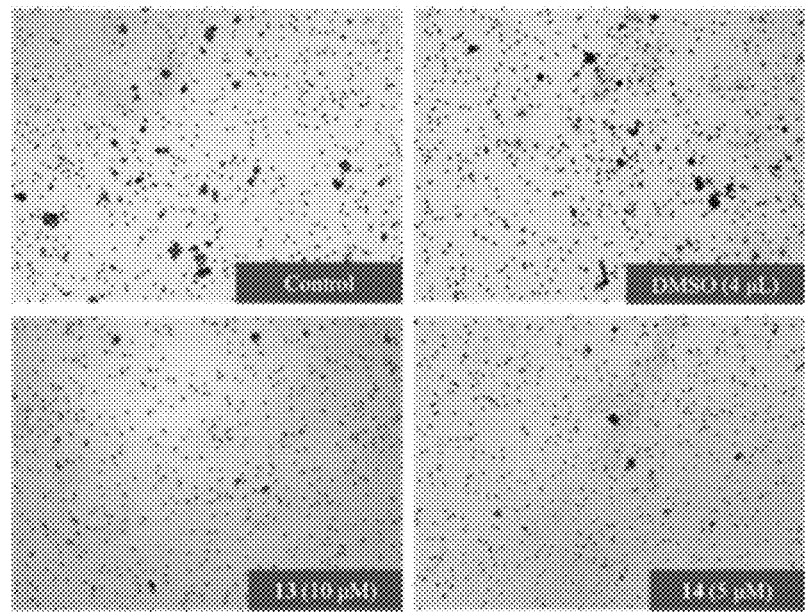
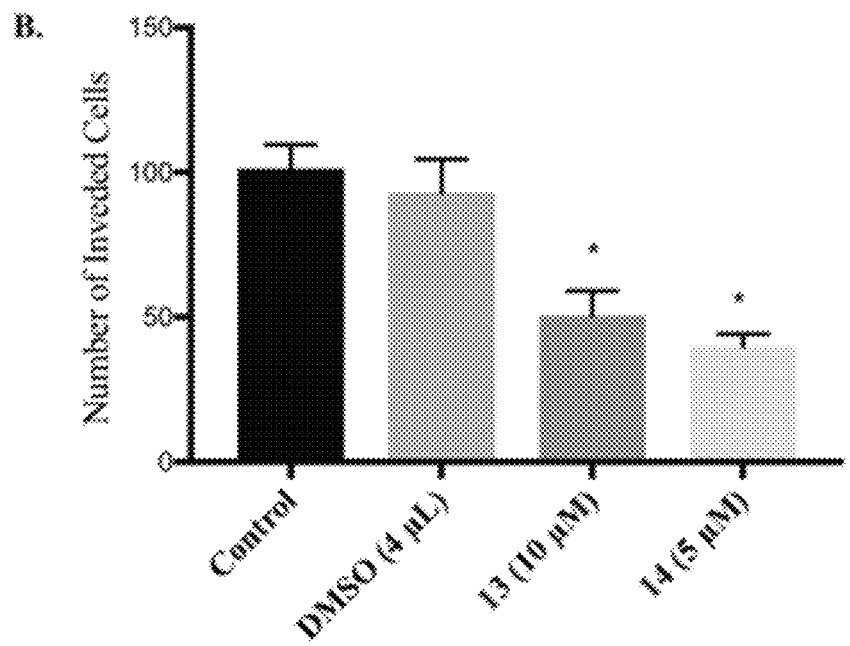

Figure 3.20
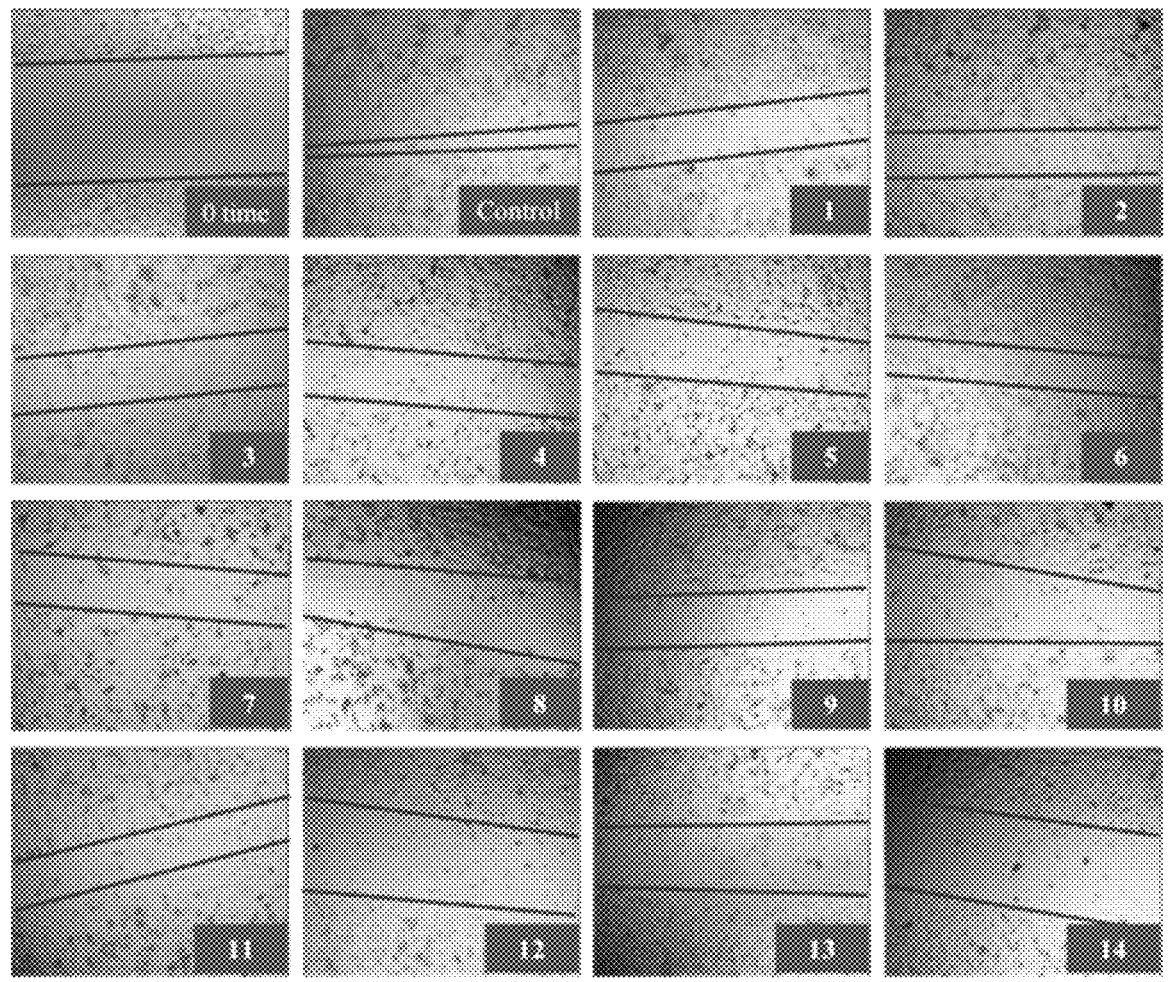

Figure 3.21
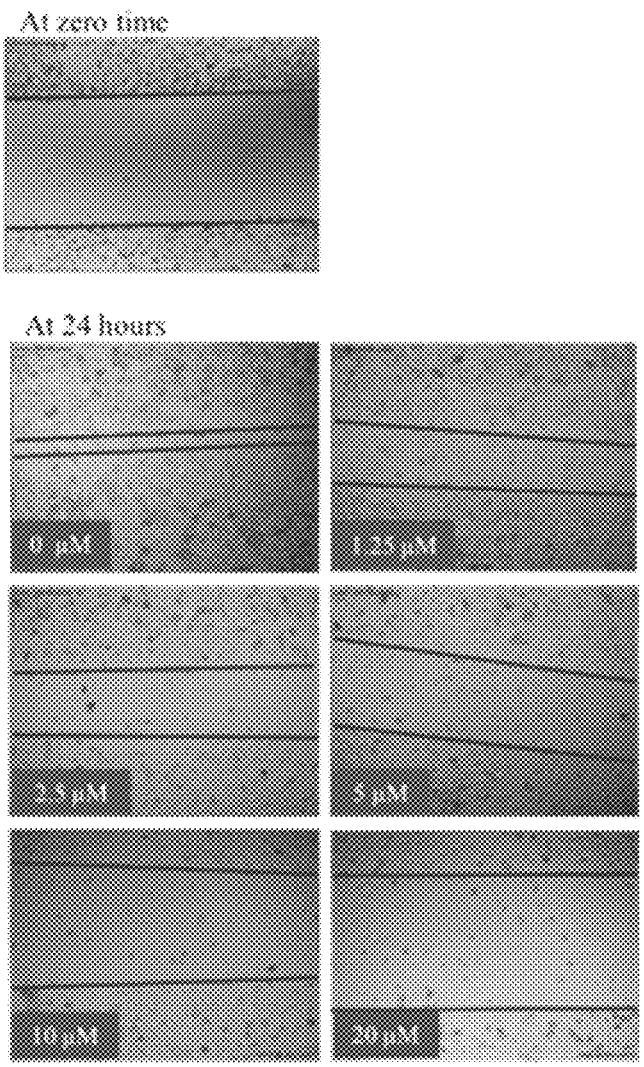
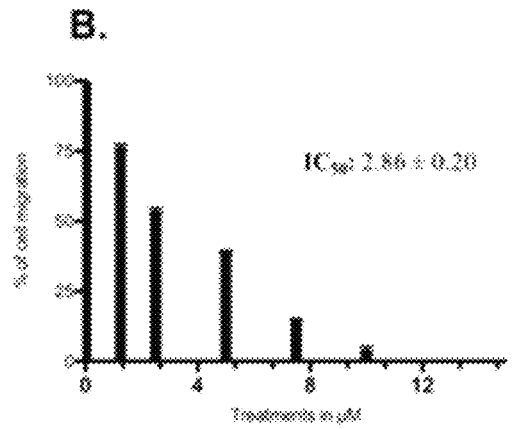

Figure 3.22
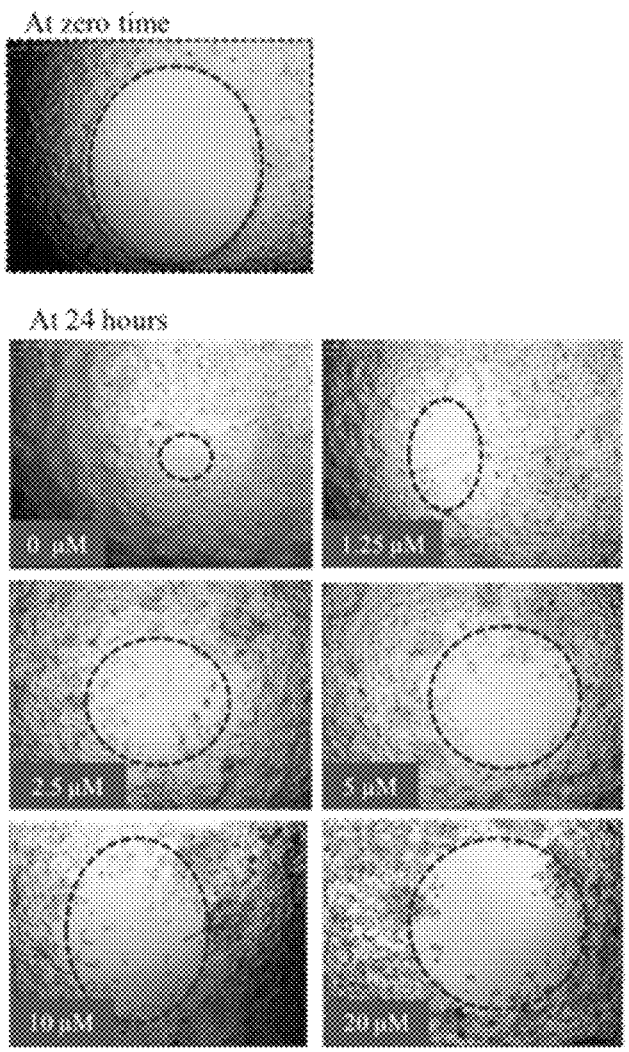
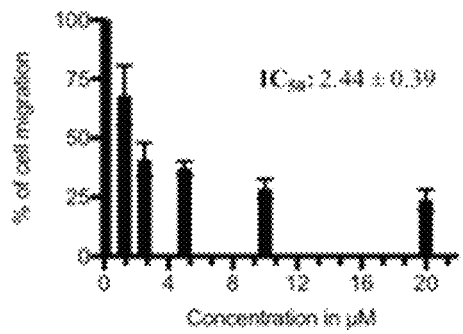

Figure 3.23
A.
At zero time
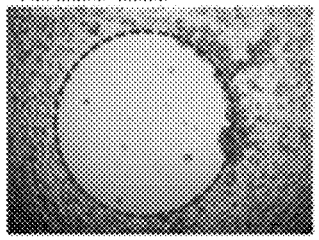
At 48 hours
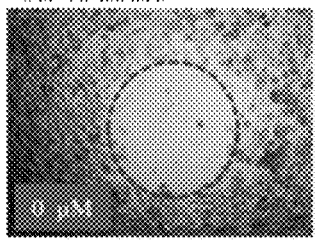 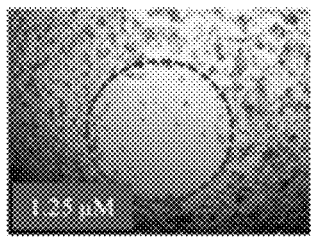
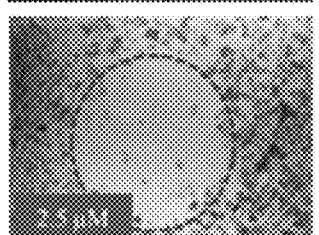 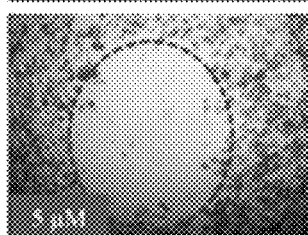
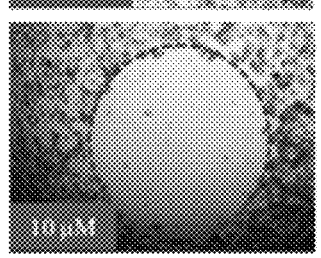 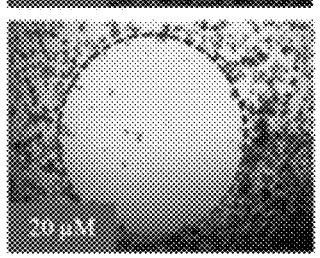
B.
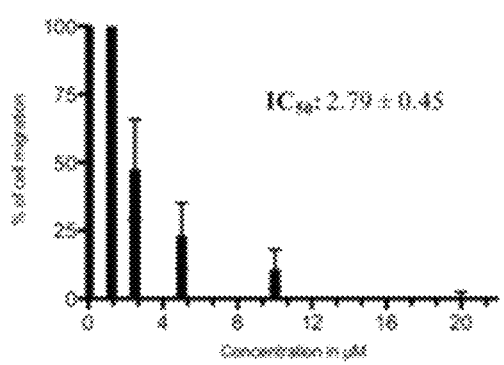

Figure 3.24
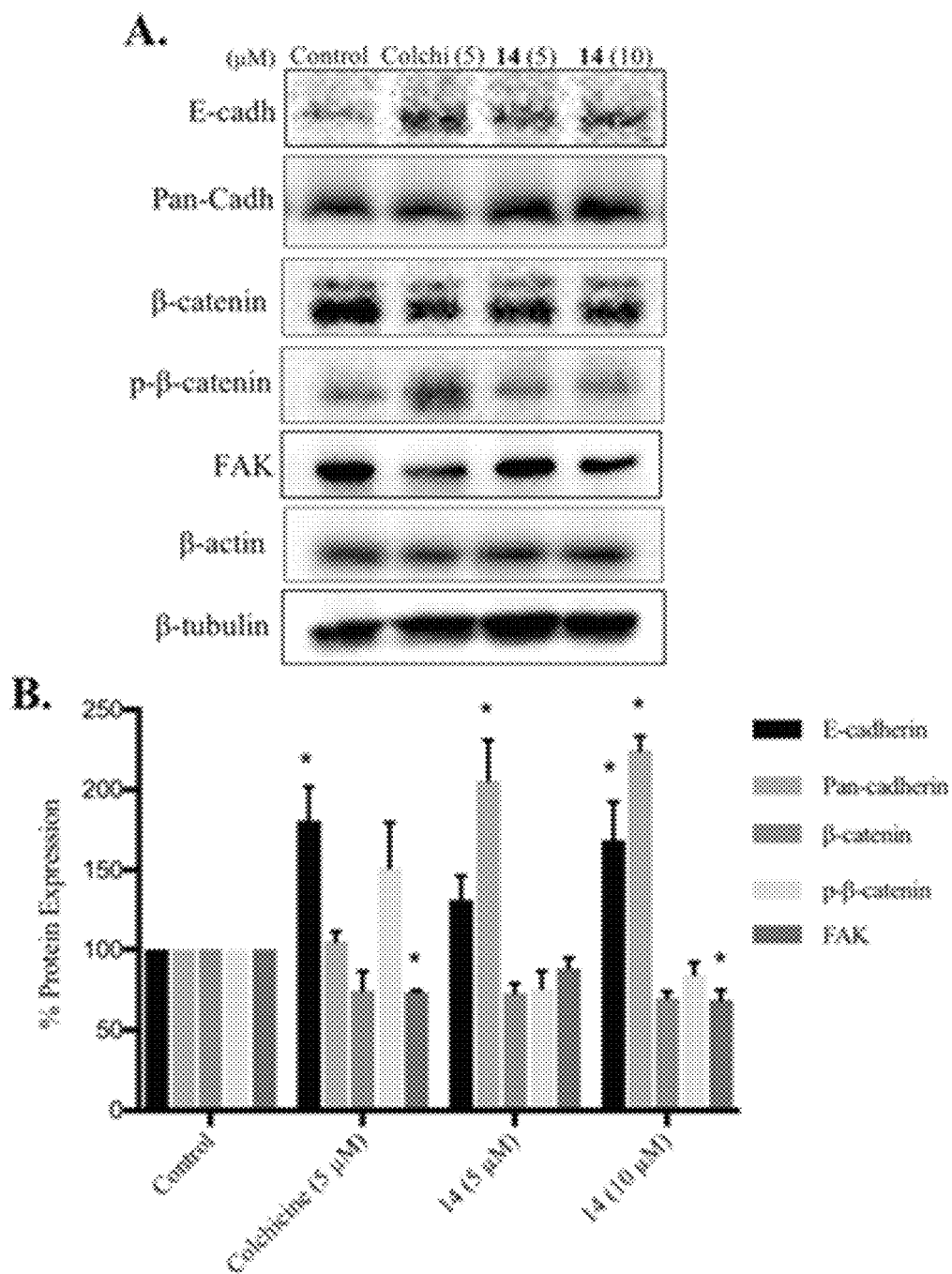

Figure 3.25
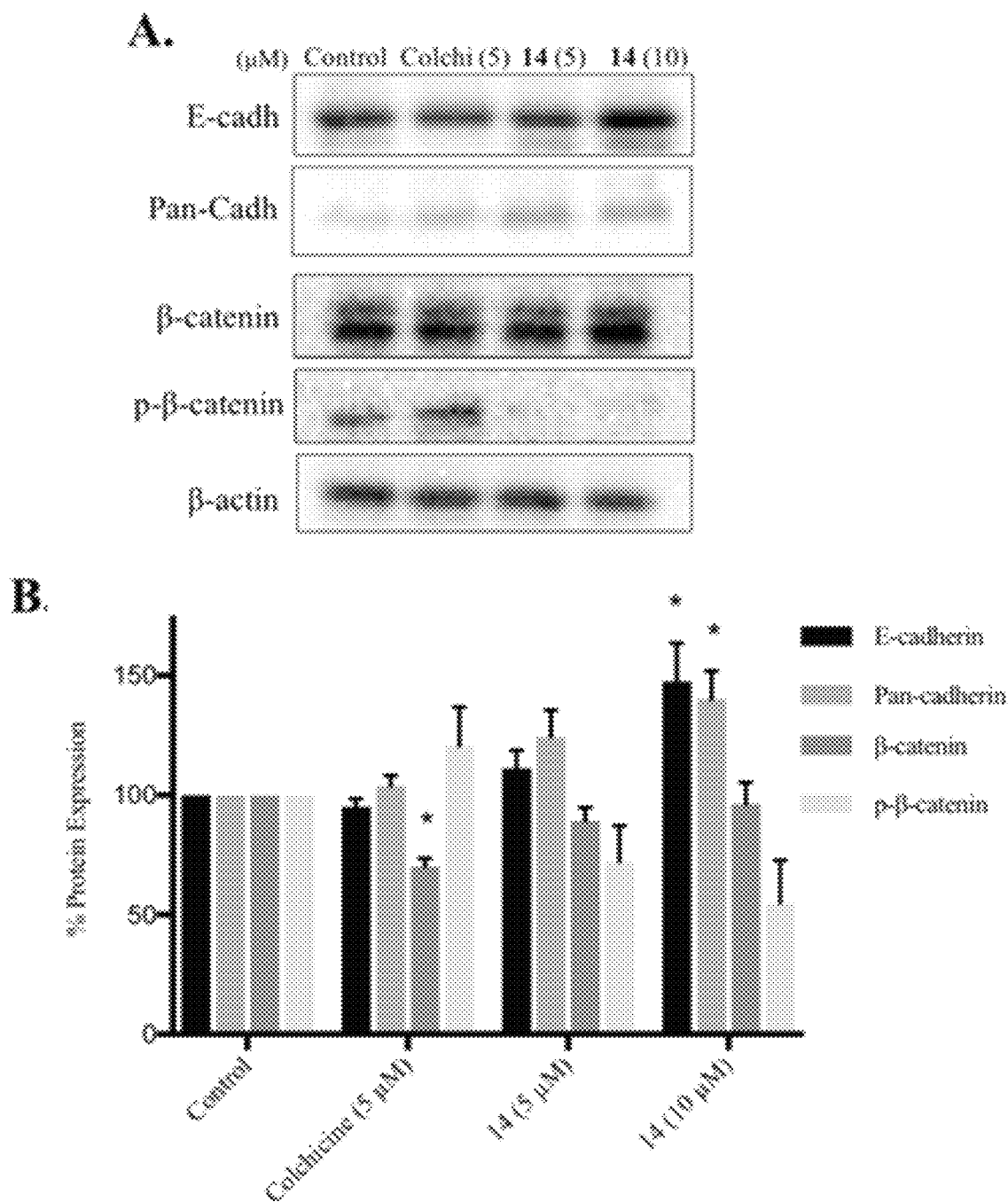

Figure 3.26
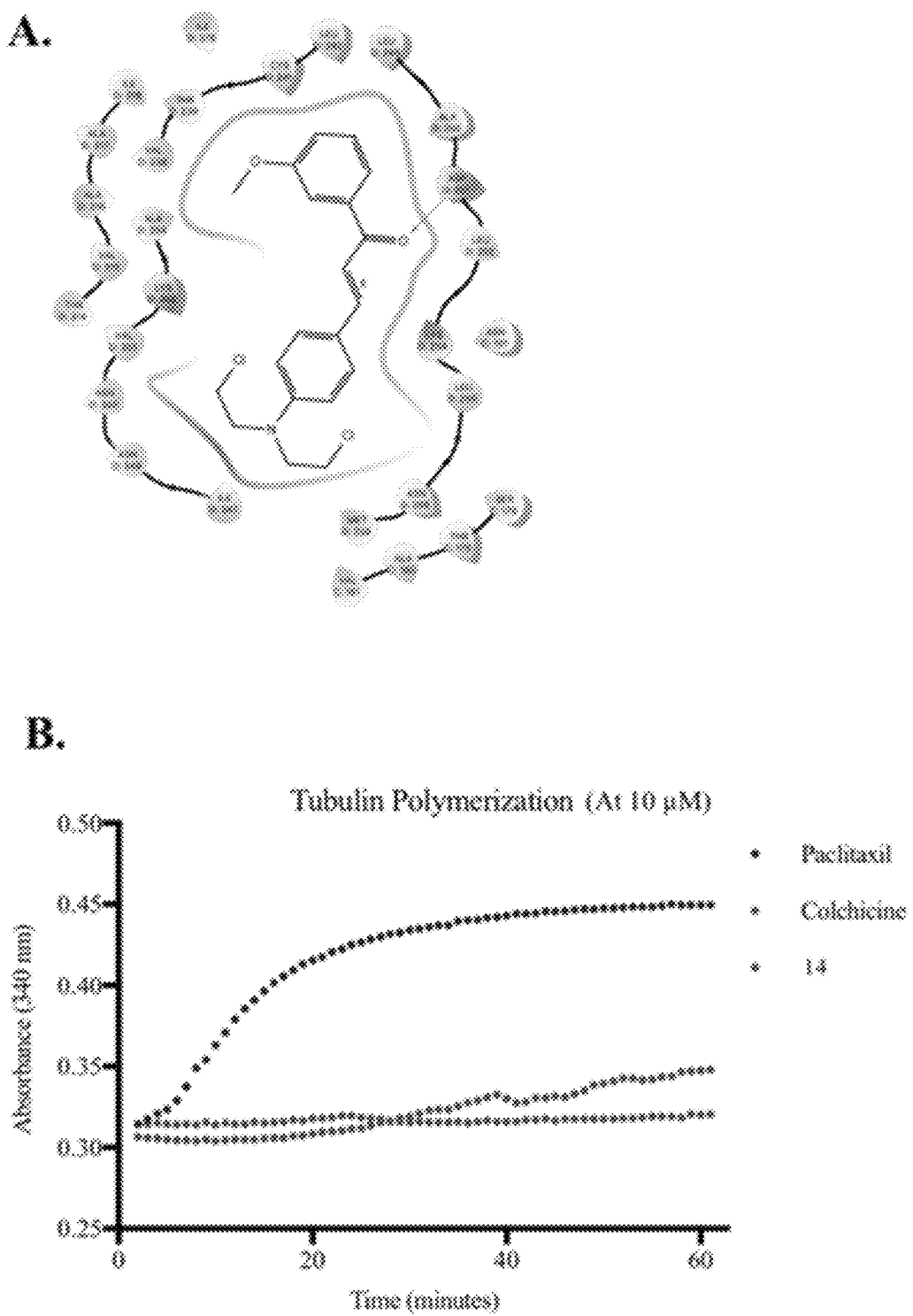

Figure 3.27
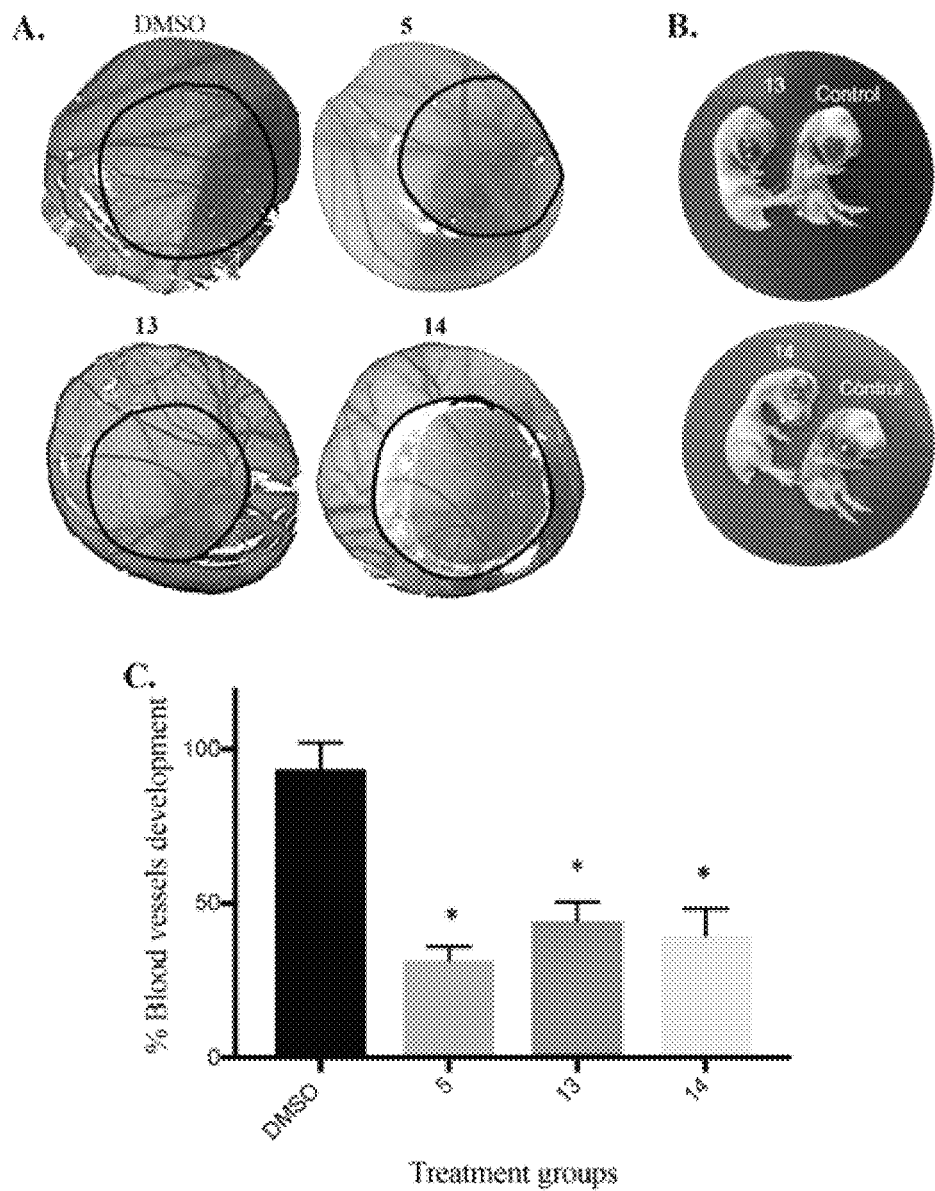

Figure 3.28
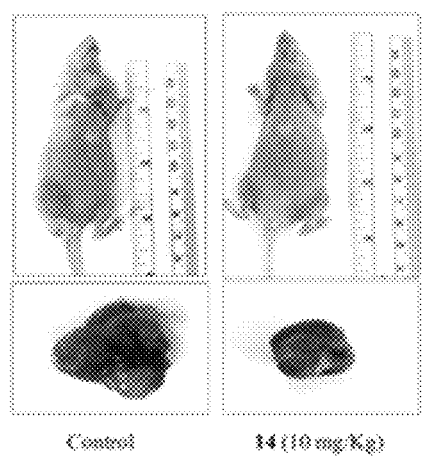
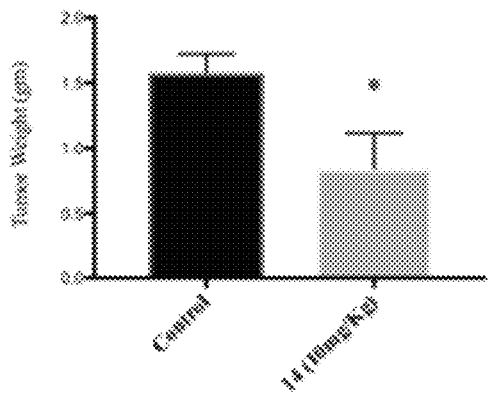
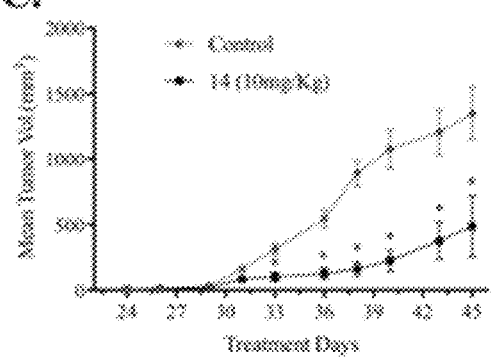
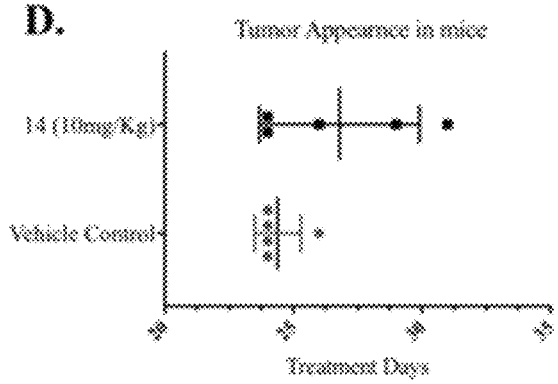
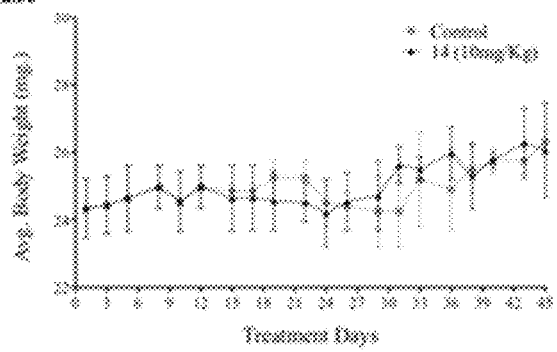
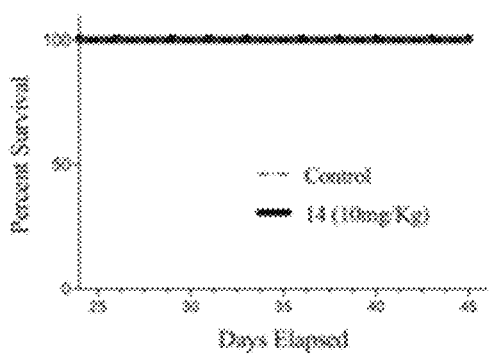

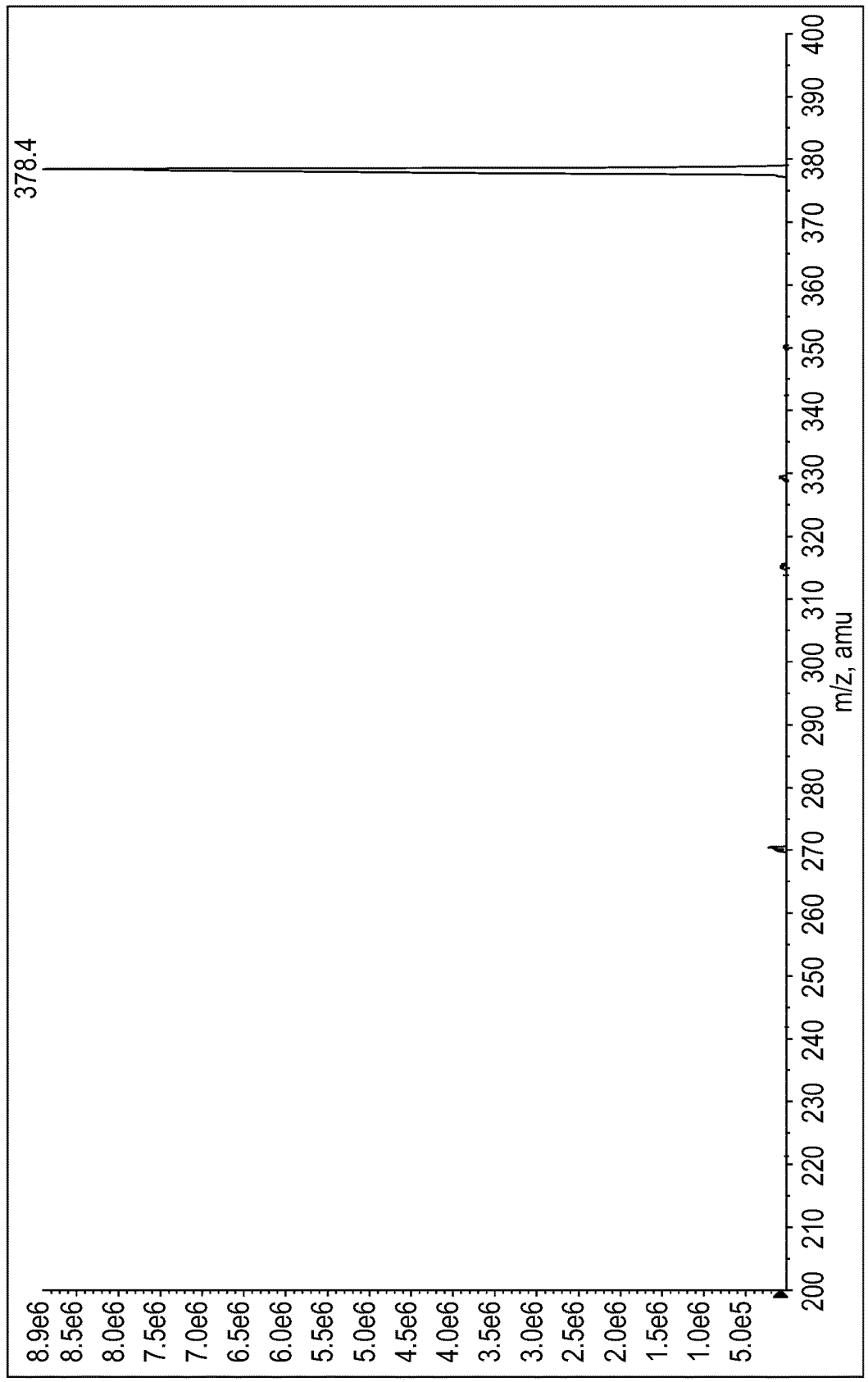
Figure 4.1
LCMS mass spectrum confirming the presence of compound 14 molecular ion peak.

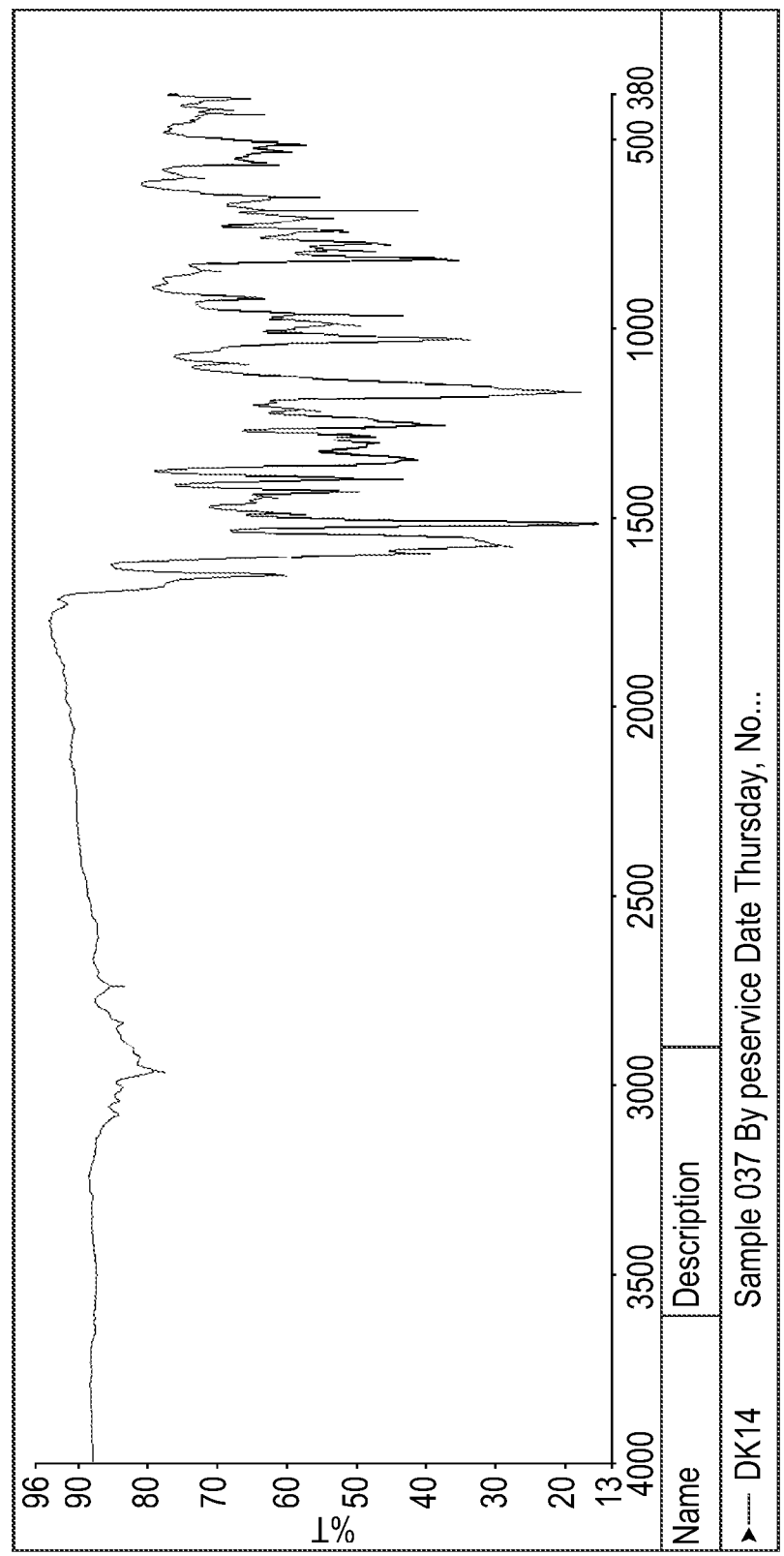
Figure 4.2
FT-IR analysis confirming the presence of compound 14 functional groups.

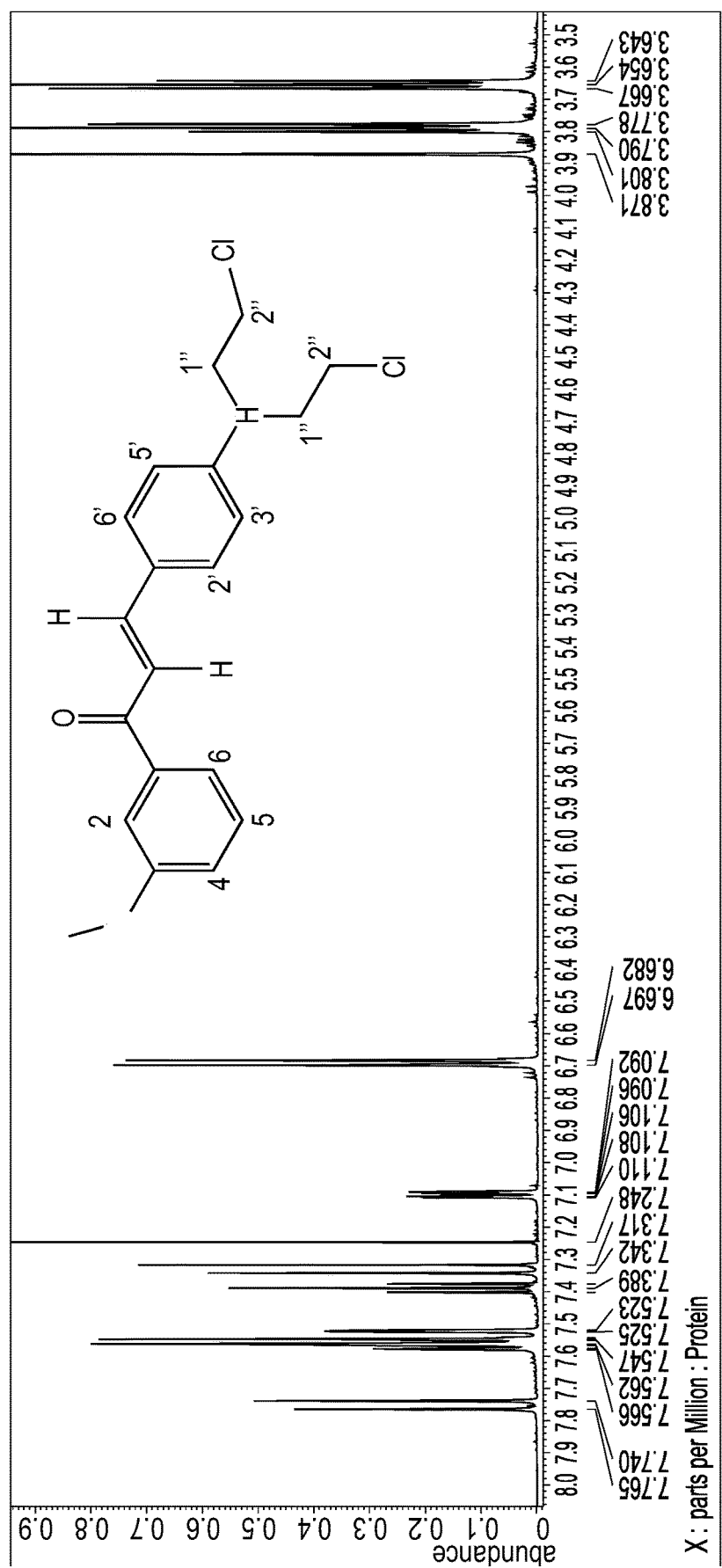
Figure 4.3
$^1$H-NMR spectra of compound 14 in CDCl$_3$.

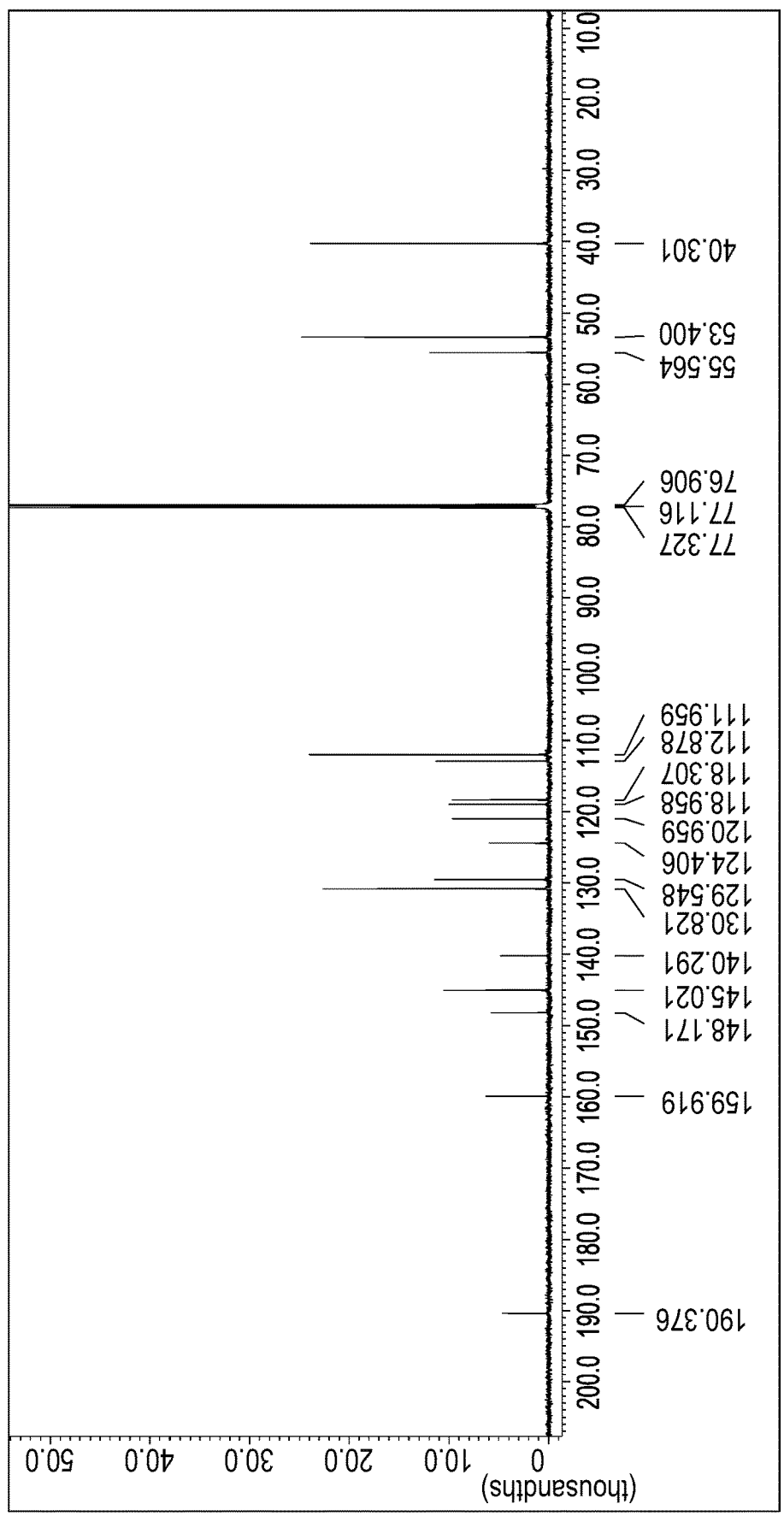
Figure 4.4. 13C-NMR spectra of compound 14 in CDCl$_3$.

Figure 4.5
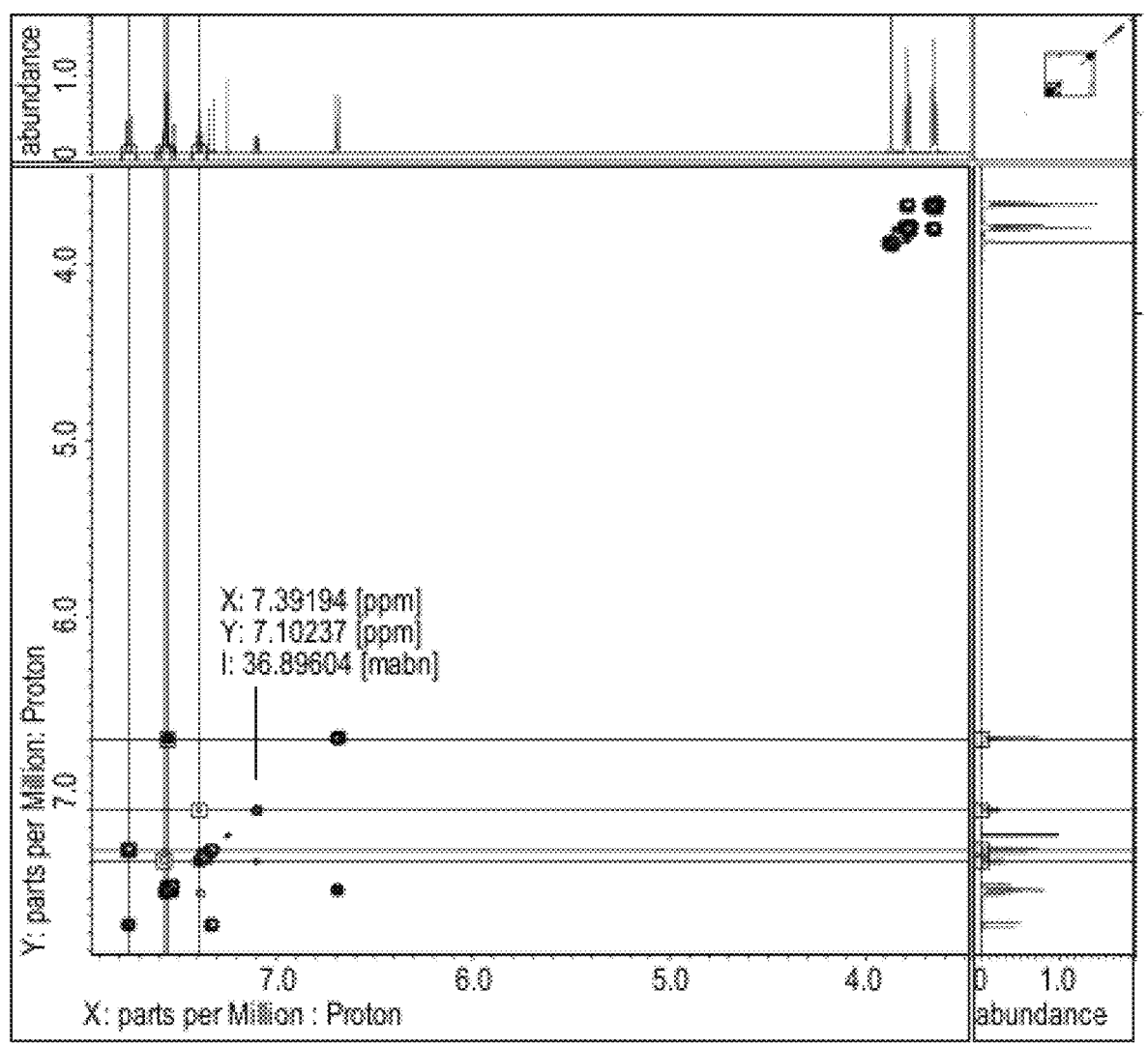
Correlation Spectroscopy (COSY) of compound 14 in CDCl$_3$.

Figure 4.6
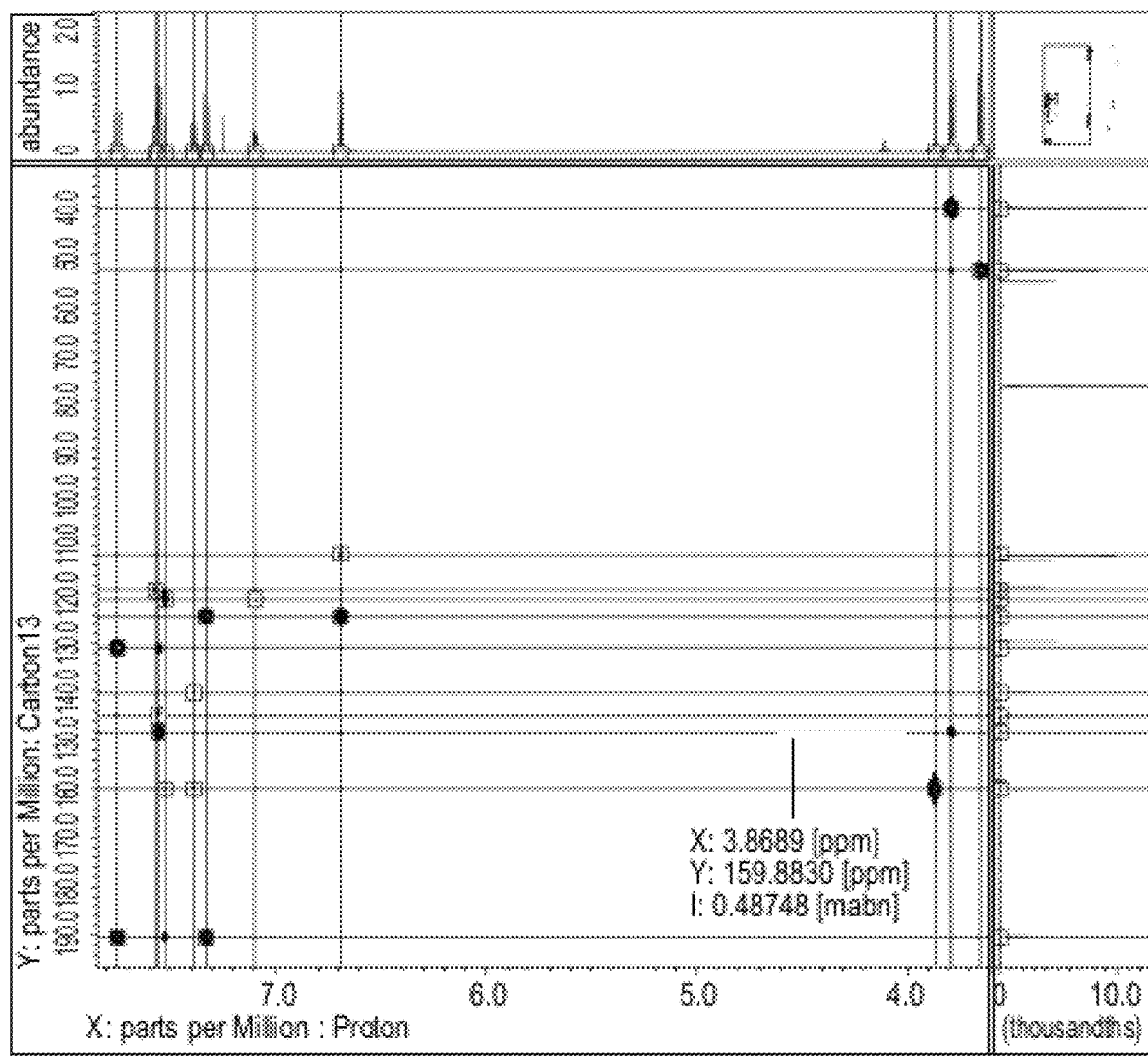
Heteronuclear Multiple Bond Correlation (HMBC) of compound 14 in CDCl$_3$.

Figure 4.7
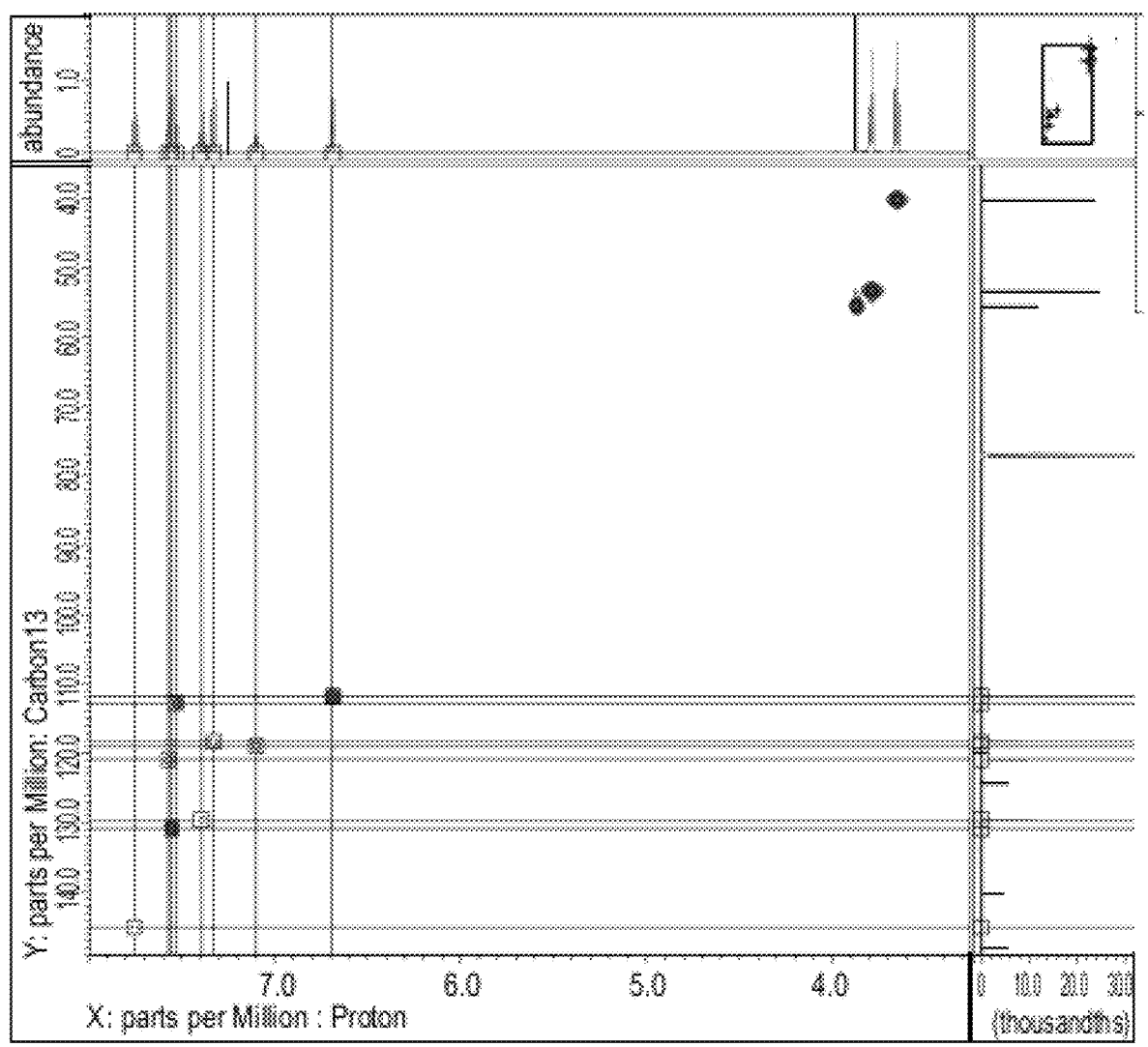
Heteronuclear Multiple Quantum Correlation (HMQC) of compound 14 in CDCl$_3$.

CHALCONE-BASED CHEMOTHERAPEUTIC COMPOUND FOR TRIPLE NEGATIVE BREAST CANCER

BACKGROUND

Triple-negative breast cancer (TNBC) is a subtype of breast malignancy that tests negative for estrogen receptors (ER), progesterone receptors (PR), and epidermal growth factor receptor 2 (HER2) protein. TNBCs are aggressive heterogeneous cancers without approved FDA targeted medications thus far. These cancers are associated with advanced and higher tumor grades, distinct metastasis, and frequent BRCA1 mutations. TNBC has a very complex pathogenesis and unpredictable prognosis. The absence of major target receptors (ER, PR, and HER2) required for the majority of available breast cancer drugs has complicated the challenge of identifying suitable therapeutic avenues. Therefore, TNBC patients have tremendously poorer prognosis, do not respond satisfactorily to current therapies, and have remarkably higher relapse rate and disease recurrence compared with non-TNBCs. Therefore, identification of new alternatives or improved treatment options to combat this deadly disease is highly needed. Among possible treatment options for this disease are chalcone derivatives. Various derived products with chalcone scaffold are generally considered excellent candidates for the development of anticancer drugs. Their unique core chemical structure is comprised of two benzene rings (A and B) and a double bond conjugated with a carbonyl group. Thus far, chalcone derivatives have not been thoroughly studied for the management of TNBC and none has entered into subsequent development steps as a potential targeted treatment for TNBCs. Nitrogen containing heterocyclic organic molecules, alicyclic amines (e.g. pyrrolidine, morpholine and piperidine) have shown a great promise in promoting anticancer activities in a range of different cancer types including breast. Nitrogen mustard was previously identified as an attractive scaffold in targeting cancer tumors.

The present inventors have investigated whether chalcone derivatives incorporating nitrogen based functional groups (such as pyrrolidine, morpholine, piperidine, and nitrogen mustard) may exert optimal activity as a new lead in anticancer drugs with improved efficacy and safety profiles for the treatment of TNBC patients.

The present inventors have synthesized a variety of novel chalcone-based compounds with anticancer activities and evaluated them in vitro for their role in targeting TNBC. Additionally, they conducted virtual screening studies to predict the predominant binding mode(s) of the most promising compounds on potential molecular targets, explored anticancer activities of synthesized compounds in vivo in different animal models, and provided possible safety profiles of the most promising compounds.

SUMMARY

Provided herein are compounds, compositions, and methods useful for the treatment of breast cancers, particularly TNBCs.

In certain aspects, provided herein are compounds of formula (I):

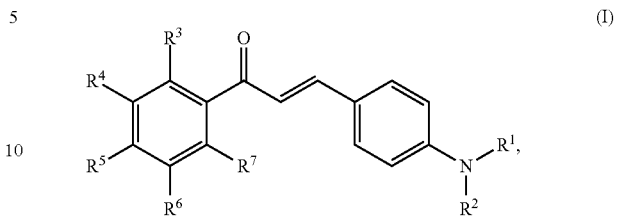

or a pharmaceutically acceptable salt or solvate thereof, wherein $R^1$ and $R^2$ are each independently haloalkyl; or $R^1$ and $R^2$ together with the N atom form a heterocyclic group;

$R^3$, $R^4$, $R^5$, $R^6$, and $R^7$ are each independently selected from hydrogen, halo, alkyl, hydroxyl, alkoxyl, amino, alkylamino, thio, alkylthio, sulfonyl, alkylsulfonyl, and heterocyclic group; or $R^3$ and $R^4$, or $R^4$ and $R^5$, or $R^5$ and $R^6$, or $R^6$ and $R^7$ form a group

wherein "⁓" indicates point of attachment, wherein $R^8$ is hydrogen or alkyl, and the rest of $R^3$, $R^4$, $R^5$, $R^6$, and $R^7$ are each independent selected from hydrogen, halo, and alkyl.

In certain aspects, provided herein are compositions comprising any of the compounds provided herein. In some embodiments, the compositions are pharmaceutical compositions comprising any of the compounds provided herein and a pharmaceutically acceptable carrier and/or excipient.

In certain aspects, provided herein are methods of treating cancer in a subject in need of the treatment, the methods comprising administering an effective amount or a therapeutically effective amount of any of the compounds or compositions provided herein, to the subject. In some embodiments of the methods, the cancer is breast cancer. In some embodiments of the methods, the cancer is triple negative breast cancer.

BRIEF DESCRIPTION OF DRAWINGS

FIG. 3.1a and FIG. 3.1b show chemical structures of fourteen compounds (1-14) containing chloro, methylsulfonyl, methylthio, methoxy, methylenedioxy, piperazine, pyrrolidine, morpholine, piperidine, and nitrogen mustard chemical moieties.

FIG. 3.2 shows key COSY and HMBC correlations of compound 14.

FIG. 3.3 shows effect of compounds 13 and 14 on MDA-MB-231 cell morphology at 10 μM concentration (MDA-MB-231 is a known triple negative cell line). DMSO was used as a negative control. Panels A and B show images taken at a magnification scale of 10× and a diameter of 100 µm following 24 hours and 48 hours of treatment (N=4), respectively.

FIG. 3.4 shows effect of compounds 13 and 14 on MDA-MB-468 cell morphology at 10 µM (MDA-MB-468 is a known triple negative cell line). DMSO was used as a negative control. Panels A and B show images taken at a magnification scale of 10× and a diameter of 100 µm following 24 hours and 48 hours of treatment (N=4), respectively.

FIG. 3.5 shows the effect of compounds 13 and 14 on MCF-7 cell morphology at 10 µM (MCF-7 is not a triple negative cell line). DMSO was used as a negative control. Panels A and B show images taken at a magnification scale of 10× and a diameter of 100 µm following 24 hours and 48 hours of treatment (N=4), respectively.

FIG. 3.6 shows the effect of compounds 13 and 14 on HNME-E6\E7 cell morphology at 10 µM (HNME-E6/E7 is a normal human mammary epithelial cell line, immortalized by E6/E7 of high risk HPV type 16, which was used as a control). DMSO was used as a negative control. Images were taken at a magnification scale of 10× and a diameter of 100 µm following 48 hours of treatment (N=4).

FIG. 3.7 shows the effect of compounds 13 and 14 on colony formation of MDA-MB-231 cells. Results were obtained at 21 days post treatment with 5 and 10 µM of the compound. DMSO was used as a negative control; colchicine and paclitaxel were used as positive controls. Panel A shows microscopic pictures of the colonies; Panel B shows the number of colonies (>3-5 cells) were counted manually and were expressed as percentage of treatment relative to the control (Mean±SEM; n=3×3). One-way ANOVA followed by Tukey's post-hoc tests were used to compare treated versus untreated groups and *statistical significance was indicated when P-value <0.05 was achieved.

FIG. 3.8 shows the effect of compounds 13 and 14 on colony formation of MDA-MB-468 cells. Results were obtained at 14 days post treatment with 5 and 10 µM of the compound. DMSO was used as a negative control; colchicine and paclitaxel were used as positive controls. Panel A shows microscopic pictures of the colonies; Panel B shows the number of colonies (>3-5 cells) were counted manually and were expressed as percentage of treatment relative to the control (Mean±SEM; n=3×3). One-way ANOVA followed by Tukey's post-hoc tests were used to compare treated versus untreated groups and *statistical significance was indicated when P-value <0.05 was achieved.

FIG. 3.9 shows effects of compounds 13 and 14 on colony formation of MCF-7 cells. Results were obtained at 14 days post treatment after treatment with 5 and 10 µM of the compound. DMSO was used as a negative control; colchicine and paclitaxel were used as positive controls. Panel A shows microscopic pictures of the colonies; Panel B shows the number of colonies (>3-5 cells) were counted manually and were expressed as percentage of treatment relative to the control (Mean±SEM; n=3×3). One-way ANOVA followed by Tukey's post-hoc tests were used to compare treated versus untreated groups and *statistical significance was indicated when P-value <0.05 was achieved.

FIG. 3.10 shows Annexin V binding assay conducted on MDA-MB-468 cell line. Cells were incubated with PE Annexin V and 7-Amino-Actinomycin (7-AAD) and analyzed with Accuri C6 flow cytometer. Panel A shows flow cytometry showing forward (FSC) and side scatter (SSC) for MDA-MB-468 cell line, Panel B shows results at 24 and 48 hours post treatment with compound 14 (8 µM) compared to the vehicle DMSO and control. Viable cells are in the lower left quadrant, early apoptotic cells in the lower right quadrant, dead cells in the upper right quadrant, and necrotic cells in the upper left quadrant (N=1).

FIG. 3.11 shows the effect of compound 14 on BAX/bcl2 expression in MDA-MB-231 cell line. Panel A shows western blots representing protein expressions in the MDA-MB-231 cells treated with DMSO as a negative control, colchicine as a positive control, compound 14 at 5 µM and 10 µM concentrations. Panel B shows quantification of protein expression in comparison with the DMSO control. Values were normalized based on the expression of housekeeping protein β-actin. The results are presented as Mean±SEM (N=3). One-way ANOVA followed by Tukey's post-hoc tests were used to compare treated versus untreated groups and *statistical significance was indicated when P-value <0.05 was achieved. Colchi=Colchicine.

FIG. 3.12 shows the effect of compound 14 on BAX/bcl2 expression in MCF-7 cell line. Panel A shows western blots representing protein expressions in MDA-MB-231 cells treated with DMSO as a negative control, colchicine as a positive control, compound 14 at 5 µM and 10 µM concentrations. Panel B shows quantification of protein expression in comparison with the DMSO control. Values were normalized based on the expression of housekeeping protein β-actin. The results are presented as Mean±SEM (N=3). One-way ANOVA followed by Tukey's post-hoc tests were used to compare the treatment groups and *statistical significance was indicated when P-value <0.05 compared to the control. Colchi=Colchicine.

FIG. 3.13 shows flow cytometric analysis of cell cycle phases on MDA-MB-231. Cells were incubated for 48 h with 10 µM of compound 13 and 5 µM of compound 14, colchicine and paclitaxel. Cells were stained with propidium iodide (PI). Panel A shows flow cytometry showing forward (FSC) and side scatter (SSC) for MDA-MB-231 cell line, Panel B shows single cells were then gated based on their area and height on the forward scatter to exclude doublets. Panel C shows each histogram presents cells percentages in G1\G0, S, and G2/M phases. Panel D shows quantification of the three phases is presented as the Mean±SEM (N=3). One-way ANOVA followed by Tukey's post-hoc tests were used to compare the treatment groups and *statistical significance was indicated when P-value <0.05 compared to the control.

FIG. 3.14 shows flow cytometric analysis of cell cycle phases on MDA-MB-468. Cells were incubated for 48 h with 10 µM of compound 13 and 5 µM of compound 14, colchicine and paclitaxel. Cells were stained with propidium iodide (PI). Panel A shows flow cytometry showing forward (FSC) and side scatter (SSC) for MDA-MB-468 cell line, Panel B shows single cells were then gated based on their area and height on the forward scatter to exclude doublets. Panel C shows each histogram represents cells percentages in G1\G0, S, and G2/M phases. Panel D shows quantification of the three phases are presented as the Mean±SEM (N=3). One-way ANOVA followed by Tukey's post-hoc tests were used to compare the treatment groups and *statistical significance was indicated when P-value <0.05 compared to the control.

FIG. 3.15 shows flow cytometric analysis of cell cycle phases on MCF-7. Cells were incubated for 48 h with 10 µM of compound 13 and 5 µM of compound 14, colchicine and paclitaxel. Cells were stained with propidium iodide (PI). Panel A shows flow cytometry showing forward (FSC) and side scatter (SSC) for MCF-7 cell line, Panel B shows single cells were then gated based on their area and height on the forward scatter to exclude doublets. Panel C shows each histogram represents cells percentages in G1\G0, S, and G2/M phases. Panel D shows quantification of the three phases presented as the Mean±SEM (N=3). One-way ANOVA followed by Tukey's post-hoc tests were used to compare the treatment groups and *statistical significance was indicated when P-value <0.05 compared to the control.

FIG. 3.16 shows flow cytometric analysis of cell cycle phases on MDA-MB-231. Panel A shows cell cycle phases of compounds 2, 5 and 9 at 10 µM concentration at 48 hours post treatment. Each histogram represents cells percentages in G1\G0, S, and G2/M phases. Panel B shows quantification of the three phases are presented as the Mean±SEM (N=1). One-way ANOVA followed by Tukey's post-hoc tests were used to compare the treatment groups and *statistical significance was indicated when P-value <0.05 compared to the control.

FIG. 3.17 shows cell Invasion of MDA-MB-231 cells at 24 hours post treatment with compounds 13 and 14. Panel A shows microscopic pictures were taken after 24 hours of treatment with compounds 13 (10 µM) and 14 (5 µM). Panel B shows the number of invaded cells were counted using ImageJ (n=2×2). One-way ANOVA followed by Tukey's post-hoc tests were used to compare the treatment groups and *statistical significance was indicated when P-value <0.05 compared to the control.

FIG. 3.18 shows cell Invasion of MDA-MB-468 cells at 24 hours post treatment with compounds 13 and 14. Panel A shows microscopic pictures were taken after 24 hours of treatment with compounds 13 (10 µM) and 14 (5 µM). Panel B shows the number of invaded cells were counted using ImageJ (n=2×2). One-way ANOVA followed by Tukey's post-hoc tests were used to compare the treatment groups and *statistical significance was indicated when P-value <0.05 compared to the control.

FIG. 3.19 shows cell Invasion of MCF-7 cells at 24 hours post treatment with compounds 13 and 14. Panel A shows microscopic pictures were taken after 24 hours of treatment with compounds 13 (10 µM) and 14 (5 µM). Panel B shows the number of invaded cells were counted using ImageJ (n=2×2). One-way ANOVA followed by Tukey's post-hoc tests were used to compare the treatment groups and *statistical significance was indicated when P-value <0.05 compared to the control.

FIG. 3.20 shows cell migration assay results of compounds 1-14 on MDA-MB-231 cell line. Images were taken at a magnification scale of 10× and a diameter of 100 µm following 24 hours of treatment with 5 µM of compounds 1-14 (N=2×2).

FIG. 3.21 shows MDA-MB-231 cell migration results of compound 14 following 24 hours of treatment with five different concentrations ranging between 1.25-10 µM. Panel A shows microscopic pictures were taken at a magnification scale of 10× and a diameter of 100 µm. Panel B shows cell migration at different concentrations was quantified based on the wound diameter at 24 hours minus the initial diameter calculated at 2 different areas. Results were expressed as Mean±SEM relative to the control. $IC_{50}$ values were calculated using non-linear regression test.

FIG. 3.22 shows MCF-7 cell migration results of compound 14 following 24 hours of treatment with five different concentrations ranging between 1.25-20 µM. Panel A shows microscopic pictures were taken at a magnification scale of 10× and a diameter of 100 µm. Panel B shows cell migration at different concentrations was quantified based on the wound area at 24 hours minus the initial time point area. Results were expressed as Mean±SEM relative to the control. $IC_{50}$ values were calculated using non-linear regression test.

FIG. 3.23 shows SK-BR-3 cell migration results of compound 14 following 48 hours of treatment with five different concentrations ranging between 1.25-20 µM (SK-BR-3 is not a TNBC cell line, it is a HER2 positive cell line). Panel A shows microscopic pictures were taken at a magnification scale of 10× and a diameter of 100 µm. Panel B shows cell migration at different concentrations was quantified based on the wound diameter at 24 hours minus the initial diameter calculated at 2 different areas. Results were expressed as Mean±SEM relative to the control. $IC_{50}$ values were calculated using non-linear regression test.

FIG. 3.24 shows the effect of compound 14 on the expression of Epithelial Mesenchymal Transition (EMT) markers in MDA-MB-231 cells. Panel A shows western blots representing protein expressions in cells treated with DMSO as a negative control, colchicine as a positive control, compound 14 at 5 µM and 10 µM concentrations. Panel B shows quantification of protein expression compared with the DMSO control. Values were normalized based on housekeeping protein β-actin. The results are presented as Mean±SEM (N=3). One-way ANOVA followed by Tukey's post-hoc tests were used to compare the treatment groups and *statistical significance was indicated when P-value <0.05 compared to the control. E-cadh=E-cadherin; Pan-cadh=Pan-cadherin; Colchi=Colchicine.

FIG. 3.25 shows the effect of compound 14 on the expression of EMT markers on MCF-7. Panel A shows western blots representing protein expressions in cells treated with DMSO as a negative control, colchicine as a positive control, compound 14 at 5 µM and 10 µM concentrations. Panel B shows quantification of protein expression compared with the DMSO control. Values were normalized based on the housekeeping protein β-actin. The results are presented as the Mean±SEM (N=3). One-way ANOVA followed by Tukey's post-hoc tests were used to compare the treatment groups and *statistical significance was indicated when P-value <0.05 compared to the control. E-cadh=E-cadherin; Pan-cadh=Pan-cadherin; Colchi=Colchicine.

FIG. 3.26 shows the effect of compound 14 on Tubulin. Panel A shows 2D binding mode of compound 14 at the colchicine binding site of tubulin (PDB code: 5LYJ). Panel B shows effect of compound 14 on tubulin polymerization as compared to colchicine and paclitaxel (N=1×2).

FIG. 3.27 shows effects of compounds 5, 13 and 14 on blood vessels formation on the Chorioallantoic membrane (CAM) of the chicken embryos after 4 days of treatment with 2 µl of 5 µM stock solutions. Panel A shows representative pictures of different treatment groups (n=5-7). The treatments were placed under the coverslips. Panel B shows images of embryos at embryonic day 8 showing distribution of the blood vessels on embryos treated with compounds 13, 14 and DMSO. Panel C shows quantification of blood vessels under the coverslips relative to the untreated area on the CAM. Results are expressed as mean±SEM (n=5-6); One-way ANOVA followed by Tukey's post-hoc tests were used to compare the treatment groups and *statistical significance was indicated when P-value was <0.05 compared to the control.

FIG. 3.28 shows the effect of compound 14 on MDA-MB-231 xenografted nude mice. Panel A shows samples of treated (15 mg/kg, i.p. 3×/week) and untreated mice and their tumors at 45 days. Panel B shows tumor weight (gm) of treated vs control mice expressed as mean±SEM (n=5)

Figure 1:
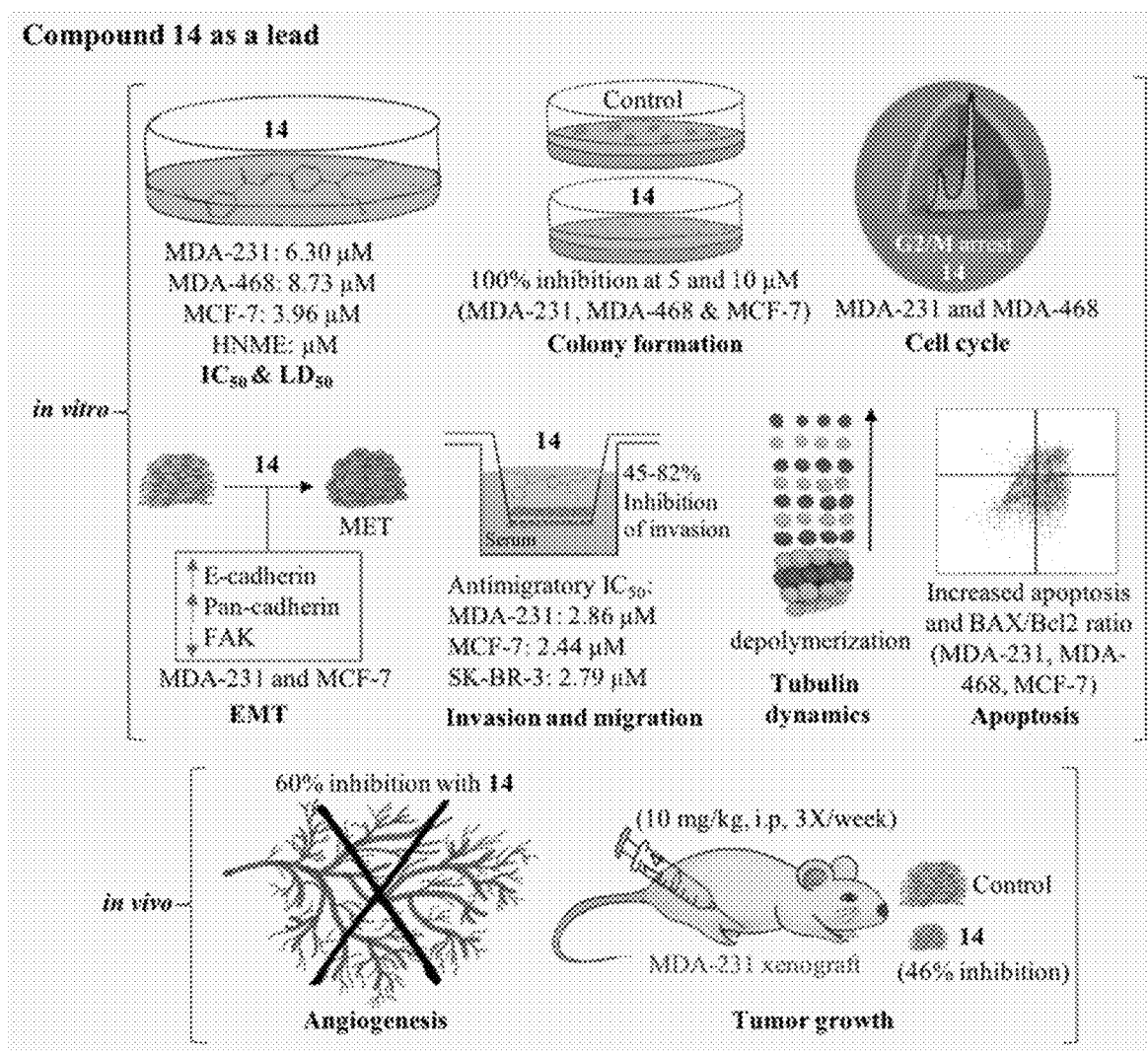
FIG. 1 shows a flow chart of investigation by the present inventors using compound 14 as an example.

calculated using student's t-test and *statistical significance was indicated when P-value <0.05. Panel C shows changes in tumor volume (mean±SEM) computed using student's t-test and *statistical significance is indicated when P-value <0.05. Panel D shows time of tumor appearance in each mouse. Panel E shows weight changes in the groups during course of the experiment. Panel F shows Kaplan-Meier survival analysis of control and treatment groups.

FIG. 4.1 shows LCMS mass spectrum confirming the presence of compound 14 molecular ion peak.

FIG. 4.2 shows FT-IR analysis confirming the presence of compound 14 functional groups.

FIG. 4.3 shows $^1$H-NMR spectra of compound 14 in $CDCl_3$.

FIG. 4.4 shows $^{13}$C-NMR spectra of compound 14 in $CDCl_3$.

FIG. 4.5 shows Correlation Spectroscopy (COSY) of compound 14 in $CDCl_3$.

FIG. 4.6 shows Heteronuclear Multiple Bond Correlation (HMBC) of compound 14 in $CDCl_3$.

FIG. 4.7 shows Heteronuclear Multiple Quantum Correlation (HMQC) of compound 14 in $CDCl_3$.

DETAILED DESCRIPTION

Generally, the nomenclature used herein and the laboratory procedures in organic chemistry, medicinal chemistry, and pharmacology described herein are those well-known and commonly employed in the art. Unless defined otherwise, all technical and scientific terms used herein generally have the same meaning as commonly understood by one of ordinary skill in the art to which this disclosure belongs. In the event that there is a plurality of definitions for a term used herein, those in this section prevail unless stated otherwise.

The term "subject" as used herein refers to an animal, including, but not limited to, a primate (e.g., human), cow, sheep, goat, horse, dog, cat, rabbit, rat, or mouse. The terms "subject" and "patient" may be used interchangeably herein in reference, for example, to a mammalian subject, such as a human subject.

The terms "treat," "treating," and "treatment" as used herein are meant to include alleviating or abrogating a disorder, disease, or condition, or one or more of the symptoms associated with the disorder, disease, or condition; or alleviating or eradicating the cause(s) of the disorder, disease, or condition itself.

The terms "prevent," "preventing," and "prevention" as used herein are meant to include a method of delaying and/or precluding the onset of a disorder, disease, or condition, and/or its attendant symptoms; barring a subject from acquiring a disease; or reducing a subject's risk of acquiring a disorder, disease, or condition.

The term "therapeutically effective amount" as used herein is meant to include the amount of a compound that, when administered, is sufficient to prevent development of, or alleviate to some extent, one or more of the symptoms of the disorder, disease, or condition being treated. The term "therapeutically effective amount" also refers to the amount of a compound that is sufficient to elicit the biological or medical response of a cell, tissue, system, animal, or human, which is being sought by a researcher, veterinarian, medical doctor, or clinician. In some instances, the term may be used interchangeably with the term "effective amount."

The term "about" or "approximately" as used herein means an acceptable error for a particular value as determined by one of ordinary skill in the art, which depends in part on how the value is measured or determined. In certain embodiments, the term "about" or "approximately" means within 1, 2, 3, or 4 standard deviations. In certain embodiments, the term "about" or "approximately" means within 50%, 20%, 15%, 10%, 9%, 8%, 7%, 6%, 5%, 4%, 3%, 2%, 1%, 0.5%, or 0.05% of a given value or range.

The terms "active ingredient" and "active substance" as used herein refer to a compound, which is administered, alone or in combination with one or more pharmaceutically acceptable excipients, to a subject for treating, preventing, or ameliorating one or more symptoms of a disorder or disease. As used herein, "active ingredient" and "active substance" may be a salt, solvate, or prodrug of a compound described herein.

The terms "drug," "therapeutic agent," and "chemotherapeutic agent" as used herein refer to a compound or a pharmaceutical composition thereof, which is administered to a subject for treating, preventing, or ameliorating one or more symptoms of a condition, disorder, or disease.

The term "pharmaceutically acceptable salt" as used herein refers to any salt suitable for administration to a patient. The term "salt" refers to any salt of a compound provided herein. Such salts may be derived from a variety of organic and inorganic counter-ions well known in the art. Such salts include, but are not limited to: (1) acid addition salts formed with organic or inorganic acids such as hydrochloric, hydrobromic, sulfuric, nitric, phosphoric, sulfamic, acetic, trifluoroacetic, trichloroacetic, propionic, hexanoic, cyclopentylpropionic, glycolic, glutaric, pyruvic, lactic, malonic, succinic, sorbic, ascorbic, malic, maleic, fumaric, tartaric, citric, benzoic, 3-(4-hydroxybenzoyl)benzoic, picric, cinnamic, mandelic, phthalic, lauric, methanesulfonic, ethanesulfonic, 1,2-ethane-disulfonic, 2-hydroxyethanesulfonic, benzenesulfonic, 4-chlorobenzenesulfonic, 2-naphthalenesulfonic, 4-toluenesulfonic, camphoric, camphorsulfonic, 4-methylbicyclo[2.2.2]-oct-2-ene-1-carboxylic, glucoheptonic, 3-phenylpropionic, trimethylacetic, tert-butylacetic, lauryl sulfuric, gluconic, benzoic, glutamic, hydroxynaphthoic, salicylic, stearic, cyclohexylsulfamic, quinic, muconic acid and the like acids; or (2) base addition salts formed when an acidic proton present in the parent compound either (a) is replaced by a metal ion, e.g., an alkali metal ion, an alkaline earth ion or an aluminum ion, or alkali metal or alkaline earth metal hydroxides, such as sodium, potassium, calcium, magnesium, aluminum, lithium, zinc, and barium hydroxide, ammonia or (b) coordinates with an organic base, such as aliphatic, alicyclic, or aromatic organic amines, such as ammonia, methylamine, dimethylamine, diethylamine, picoline, ethanolamine, diethanolamine, triethanolamine, ethylenediamine, lysine, arginine, ornithine, choline, N,N'-dibenzylethylene-diamine, chloroprocaine, diethanolamine, procaine, N-benzylphenethylamine, N-methylglucamine piperazine, tris(hydroxymethyl)-aminomethane, tetramethylammonium hydroxide, and the like.

Salts further include, by way of example only and without limitation, sodium, potassium, calcium, magnesium, ammonium, tetraalkylammonium and the like, and when the compound contains a basic functionality, salts of non-toxic organic or inorganic acids, such as hydrohalides, e.g. hydrochloride and hydrobromide, sulfate, phosphate, sulfamate, nitrate, acetate, trifluoroacetate, trichloroacetate, propionate, hexanoate, cyclopentylpropionate, glycolate, glutarate, pyruvate, lactate, malonate, succinate, sorbate, ascorbate, malate, maleate, fumarate, tartarate, citrate, benzoate, 3-(4-hydroxybenzoyl)benzoate, picrate, cinnamate, mandelate, phthalate, laurate, methanesulfonate (mesylate), ethanesulfonate, 1,2-ethane-disulfonate, 2-hydroxyethanesulfonate, benzenesulfonate (besylate), 4-chlorobenzenesulfonate, 2-naphthalenesulfonate, 4-toluenesulfonate, camphorate, camphorsulfonate, 4-methylbicyclo[2.2.2]-oct-2-ene-1-carboxylate, glucoheptonate, 3-phenylpropionate, trimethylacetate, tert-butylacetate, lauryl sulfate, gluconate, benzoate, glutamate, hydroxynaphthoate, salicylate, stearate, cyclohexylsulfamate, quinate, muconate and the like.

The term "pharmaceutically acceptable solvate" as used herein refers to any solvate suitable for administration to a patient. The term "solvate" refers to a complex that forms between a solute and its solvent. The solute is a compound provided herein. The solvents include, but are not limited to, water, methanol, ethanol, propyl alcohol, butyl alcohol, acetone, dichloromethane, chloroform, 1,4-dioxane, tetrahydrofuran, ethyl acetate, dimethyl sulfoxide, or dimethylformamide.

The term "alkyl" as used herein refers to a linear or branched saturated monovalent hydrocarbon radical. The term "alkyl" also encompasses both linear and branched alkyl, unless otherwise specified. In certain embodiments, the alkyl is a linear saturated monovalent hydrocarbon radical that has 1 to 20 ($C_{1-20}$), 1 to 15 ($C_{1-5}$), 1 to 10 ($C_{1-10}$), 1 to 6 ($C_{1-6}$), 1 to 5 ($C_{1-5}$), 1 to 4 ($C_{1-4}$), or 1 to 3 ($C_{1-3}$) carbon atoms, or branched saturated monovalent hydrocarbon radical of 3 to 20 ($C_{3-20}$), 3 to 15 ($C_{3-15}$), 3 to 10 ($C_{3-10}$), or 3 to 6 ($C_{3-6}$) carbon atoms. In certain embodiments, the alkyl is a linear or branched saturated monovalent hydrocarbon radical that has at least 1, 2, 3, 4, 5, 6, 7, 8, 9, or 10 carbon atoms. Examples of alkyl groups include, but are not limited to, methyl, ethyl, propyl (including all isomeric forms), n-propyl, isopropyl, butyl (including all isomeric forms), n-butyl, isobutyl, t-butyl, pentyl (including all isomeric forms), and hexyl (including all isomeric forms). For example, $C_{1-6}$ alkyl refers to a linear saturated monovalent hydrocarbon radical of 1 to 6 carbon atoms or a branched saturated monovalent hydrocarbon radical of 3 to 6 carbon atoms.

The term "alkyl" as used throughout the specification and claims is intended to include both "unsubstituted alkyls" and "substituted alkyls", the later denotes an alkyl radical analogous to the above definition that is further substituted with one, two, or more additional organic or inorganic substituent groups. Suitable substituent groups include but are not limited to hydroxyl, cycloalkyl, amino, mono-substituted amino, di-substituted amino, unsubstituted or substituted amido, carbonyl, halogen, sulfhydryl, sulfonyl, sulfonato, sulfamoyl, sulfonamide, azido, acyloxy, nitro, cyano, carboxy, carboalkoxy, alkylcarboxamido, substituted alkylcarboxamido, dialkylcarboxamido, substituted dialkylcarboxamido, alkylsulfonyl, alkylsulfinyl, thioalkyl, thiohaloalkyl, alkoxy, substituted alkoxy, haloalkoxy, heteroaryl, substituted heteroaryl, aryl or substituted aryl. It will be understood by those skilled in the art that an "alkoxy" can be a substituted of a carbonyl substituted "alkyl" forming an ester. When more than one substituent group is present then they can be the same or different. The organic substituent moieties can comprise from 1 to 12 carbon atoms, or from 1 to 6 carbon atoms, or from 1 to 4 carbon atoms. It will be understood by those skilled in the art that the moieties substituted on the "alkyl" chain can themselves be substituted, as described above, if appropriate.

The term "halogen," "halide," or "halo" as used herein refers to fluorine, chlorine, bromine, or iodine. The term "halo," "halide," or "halogen" as used herein also refers to a fluoro, chloro, bromo or iodo.

The term "haloalkyl" as used herein refers to an alkyl residue as defined above, substituted with one or more halogens, such as monofluoromethyl, difluoromethy, or trifluoromethyl; monochloromethyl, dichloromethy, or trichloromethyl; and the like.

The term "alkoxy" or "alkoxyl" as used herein refers to an alkyl residue, as defined above, bonded directly to an oxygen atom, which is then bonded to another moiety. Examples include methoxy, ethoxy, n-propoxy, iso-propoxy, n-butoxy, t-butoxy, iso-butoxy and the like. An "alkoxy" group may be defined as —OR where R is alkyl as defined above.

The term "thio" as used herein refers to group defined as —SH.

The term "alkylthio" as used herein refers to an alkyl residue, as defined above, bonded directly to a sulfur atom, which is then bonded to another moiety. An "alkylthio" group may be defined as —SR where R is alkyl as defined above.

The term "amino" as used herein refers to group defined as —$NH_2$ which may be mono- or bi-substituted. The term "mono-substituted amino" as used herein refers to a moiety comprising an NH radical substituted with one organic substituent group, which include but are not limited to alkyls, substituted alkyls, cycloalkyls, aryls, or arylalkyls. Examples of mono-substituted amino groups include methylamino (—$NHCH_3$), ethylamino (—$NHCH_2CH_3$), hydroxyethylamino (—$NHCH_2CH_2OH$), and the like. The term "di-substituted amino" as used herein is a moiety comprising a nitrogen atom substituted with two organic radicals that can be the same or different, which can be selected from but are not limited to aryl, substituted aryl, alkyl, substituted alkyl, and arylalkyl, wherein the terms have the same definitions found throughout. Some examples include dimethylamino, methylethylamino, diethylamino and the like.

The term "alkylamino" as used herein refers to an alkyl residue, as defined above, bonded directly to a nitrogen atom, which is then bonded to another moiety. An "alkyl amino" group may be defined as —$NR_1R_2$ where $R_1$ or/and $R_2$ are alkyl as defined above.

The term "heterocyclyl" or "heterocyclic" as used herein refers to a monocyclic or multicyclic non-aromatic ring system, wherein one or more of the ring atoms are heteroatoms independently selected from O, S, or N; and the remaining ring atoms are carbon atoms. In certain embodiments, the heterocyclyl or heterocyclic group has from 3 to 20, from 3 to 15, from 3 to 10, from 3 to 8, from 4 to 7, or from 5 to 6 ring atoms. Examples of heterocyclyl groups include, but are not limited to, pyrrolidinyl, piperidinyl, 2-oxopyrrolidinyl, 2-oxopiperidinyl, morpholinyl, piperazinyl, tetrahydropyranyl, and thiomorpholinyl. All such heterocyclic groups may also be optionally substituted, e.g., as described herein.

The term "heterocycle," "heterocyclyl," or "heterocyclic group" as used herein refers to a non-aromatic or aromatic mono- or multi-ring radical structure having 3 to 16 members, preferably 4 to 10 members, in which at least one ring structure include 1 to 4 heteroatoms (e.g. O, N, S, P, and the like). Heterocyclyl groups include but are not limited to, for example, pyrrolidine, oxolane, thiolane, imidazole, oxazole, piperidine, piperizine, morpholine, lactones, lactams, such as azetidiones, and pyrrolidiones, sultams, sultones, and the like. Moreover, the term "heterocyclyl" as used throughout the specification and claims may include both "unsubstituted" and "substituted" heterocyclyl, the later denotes a cyclic ring radical as defined above that is substituted with one or more, preferably 1, 2, or 3 organic substituent groups, which include but are not limited to a halogen, alkyl, alkenyl, alkynyl, hydroxyl, cycloalkyl, amino, mono-substituted amino, di-substituted amino, unsubstituted or substituted amido, carbonyl, halogen, sulfhydryl, sulfonyl, sulfonato, sulfamoyl, sulfonamide, azido acyloxy, nitro, cyano, carboxy, carboalkoxy, alkylcarboxarnlido, substituted aikylcarboxarnlido, di alkylcarboxamido, substituted dialkylcarboxamido, alkylsulfonyl, alkylsulfinyl, thioalkyl, thiohaloalkyl, alkoxy, substituted alkoxy or haloalkoxy, aryl, substituted aryl, heteroaryl, heterocyclic ring, ring wherein the terms are defined herein. The organic substituent groups can comprise from 1 to 12 carbon atoms, or from 1 to 6 carbon atoms; or from 1 to 4 carbon atoms. It will be understood by those skilled in the art that the moieties substituted on the "heterocyclyl" can themselves be substituted, as described above, if appropriate.

The term "optionally substituted" is intended to mean that a group, such as an alkyl, haloalkyl, alkoxy, alkylthio, alkylamino, cyclic group, or heterocyclyl group, may be substituted with one or more substituents independently selected from, e.g., halo, alkyl, alkenyl, alkynyl, cycloalkyl, aryl, heteroaryl, or heterocyclyl, each optionally substituted, e.g., as described herein. The group can be substituted with any described moiety, including, but not limited to, one or more moieties selected from the group consisting of halogen (fluoro, chloro, bromo, or iodo), hydroxyl, amino, alkylamino (e.g., monoalkylamino, dialkylamino, or trialkylamino), arylamino (e.g., monoarylamino, diarylamino, or triarylamino), alkoxy, aryloxy, nitro, cyano, sulfonic acid, sulfate, phosphonic acid, phosphate, or phosphonate, either unprotected or protected as necessary, as known to those skilled in the art. As used herein, all groups that can be substituted in one embodiment are "optionally substituted," unless otherwise specified.

The term "$IC_{50}$" refers the amount, concentration, or dosage of a compound that is required for 50% inhibition of a maximal response in an assay that measures such response.

The term "$EC_{50}$" refers to the amount, concentration, or dosage of a drug which induces a response halfway between the baseline and maximum after a specified exposure time. It is commonly used as a measure of a drug's potency.

The term "$LD_{50}$" or the median lethal dose is a measure of the lethal dose of a toxin, radiation, or pathogen. The value of $LD_{50}$ for a substance is the dose required to kill half the members of a tested population after a specified test duration. $LD_{50}$ figures are frequently used as a general indicator of a substance's acute toxicity. A lower $LD_{50}$ is indicative of increased toxicity.

Provided herein are compounds, compositions, and methods useful for the treatment of cancers, particularly breast cancers, and more particularly TNBCs.

Compounds

In certain aspects, provided herein are compounds of formula (I): (I), or a

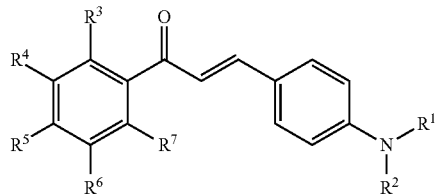

pharmaceutically acceptable salt or solvate thereof, wherein $R^1$ and $R^2$ are each independently haloalkyl; or $R^1$ and $R^2$ together with the N atom form a heterocyclic group;

$R^3$, $R^4$, $R^5$, $R^6$, and $R^7$ are each independently selected from hydrogen, halo, alkyl, hydroxyl, alkoxyl, amino, alkylamino, thio, alkylthio, sulfonyl, alkylsulfonyl, and heterocyclic group; or $R^3$ and $R^4$, or $R^4$ and $R^5$, or $R^5$ and $R^6$, or $R^6$ and $R^7$ form

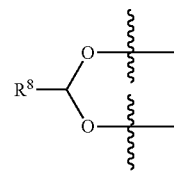

wherein "⌇" indicates point of attachment, wherein $R^8$ is hydrogen or alkyl, and the rest of $R^3$, $R^4$, $R^5$, $R^6$, and $R^7$ are each independent selected from hydrogen, halo, and alkyl.

In some embodiments including any foregoing embodiments, $R^1$ and $R^2$ are each independently haloalkyl. In some embodiments, the haloalkyl is chloroethyl. In some embodiments including any foregoing embodiments, $R^1$ and $R^2$ are each chloroethyl.

In some embodiments including any foregoing embodiments, $R^1$ and $R^2$ together with the N atom form a heterocyclic group. In some embodiments including any foregoing embodiments, $R^1$ and $R^2$ together with the N atom form a heterocyclic group selected from azetidyl, pyrrolidyl, piperidyl, azepanyl, piperazinyl, and morpholinyl. In some embodiments including any foregoing embodiments, $R^1$ and $R^2$ together with the N atom form a heterocyclic group selected from pyrrolidyl, piperidyl, and morpholinyl.

In some embodiments including any foregoing embodiments, $R^3$, $R^4$, $R^5$, $R^6$, and $R^7$ are each independently selected from hydrogen, halo, alkyl, hydroxyl, alkoxyl, amino, alkylamino, thio, alkylthio, sulfonyl, alkylsulfonyl, and heterocyclic group. In some embodiments including any foregoing embodiments, at least one of $R^3$, $R^4$, $R^5$, $R^6$, and $R^7$ is selected from halo, alkyl, hydroxyl, alkoxyl, amino, alkylamino, thio, alkylthio, sulfonyl, alkylsulfonyl, and heterocyclic group. In some embodiments including any foregoing embodiments, at least one of $R^3$, $R^4$, $R^5$, $R^6$, and $R^7$ is selected from halo, alkyl, hydroxyl, alkoxyl, amino, alkylamino, thio, alkylthio, sulfonyl, alkylsulfonyl, and heterocyclic group, the rest of $R^3$, $R^4$, $R^5$, $R^6$, and $R^7$ are each hydrogen.

In some embodiments including any foregoing embodiments, $R^3$, $R^4$, $R^5$, $R^6$, and $R^7$ are each independently selected from hydrogen, halo, alkoxyl, alkylamino, alkylthio, alkylsulfonyl, and heterocyclic group. In some embodiments including any foregoing embodiments, at least one of $R^3$, $R^4$, $R^5$, $R^6$, and $R^7$ is selected from halo, alkoxyl, alkylamino, alkylthio, alkylsulfonyl, and heterocyclic group. In some embodiments including any foregoing embodiments, at least one of $R^3$, $R^4$, $R^5$, $R^6$, and $R^7$ is selected from halo, alkoxyl, alkylamino, alkylthio, alkylsulfonyl, and heterocyclic group, the rest of $R^3$, $R^4$, $R^5$, $R^6$, and $R^7$ are each hydrogen.

In some embodiments including any foregoing embodiments, the halo is chloro; the alkylsufonyl is methylsulfonyl; the alkylthio is methylthio; the alkoxy is methoxy; the heterocyclic group is piperazinyl, pyrrolidyl, morpholinyl, or piperidyl, In some embodiments including any foregoing embodiments, one of $R^3$, $R^4$, $R^5$, $R^6$, and $R^7$ is independent selected from chloro, methylsulfonyl, methylthio, methoxy, piperazinyl, pyrrolidyl, morpholinyl, and piperidyl, the rest of $R^3$, $R^4$, $R^5$, $R^6$, and $R^7$ are each hydrogen.

In some embodiments including any foregoing embodiments, one of $R^3$, $R^4$, $R^5$, $R^6$, and $R^7$ is chloro, the rest of $R^3$, $R^4$, $R^5$, $R^6$, and $R^7$ are each hydrogen.

In some embodiments including any foregoing embodiments, one of $R^3$, $R^4$, $R^5$, $R^6$, and $R^7$ is methoxy, the rest of $R^3$, $R^4$, $R^5$, $R^6$, and $R^7$ are each hydrogen.

In some embodiments including any foregoing embodiments, one of $R^3$, $R^4$, $R^5$, $R^6$, and $R^7$ is methylthio, the rest of $R^3$, $R^4$, $R^5$, $R^6$, and $R^7$ are each hydrogen.

In some embodiments including any foregoing embodiments, one of $R^3$, $R^4$, $R^5$, $R^6$, and $R^7$ is methylsulfonyl, the rest of $R^3$, $R^4$, $R^5$, $R^6$, and $R^7$ are each hydrogen.

In some embodiments including any foregoing embodiments, one of $R^3$, $R^4$, $R^5$, $R^6$, and $R^7$ is piperazinyl, the rest of $R^3$, $R^4$, $R^5$, $R^6$, and $R^7$ are each hydrogen.

In some embodiments including any foregoing embodiments, $R^3$ and $R^4$, or $R^4$ and $R^5$, or $R^5$ and $R^6$, or $R^6$ and $R^7$ form a group

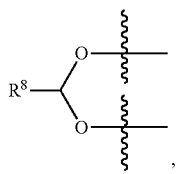

wherein " $\sim$ " indicates point of attachment, wherein $R^8$ is hydrogen or alkyl, and the rest of $R^3$, $R^4$, $R^5$, $R^6$, and $R^7$ are each independent selected from hydrogen, halo, and alkyl. In some embodiments including any foregoing embodiments, $R^3$ and $R^4$ form

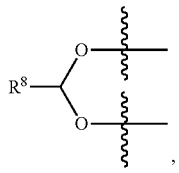

and $R^5$, $R^6$, and $R^7$ are each independent selected from hydrogen, halo, and alkyl. In some embodiments including any foregoing embodiments, $R^4$ and $R^5$ form

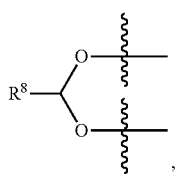

and $R^3$, $R^6$, and $R^7$ are independent selected from hydrogen, halo, and alkyl. In some embodiments including any foregoing embodiments, $R^5$ and $R^6$ form

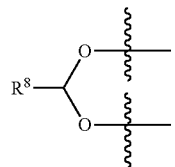

and $R^3$, $R^4$, and $R^7$ are independent selected from hydrogen, halo, and alkyl. In some embodiments including any foregoing embodiments, $R^6$ and $R^7$ form

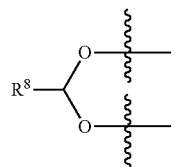

and $R^3$, $R^4$, and $R^5$ are independent selected from hydrogen, halo, and alkyl. In some embodiments including any foregoing embodiments, $R^3$ and $R^4$, or $R^4$ and $R^5$, or $R^5$ and $R^6$, or $R^6$ and $R^7$ form a group form

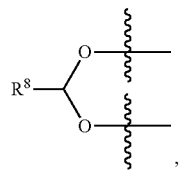

and the rest of $R^3$, $R^4$, $R^5$, $R^6$, and $R^7$ are each hydrogen.

In some embodiments including any foregoing embodiments, $R^4$ and $R^5$ form

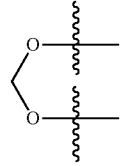 [SMILES: *OCO*]

("methylenedioxy") wherein " $\sim$ " indicates point of attachment, and $R^3$, $R^6$, and $R^7$ are each hydrogen.

In some embodiments including any foregoing embodiments, the compound is any one of the following:

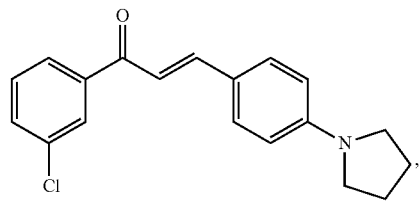

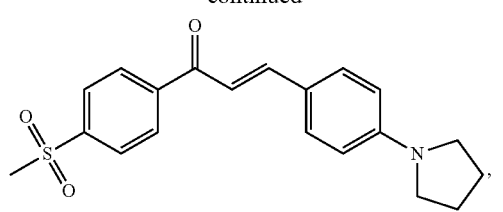
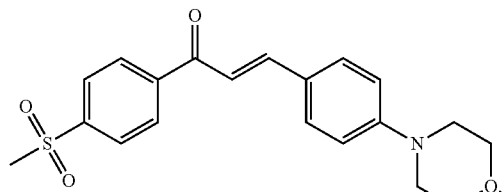
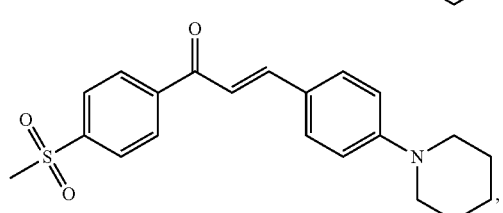
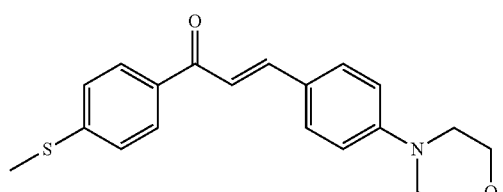
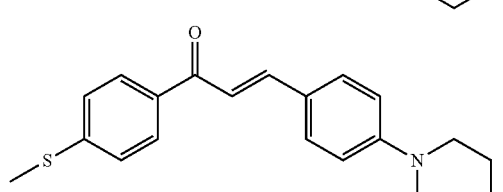
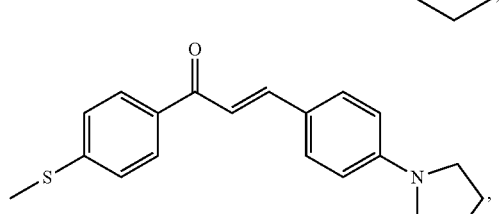
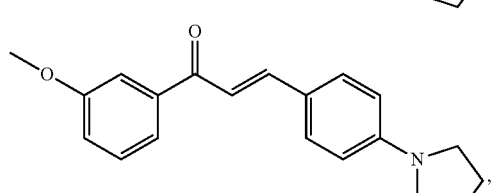
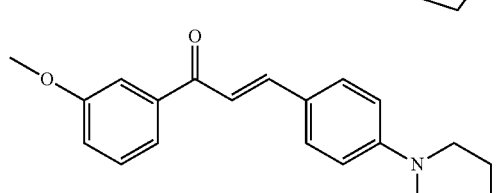
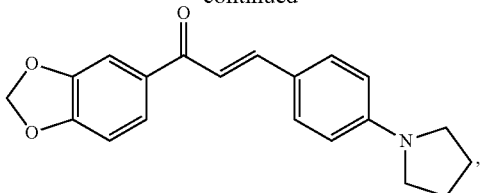
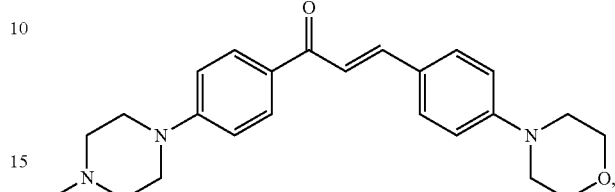
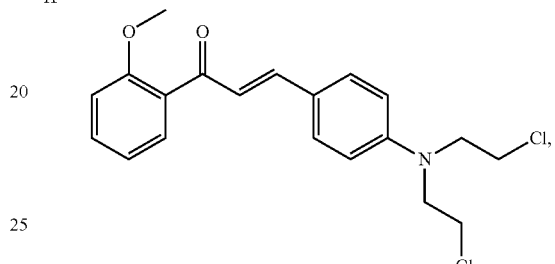
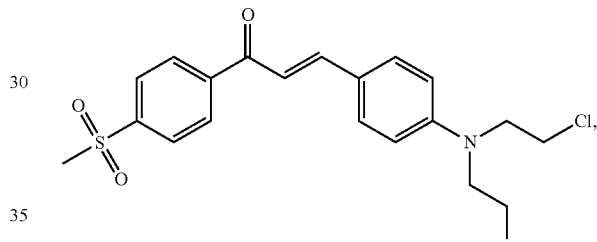
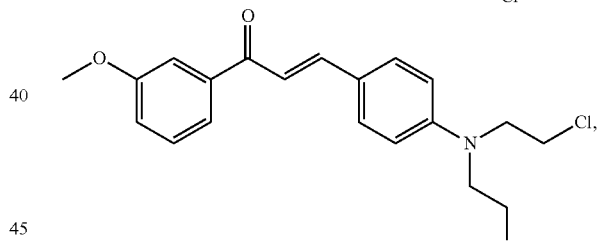
or a pharmaceutically acceptable salt or solvate thereof.
In some embodiments including any foregoing embodiments, the compound is
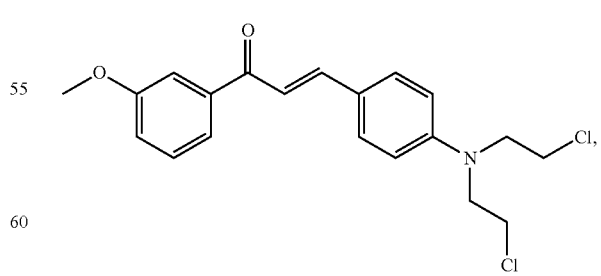
or a pharmaceutically acceptable salt or solvate thereof.
Compounds provided herein are useful for the treatment of cancers, particularly breast cancers, and more particularly triple negative breast cancers (TNBCs).

Compositions or Formulations

In certain aspects, provided herein are compositions comprising any of the compounds described above or provided herein. In some embodiments, the composition is a pharmaceutical composition comprising any of the compounds described above or provided herein and a pharmaceutically acceptable carrier and/or excipient.

The compositions or pharmaceutical compositions provided herein are useful for the treatment of breast cancer, particularly TNBCs.

In a specific embodiment and in this context, the term "pharmaceutically acceptable" means approved by a regulatory agency of the federal or a state government or listed in the U.S. Pharmacopeia or other generally recognized pharmacopeia for use in animals, and more particularly in humans. The term "carrier" includes a diluent, adjuvant (e.g., Freund's adjuvant (complete and incomplete), excipient, or vehicle with which the therapeutic is administered.

The term "carrier" refers to a substance used in the process of drug delivery which serves to improve the selectivity, effectiveness, and/or safety of drug administration. Drug carriers are primarily used to control the release of a drug into systemic circulation. This can be accomplished either by slow release of the drug over a long period of time or by triggered release at the drug's target by some stimulus, such as changes in pH, application of heat, and activation by light. Drug carriers are also used to improve the pharmacokinetic properties, specifically the bioavailability, of many drugs with poor water solubility and/or membrane permeability. The term "excipient" refers to a substance that serves as the vehicle or medium for a drug or other active substance, or a substance formulated alongside the active ingredient of a medication included for the purpose of long-term stabilization, bulking up solid formulations that contain potent active ingredients in small amounts (thus often referred to as "bulking agents," "fillers," or "diluents"), or to confer a therapeutic enhancement on the active ingredient in the final dosage form, such as facilitating drug absorption, reducing viscosity, or enhancing solubility. A pharmaceutical excipient is a substance other than the active pharmaceutical ingredient (API) that have been appropriately evaluated for safety and are intentionally included in a drug delivery system. Generally, a carrier or excipient has no medicinal properties.

In some embodiments, pharmaceutically acceptable or pharmaceutical carriers can be sterile liquids, such as water and oils, including those of petroleum, animal, vegetable or synthetic origin, such as peanut oil, soybean oil, mineral oil, sesame oil and the like. Water can be used as a carrier when the pharmaceutical composition is administered intravenously. Saline solutions and aqueous dextrose and glycerol solutions can also be employed as liquid carriers, particularly for injectable solutions. Examples of suitable pharmaceutical carriers are described in "Remington's Pharmaceutical Sciences" by E.W. Martin.

Typical pharmaceutical compositions and dosage forms comprise one or more excipients. Suitable excipients are well-known to those skilled in the art of pharmacy, and non-limiting examples of suitable excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. Whether a particular excipient is suitable for incorporation into a pharmaceutical composition or dosage form depends on a variety of factors well known in the art including, but not limited to, the way in which the dosage form will be administered to a subject and the specific active ingredients in the dosage form. The composition or single unit dosage form, if desired, can also contain minor amounts of wetting or emulsifying agents, or pH buffering agents.

The compositions provided herein can be formulated as pharmaceutical compositions or formulations using methods available in the art and those disclosed herein. Any of the compositions disclosed herein can be provided in the appropriate pharmaceutical formulation and be administered by a suitable route of administration.

In clinical practice the compositions provided herein may be administered by any conventional route, in particular orally, parenterally, rectally, or by inhalation (e.g. in the form of aerosols). In certain embodiments, the compositions provided herein are administered orally.

In certain embodiments, the compositions provided herein are solid compositions for oral administration, of tablets, pills, hard gelatin capsules, powders or granules. In these compositions, the active product is mixed with one or more inert diluents or adjuvants, such as sucrose, lactose or starch. These compositions can comprise substances other than diluents, for example a lubricant, such as magnesium stearate, or a coating intended for controlled release.

In certain embodiments, the compositions provided herein are liquid compositions for oral administration, which are pharmaceutically acceptable solutions, suspensions, emulsions, syrups and elixirs containing inert diluents, such as water or liquid paraffin. These compositions can also comprise substances other than diluents, for example wetting, sweetening or flavoring products.

The compositions for parenteral administration can be emulsions or sterile solutions. Use may be made, as solvent or vehicle, of propylene glycol, a polyethylene glycol, vegetable oils, in particular olive oil, or injectable organic esters, for example ethyl oleate. These compositions can also contain adjuvants, in particular wetting, isotonizing, emulsifying, dispersing and stabilizing agents. Sterilization can be carried out in several ways, for example using a bacteriological filter, by radiation or by heating. They can also be prepared in the form of sterile solid compositions which can be dissolved at the time of use in sterile water or any other injectable sterile medium.

The compositions for rectal administration are suppositories or rectal capsules which contain, in addition to the active principle, excipients such as cocoa butter, semi-synthetic glycerides or polyethylene glycols.

In some embodiments, the compositions can also be aerosols. For use in the form of liquid aerosols, the compositions can be stable sterile solutions or solid compositions dissolved at the time of use in apyrogenic sterile water, in saline or any other pharmaceutically acceptable vehicle. For use in the form of dry aerosols intended to be directly inhaled, the active principle is finely divided and combined with a water-soluble solid diluent or vehicle, for example dextran, mannitol or lactose.

In certain embodiments, a composition provided herein is a pharmaceutical composition or a single unit dosage form. Pharmaceutical compositions and single unit dosage forms provided herein comprise a prophylactically or therapeutically effective amount of one or more prophylactic or therapeutic agents (e.g., a compound provided herein, or other prophylactic or therapeutic agent), and a typically one or more pharmaceutically acceptable carriers or excipients.

Further encompassed herein are anhydrous pharmaceutical compositions and dosage forms comprising active ingredients, since water can facilitate the degradation of some compounds. Anhydrous pharmaceutical compositions and dosage forms provided herein can be prepared using anhydrous or low moisture containing ingredients and low moisture or low humidity conditions. Pharmaceutical compositions and dosage forms that comprise lactose and at least one active ingredient that comprises a primary or secondary amine can be anhydrous if substantial contact with moisture and/or humidity during manufacturing, packaging, and/or storage is expected. An anhydrous pharmaceutical composition should be prepared and stored such that its anhydrous nature is maintained. Accordingly, anhydrous compositions can be packaged using materials known to prevent exposure to water such that they can be included in suitable formulary kits. Further provided are pharmaceutical compositions and dosage forms that comprise one or more compounds that reduce the rate by which an active ingredient will decompose. Such compounds, which are referred to herein as "stabilizers," include, but are not limited to, antioxidants such as ascorbic acid, pH buffers, or salt buffers.

The pharmaceutical compositions and single unit dosage forms can take the form of solutions, suspensions, emulsion, tablets, pills, capsules, powders, sustained-release formulations and the like. Oral formulation can include standard carriers such as pharmaceutical grades of mannitol, lactose, starch, magnesium stearate, sodium saccharine, cellulose, magnesium carbonate, etc. Such compositions and dosage forms will contain a prophylactically or therapeutically effective amount of a prophylactic or therapeutic agent, in certain embodiments, in purified form, together with a suitable amount of carrier so as to provide the form for proper administration to the subject. The formulation should suit the mode of administration. In a certain embodiment, the pharmaceutical compositions or single unit dosage forms are sterile and in suitable form for administration to a subject, for example, an animal subject, such as a mammalian subject, for example, a human subject.

A pharmaceutical composition is formulated to be compatible with its intended route of administration. Examples of routes of administration include, but are not limited to, parenteral, e.g., intravenous, intradermal, subcutaneous, intramuscular, subcutaneous, oral, buccal, sublingual, inhalation, intranasal, transdermal, topical, transmucosal, intratumoral, intra-synovial and rectal administration. In a specific embodiment, the composition is formulated in accordance with routine procedures as a pharmaceutical composition adapted for intravenous, subcutaneous, intramuscular, oral, intranasal or topical administration to human beings. In an embodiment, a pharmaceutical composition is formulated in accordance with routine procedures for subcutaneous administration to human beings. Typically, compositions for intravenous administration are solutions in sterile isotonic aqueous buffer. Where necessary, the composition may also include a solubilizing agent and a local anesthetic such as lignocamne to ease pain at the site of the injection.

Examples of dosage forms include, but are not limited to: tablets; caplets; capsules, such as soft elastic gelatin capsules; cachets; troches; lozenges; dispersions; suppositories; ointments; cataplasms (poultices); pastes; powders; dressings; creams; plasters; solutions; patches; aerosols (e.g., nasal sprays or inhalers); gels; liquid dosage forms suitable for oral or mucosal administration to a subject, including suspensions (e.g., aqueous or non-aqueous liquid suspensions, oil in water emulsions, or a water in oil liquid emulsions), solutions, and elixirs; liquid dosage forms suitable for parenteral administration to a subject; and sterile solids (e.g., crystalline or amorphous solids) that can be reconstituted to provide liquid dosage forms suitable for parenteral administration to a subject. The composition, shape, and type of dosage forms provided herein will typically vary depending on their use.

Generally, the ingredients of compositions are supplied either separately or mixed together in unit dosage form, for example, as a dry lyophilized powder or water free concentrate in a hermetically sealed container such as an ampoule or sachet indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

Typical dosage forms comprise a compound provided herein, or a pharmaceutically acceptable salt or solvate thereof lie within the range of from about 0.01 mg to about 1000 mg per day, given as a single once-a-day dose in the morning or as divided doses throughout the day taken with food. Particular dosage forms can have about 0.01, 0.02, 0.03, 0.04, 0.05, 0.06, 0.07, 0.08, 0.09, 0.1, 0.2, 0.3, 0.4, 0.5, 1.0, 2.0, 2.5, 5.0, 10.0, 15.0, 20.0, 25.0, 50.0, 100, 200, 250, 500 or 1000 mg of the active compound(s).

Methods of Treatment

Provided herein are methods of treating cancer in a subject in need of the treatment, comprising administering an effective amount or a therapeutically effective amount any of the compounds or compositions provided herein to the subject.

The methods provided herein encompass administering pharmaceutical compositions containing at least one compound as described herein, either used alone or in the form of a combination with one or more compatible and pharmaceutically acceptable carriers or excipients, such as diluents or adjuvants.

Provided herein are methods, wherein the subject has been tested or diagnosed for cancer or a risk of cancer, wherein the subject has been treated for cancer, wherein the cancer is breast cancer, wherein the cancer is TNBC, wherein the subject is in need of treatment for cancer, wherein the subject is tested or diagnosed for the presence of cancer following administration of the composition, and/ or any combination or alone of these or any other characteristic disclosed herein.

Provided herein is a method of treating cancer in a subject in need the treatment, the method comprising administering an effective amount or a therapeutically effective amount of any of the compounds provided herein, to the subject.

Provided herein is a method of treating cancer in a subject in need the treatment, the method comprising administering an effective amount or a therapeutically effective amount of any of the compositions or pharmaceutical compositions provided herein, to the subject.

In some embodiments of the methods, the cancer is breast cancer. In some embodiments of the methods, the cancer is TNBC.

Effective amounts, dosages, and schedules for administering the compounds or compositions may be determined empirically, and making such determinations is within the skill in the art. The dosage ranges for the administration of the compositions are those large enough to produce the desired effect in which the symptoms disorder is affected. The dosage should not be so large as to cause adverse side effects, such as unwanted cross-reactions, anaphylactic reactions, and the like. Generally, the dosage will vary with the age, condition, sex and extent of the disease in the patient, route of administration, or whether other drugs are included in the regimen, and can be determined by one of skill in the art. The dosage can be adjusted by the individual physician in the event of any counter indications. Dosage can vary, and can be administered in one or more dose administrations daily, for one or several days. Guidance can be found in the literature for appropriate dosages for given classes of pharmaceutical products. For example, guidance in selecting appropriate doses for antibodies can be found in the literature on therapeutic uses of antibodies, e.g., Handbook of Monoclonal Antibodies, Ferrone et al., eds., Noges Publications, Park Ridge, N.J., (1985) ch. 22 and pp. 303-357; Smith et al., Antibodies in Human Diagnosis and Therapy, Haber et al., eds., Raven Press, New York (1977) pp. 365-359. A typical daily dosage of the antibody used alone might range from about 1 ng/kg to up to 100 mg/kg of body weight or more per day, depending on the factors mentioned above.

The term "effective amount" of a compound or composition as provided herein means a sufficient amount of the compound or composition to provide the desired result. As will be described herein, the exact amount required will vary from subject to subject, depending on the species, age, and general condition of the subject, the severity of the disease that is being treated, the particular compound used, its mode of administration, and the like. Thus, it is not possible to specify an exact "effective amount." However, an appropriate effective amount can be determined by one of ordinary skill in the art using only routine experimentation.

The disclosed compounds and compositions can be administered in any manner or route suitable to the compound or composition and the formulation of the compound or composition. Such techniques are well-known and can be applied to the methods and compositions disclosed herein.

The compounds, compositions, and pharmaceutical compositions described herein can be administered to the subject in a number of ways depending on whether local or systemic treatment is desired, and on the area to be treated. Generally, oral administration is preferred and is generally available for the compounds and compositions disclosed herein. However, a compound or pharmaceutical composition can also be administered to a subject vaginally, rectally, intranasally, by inhalation, or parenterally, for example, by intradermal, subcutaneous, intramuscular, intraperitoneal, intrarectal, intraarterial, intralymphatic, intravenous, intrathecal and intratracheal routes. Parenteral administration, if used, is generally characterized by injection. Injectables can be prepared in conventional forms, either as liquid solutions or suspensions, solid forms suitable for solution or suspension in liquid prior to injection, or as emulsions. Parenteral administration can use a slow release or sustained release system such that a constant dosage is maintained.

Prior to treatment, subjects to be treated can be identified by determining characteristics that indicate the suitability of the treatment for that subject.

The present inventors sought to explore novel chalcone derivatives as leads for potential targeted therapies for TNBCs. In certain aspects, as examples, a library of 14 novel chalcone derivatives were designed and synthesized, the chalcone derivatives comprise alicyclic amines (such as pyrrolidine, morpholine and piperidine) or nitrogen mustard (Bis-(2-chloroethyl)amine) substituents at position 4 of benzene ring B using the Claisen-Schmidt condensation reaction. These new compounds were then purified and their structures were confirmed through various characterization studies (MS, FT-IR, 1D NMR, 2D NMR, elemental analysis and melting point measurements). These new compounds were then evaluated for their pharmacological anticancer activities to investigate their efficacy and safety in vitro and in vivo. In vitro studies were conducted against a panel of five breast cancer cell lines: invasive triple negative breast cancers (MDA-MB-231 and MDA-MB-468), estrogen positive (MCF-7 and BT-474) and HER2 positive (SK-BR-3), and one immortalized normal mammary epithelial cell line (HNME-E6/E7) to determine their activities on cell proliferation, colony formation, apoptosis, cell cycle, invasion, metastasis and EMT, which is an important event in cancer progression and metastasis. Moreover, in vivo experiments were conducted on two animal models, the CAM of the chicken embryos and nude mice, to determine the effects on angiogenesis and tumor growth.

In certain aspects, the pharmacological and biological studies identified compound 13 and 14 as promising hits on TNBC cells. In certain aspects, compound 14 was subsequently identified as the candidate for further development due to its anticancer activities against recognizable TNBC molecular processes with acceptable safety and selectivity. Compound 14 had dramatically inhibited cancer invasion, potently inhibited triple negative breast cancer migration and metastasis and induced apoptosis. Additionally, in vivo testing revealed statistically significant inhibition of blood vessels development in CAM model and inhibition of tumor growth in nude mice. Comparison of compound 14 with conventional anticancer drugs (using cell migration, cell cycle progression and soft agar assays), colchicine and paclitaxel, indicated that it is more effective than these commercial options in terms of inhibiting colony formation (soft agar assay) and inhibiting cell migration/invasion (migration assay/wound healing assay). Regarding cell cycle, the effect was comparable to these medications. Taken together, compound 14 can be considered as a favorable lead compound for targeted treatment of TNBC patients.

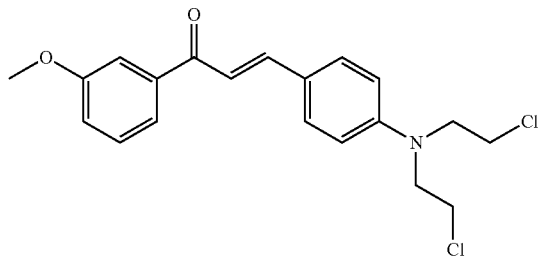 [SMILES: COc1cccc(C(=O)/C=C/c2ccc(N(CCCl)CCCl)cc2)c1]

(E)-3-(4-(bis(2-chloroethyl)amino)phenyl)-1-(3-methoxyphenyl)prop-2-en-1-one

The new compounds are useful for treating TNBC patients that so far have no effective drug or targeted therapy. The new compounds have high specificity for TNBC. The present inventors have tested the new compounds in vitro and in vivo, using cell-lines and animal models, the CAM of the chicken embryo for angiogenesis and nude mice for tumor formation, respectively. Some or all of the new compounds showed superior efficiency than commercially available drugs against TNBC cells with no evident toxicity in vivo.

Examples

1. Summary

A library of 14 novel chalcone derivatives comprising alicyclic amines (pyrrolidine, morpholine and piperidine) or nitrogen mustard (Bis-(2-chloroethyl) amine) substituents were synthesized using the Claisen-Schmidt condensation reaction. They were then purified followed by extensive chemical elucidation studies. Subsequently, pharmacological anticancer activities of the compounds were investigated in vitro, in vivo and in silico.

Compound 14 was identified as the most effective cytotoxic compound with anti-proliferative $IC_{50}$ values ranging between 3.94 and 9.22 µM in TNBC (MDA-MB-231 and MDA-MB-231) and estrogen positive (MCF-7 and BT-474) cell lines. Colony formation of MDA-MB-468, MDA-MB-231 and MCF-7 cells was completely inhibited at 5 and 10 µM concentrations of the compound. Furthermore, it had potently and effectively inhibited tumor invasion and migration in TNBC (MDA-MB-231), estrogen positive (MCF-7) and HER2 positive (SK-BR-3) cell lines with anti-migratory $IC_{50}$ values of 2.86±0.20, 2.44±0.39 and 2.79±0.45 µM, respectively. These actions were noticed to be superior to two conventional anticancer medications, colchicine and paclitaxel. Tubulin polymerization was also inhibited with an effect comparable to colchicine which was also confirmed with molecular docking studies. Additionally, the compound had significantly promoted apoptosis through upregulation of BAX and downregulation of bcl-2 proteins in MDA-MB-231 and MCF-7 cell lines. Concerning cell cycle, it had significantly arrested MDA-MB-231 and MDA-MB-468 TNBC cells at the G2/M phase (47.27±7.869% and 66.45±4.25%, respectively). Compound 14 had as well induced a reversal of EMT by upregulating the epithelial markers E-cadherin and Pan-cadherin. Furthermore, it had dramatically diminished blood vessels formation in a CAM model by 60.20±8.47% and inhibited tumor growth in nude mice xenografted with MAD-MB-231 cells by 46.41±0.71% as compared to the control. Overall, compound 14 was found to be an active and potentially safe lead compound for targeting TNBC and other breast cancers.

2. Materials and Methods 2.1. Chemistry
2.1.1. Materials

All solvents and chemicals were purchased from Sigma-Aldrich (USA). Table 2.1 lists the names of the major chemicals and solvents used in this study. Pre-coated silica gel aluminum plates from Merck (USA) were used for the Thin layer chromatography (TLC).

TABLE 2.1

| Solvents and chemicals used | |
|---|---|
| Chemicals/Solvents | |
| Acetophenones | 3-chloroqcetophenone (MW 154.59, d: 1.191 g) |
| | 4-(methylsulfonyl) Acetophenone (MW 198.24) |
| | 4-(methylthio) Acetophenone (MW 166.24) |
| | 3-methoxy Acetophenone (MW 150.18, d: 1.094 g/ml) |
| | 3',4'-(methylenedioxy) Acetophenone (MW 164.16) |
| | 4'-Piperazinoacetophenone (MW 204.27) |
| | 2-methoxy Acetophenone (MW 150.18, d = 1.094 g/ml) |
| Benzaldehydes | 4-(1-pyrrolidino) benzaldehyde (MW 175.23) |
| | 4-(4-Morpholinyl) benzaldehyde (MW 191.23) |

TABLE 2.1-continued

| Solvents and chemicals used | |
|---|---|
| Chemicals/Solvents | |
| | 4-(1-piperidinyl) benzaldehyde (MW 189.25) |
| | 4-[Bis-(2-chloroethyl) amino] benzaldehyde (MW 246.13) |
| Other chemicals Solvents | Sodium hydroxide (NaOH) |
| | Methanol |
| | Chloroform-d |
| | Dichloromethane |
| | Ethanol |
| | Ethyl acetate |
| | N-hexane |

2.1.2. Experimental
2.1.2.1. Design of Chalcone Derivatives

A literature search was performed at the start to look for functional groups with potential promising anticancer activities. A group of chalcone derivatives was then designed and their novelty was checked using SciFinder database. Only new derivatives were selected for this study.

2.1.2.2. Synthesis of Chalcone Derivatives

Figure 2:
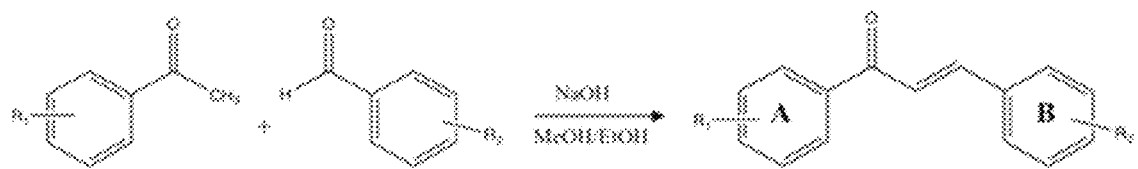
FIG. 2 illustrates a synthetic route for the synthesis of chalcone derivatives.

Chalcone derivatives were synthesized by Claisen-Schmidt condensation reaction using appropriate equimolar amounts of substituted acetophenones and benzaldehydes in MeOH/EtOH. NaOH was dissolved in the least amount of water and added dropwise (3 mmol). FIG. 2.1 illustrates the synthetic route for the synthesis of chalcone derivatives.

Reactions were stirred overnight. All reactions were monitored by TLC using appropriate solvent or mixture of solvents. When the reaction complete, the obtained precipitate was filtered, washed with cold methanol and dried under vacuum. The crude products were crystallized from different solvent systems based on their solubility or purified by column chromatography to give pure crystalline compounds. The yield for every compound was calculated using the following formula:

$$\% \text{ Yield} = \frac{\text{Actual Yield}}{\text{Theoretical Yield}} \times 100$$

2.1.2.3. Chemical Characterization and Elucidation
2.1.2.3.1. Fourier Transform-Infrared Analysis Fourier Transform-Infrared analysis was carried out using Perkin Elmer Spotlight 400 Fourier transform infrared (FTIR) Spectrophotometer to confirm the presence of the main functional groups present in each of the synthesized chalcone derivatives. The spectra were collected over a 4000-400 $cm^{-1}$ wavelength and were analyzed at room temperature using universal attenuated total reflectance (UATR) detector.

2.1.2.3.2. Melting Points

Melting points were measured using Stuart SMP40 automatic melting point apparatus (Bibby Scientific Ltd, UK).

2.1.2.3.3. Mass Spectroscopy

Mass Spectrometry analysis was carried on Agilent 6460 Triple Quadrupole Liquid chromatography-mass spectrometry (LC/MS system) using electrospray ionization (ESI) for confirming the molecular weights of the synthesized chalcone compounds expressed in $[M+1]^+$. Compounds 8, 10, 13 and 14 Mass Spectrometric analysis was carried using High-resolution JEOL JMST100 LP AccuTOF LC-Plus equipped with an ESI source (JEOL, Japan).

2.1.2.3.4. Nuclear Magnetic Resonance (NMR)

NMR spectroscopic analysis was conducted using JNM-ECZR (600 MHz and 150 MHz) FT Spectrometer (JEOL, USA) for the analysis of 1D ($^1$H and $^{13}$C) and 2D (COSY, HMBC and HMQC) NMR of the different compounds to confirm the chemical structure of the compounds. Chloroform-d was used as the reference solvent. Data processing was conducted using Delta NMR Software, Version 5.1.3. (JEOL, USA). Chemical shifts were recorded as parts per million (ppm) relative to the solvent peak. The coupling constant (J) was recorded in Hertz (Hz).

2.1.2.3.5. Elemental Analysis

The percentage of carbon, hydrogen and nitrogen content in every compound was calculated to confirm the molecular structures of the compounds and their purity using Thermo Scientific FLASH 2000 CHNS/O analyzer.

2.2. Pharmacological Screening 2.2.1. Cell Culture

Breast cancer cell lines including MDA-MB-231, MDA-MB-468, MCF-7, BT-474 and SK-BR-3 were obtained from the American Type Tissue Culture (ATCC) and maintained in complete cell culture media Gibco® RPMI 1640 (Thermo Fisher Scientific, USA) supplemented with 10% fetal bovine serum (PAN-Biotech, Aidenbach, Bavaria, Germany) and 1% penicillin/streptomycin (1×) antibiotics (Thermo Fisher Scientific, USA). Human normal mammary epithelial cells immortalized by E6/E7 of HPV type 16 (HNME-E6/E7) were used to predict potential safety of the compounds (125, 126). They were maintained in Gibco® Keratinocyte-SFM (1×) media. All cells were incubated in 5% CO2 at 37 C° incubator. Cells were maintained by routine sub-culturing in T-75 and T25 filtered tissue culture flasks.

2.2.2. Stock Solutions

The fourteen compounds were dissolved in Dimethyl Sulfoxide (DMSO) and stock solutions were prepared at a concentration of 5 or 25 mM. These stock solutions were used to prepare different serial dilutions required for the different experiments. MTT (3-(4,5-Dimethylthiazol-2-yl)-2,5-diphenyltetrazolium bromide) stock solution was prepared at a concertation of 5 mg/ml using Gibco™ PBS 1× buffer (Thermo Fisher Scientific, USA) as a solvent. The solution was used to assess the viability of the cells. Formaldehyde (Riedel-deHaen, Germany) fixator was prepared at a concentration of 3.70% and was used in the invasion assay. A 2% Agar solution was prepared for the soft agar assay by dissolving agar (Sigma-Aldrich, USA) in PBS through heating.

2.2.3. Cell Viability

MDA-MB-231, MDA-MB-468, MCF-7, BT-474 and HNME-E6/E7 cells were seeded overnight in 96-well plates at a concentration of 8000-10,000/well depending on their pre-calculated cell density and were incubated overnight. At 24 hours, media was replaced with fresh one. The treatment wells included 6-8 different concentrations of the compounds ranging between 0.25 μM-160 μM. At 48 hours post treatment, 10 μL MTT solution was added to each well followed by 4 hours of incubation. Afterwards, media with MTT was removed from all wells and 50 μl DMSO was added to each well to dissolve the crystals. This was followed by 5 minutes incubation. Absorbance was recorded at a wavelength of 562 nm after 3 minutes of shaking using Infinite 200 PRO Microplate Reader (Tecan, Switzerland). Percentage of viable cells was calculated using the following formula:

$$\% \text{ Viability} = \frac{\text{Absorbance of treated}}{\text{Absorbance of untreated}} \times 100$$

2.2.4. Morphological Examination

MCF-7, MDA-MB-231, MDA-MB-468 and HNME-E6/E7 cells were seeded in a 6-well plates at a concentration of 200,000-300,000 cells/well and were incubated overnight. After incubation, cells were treated with different compounds. Cell morphology was observed with DMi8 inverted microscope (Leica, Germany).

2.2.5. Annexin V Apoptosis Assay

PE Annexin V apoptosis Detection Kit (BD Pharmingen, USA) was used to quantify cell apoptosis in treated versus untreated MDA-MB-468 cells at 24 and 48 hours post treatment. Briefly, cells were seeded at a density of 300,000 cells/well in 6-well plates. Second day, media was replaced with fresh media and treatment was added. Cells were harvested following treatment and each group of cells was stained with PE Annexin V and 7-AAD Annexin V as per the protocol specified on the kit. Samples were then analyzed by Accuri C6 flow cytometer (BD Biosciences, USA). The percentages of cells (viable cells, apoptotic cells, necrotic cells and dead cells) were quantified in each of the four quadrants. Data and figures were processed using the FlowJo V10 software.

2.2.6. Cell Cycle Analysis

The MDA-MB-231, MDA-MB-468 and MCF-7 cell lines were seeded on 6-well plates at a concentration of 200,000 cells per well and were maintained in culture supplemented with 10% fetal bovine serum for 8-10 hours. The same day, media was removed and cells were incubated overnight with serum free media. Second day, cells were treated with the compounds. Adherent and floating cell populations were harvested at 48 hours after treatment with different concentrations of the compounds and counted.

Afterward, cells were washed with cold PBS once, centrifuged at 4° C. and fixed with 1.5 ml cold 70% ethanol added drop wise while slowly vortexing. Samples were then stored at 20° C. Following fixation, cells were pelleted and washed with ice-cold PBS. Equal aliquots were collected and resuspended in 300 μl of Tali® Cell Cycle Kit and incubated at 37 C with slow shaking speed for 30 minutes in the dark. Accuri C6 flow cytometer (BD Biosciences, USA) was used to analyze the cells. The FlowJo V10 software was used to process and evaluate the results.

2.2.7. Invasion Assay

Matrigel-coated invasion chamber plates (CORNING, USA) were used to study the invasive property of MDA-MB-231, MDA-MB-468 and MCF-7 cancer cells. Cells were seeded at a concentration of 5×10$^4$ cells/0.5 ml in each upper chamber well and maintained in RPMI serum free medium. Complete RPMI medium with 10% FBS was added to each base well at 600 μl/well to act as an attractant to the cells in the upper chamber. After 24 hours, cells were fixed using a 3.70% formaldehyde as a fixator for 5 minutes. This was followed by several rounds of washing of the top part of each well with PBS to remove cells that did not invade. Thereafter, cells were stained using 5% crystal violet dissolved in ethanol and were incubated for 5 minutes followed by several rounds of washing with PBS. Cells were then visualized under the microscope and 4 pictures/well were taken from different zones. ImageJ software was used to quantify the number of invaded cells in each well.

2.2.8. Soft Agar Growth Assay

The soft agar assay was used to assess the ability of the cells to form colonies in vitro. A 0.4% agar solution was prepared by mixing with complete RPMI culture media supplemented with fetal bovine serum. A 1 ml solid layer was then created in each well of the 6-wells plates. After drying, a 0.2% agar solution containing 20,000 cells/well was prepared and added on top of the solid 0.4% agar layers. After 24 hours, the required quantity from each compound was mixed with RPMI media. Colonies were monitored for 2-3 weeks and microscopic pictures were taken from different zones. Colonies from each well were counted under the microscope.

2.2.9. Migration Assay

MDA-MB-231 cells were seeded in 12-wells plates at a concentration of 500,000 cells/well and were incubated in complete RPMI culture medium until covering the well and reaching around 90-100% confluency. Following, cells were serum starved for 4 hours and a 200 µl pipette tip was used to create the scratch followed by cell washing with PBS twice. Different compounds were then added at a concentration of 5 µM in RPMI media with 0.5% serum. Microscopic pictures were then taken, and cell migration was quantified based on the wound diameter at 24 hours minus the initial diameter at time zero, as represented by the following equation:

% Migration=(Initial width−width at 24 hrs)×100

For MCF-7 and SK-BR-3 cell lines, migration testing was performed using the Radius™ Cell Migration Assay Kit (Cell Biolabs, Inc., USA) and migration was quantified based on the change in wound area.

2.2.10. Western Blot Analyses

Proteins were quantified with the Pierce BCA Protein Assay Kit (Thermo Scientific, USA) following cell lysis. SDS-PAGE was prepared at a concentration of 10% for all studied proteins. All samples were loaded at 40 µg per 1.5 mm 15 wells comb. Running of stained samples was performed using two steps gel electrophoresis (60 Volts for 20 minutes followed by 120 Volts for 1 hour). Afterwards, gels were transferred into PVDF membrane at 100 Voltage for 1.5-2.0 hours using wet transfer. Following transfer, PVDF membranes were blocked with 5% skimmed milk and washed three times. Primary antibodies (Table 2. 2) were prepared, then PVDF membrane were incubated with them overnight with gentle shaking at 4° C. Afterwards, membranes were washed three times and incubated with their respective secondary antibodies for 1-2 hours with gentle shaking at room temperature. Pierce™ ECL Western Blotting Substrate was used to detect proteins by chemiluminescence. Blots were imaged using the ibrightCL1000 imaging system.

2.2. List of Used Primary and Secondary Antibodies

| Antibody | Type | Source | MW of target protein | Manufacturers |
|---|---|---|---|---|
| Anti-Mouse | polyclonal and monoclonal | Mouse | NA | Cell Signaling Technology, Inc., USA |
| Anti-Rabbit | polyclonal and monoclonal | rabbit | NA | Cell Signaling Technology, Inc., USA |
| β-actin | monoclonal | Mouse | 42 kDa | NeoBioLab, USA |
| β-Catenin | polyclonal | Rabbit | 92 kDa | Cell Signaling Technology, Inc., USA |
| Phospho-β-Catenin | polyclonal | Rabbit | 92 kDa | Cell Signaling Technology, Inc., USA |
| E-cadherin | monoclonal | mouse | 135 kDa | Cell Signaling Technology, Inc., USA |
| Pan-cadherin | polyclonal | Rabbit | 135 kDa | Cell Signaling Technology, Inc., USA |
| BAX | monoclonal | Mouse | 23 kDa | Invitrogen, USA |
| Bcl-2 | monoclonal | Rabbit | 26 kDa | Abcam, USA |
| FAK | polyclonal | Rabbit | 125 kDa | Cell Signaling Technology, Inc., USA |

NA: Not Applicable

2.2.11. Molecular Docking

Computer aided-molecular docking studies were conducted using Schrödinger molecular modeling software installed on an iMac 27-inch Z0 PG workstation (Apple, Cupertino, Calif.). Compound 14 structure was docked into the colchicine binding site of the β-tubulin to determine its binding mode and affinity. Tubulin protein crystal structure was downloaded from the protein databank (PDB code: 5LYJ).

2.2.12. Tubulin Polymerization Assay

The effect of compound 14 on tubulin polymerization dynamics was assessed using the cell free Cytoskeleton tubulin polymerization assay kit, Version 8.3 (Cytoskeleton, Inc., USA). The experiment was conducted based on the manufacturer's recommendations. colchicine was used as a depolymerizing control while paclitaxel was used as a polymerizing control. Briefly, stock solutions of 10 µM of the compounds and controls were prepared in general tubulin buffer. Then, 10 µl of each solution was added in duplicates in half area 96-well plate prewarmed at 37° C. It was subsequently incubated at 37° C. for 2 minutes. Tubulin solution was prepared and 100 µl of it was added to each of the prewarmed wells of the compounds. The plate was immediately placed at a plate reader set up at kinetic modes and 37° C. temperature. Recording was conducted every minute for 60 minutes at 340 nm Absorbance.

2.2.13. Chorioallantoic Membrane (CAM) Angiogenesis Assay

Fertilized white Leghorn chicken embryos (Arab Qatari for Poultry Production, Qatar) were purchased and incubated at 60% humidity at 37° C. in MultiQuip incubator. Ethics approval was obtained from Qatar University-Institutional Bio-safety committee. The embryos were treated in ovo at embryonic day 4 with three of the synthesized chalcones (5, 13 and 14) compared to DMSO treated controls. Briefly, a small cut was made at the top of the shells of the eggs and each treatment was added under a round coverslip at 2 µl of 5 mM stock solutions. Microscopic pictures were taken at embryonic day 8. Embryos treated with compounds 13 and 14 were sacrificed at embryonic day 9 for clinical observations. Quantification of blood vessels was performed manually and the different treatment groups were compared.

2.2.14. In Vivo Tumor Growth

2.2.14.1. Animals

Female nude mice (Envigo, Indianapolis, Ind.) were maintained under clean room conditions inside University of Louisiana at Monroe animal housing facility. The mice were handled strictly in accordance with national institutes of health (NIH) guideline. They were acclimated in sterile filter top cages and Alpha-Dri bedding. They were housed at 12 h light/dark cycle, 25° C.; on high efficiency particulate air-filtered ventilated racks and relative humidity of 55-65%. The mice had free access to pelleted rodent chow (Harlan/Teklad, Madison, Wis.) and drinking water. Ethical approval was obtained from the Institutional Animal Care and Use Committee (IACUC) at the University of Louisiana at Monroe.

2.2.14.2. Xenograft Model

MDA-MB-231, TNBC, cells were harvested, centrifuged at 850×g for 5 min, and the pellet was re-suspended in sterile serum-free RPMI medium (30 µL) and Matrigel Matrix (Discovery Labware, Inc., Bedford, Mass.). Tumor cell suspension (1×10$^6$ cells/50 µL) was inoculated into the second mammary gland fat pad subcutaneously beneath the nipple of each ketamine-anesthetized animal to form orthotropic breast tumors. Compound 14 was dissolved in PBS and few drops of tween 80 (<0.1%). Treatment with compound 14 (10 mg/kg, 5 times per week) started 15 days before-inoculation with intraperitoneal (i.p) injections to predict safety and tolerability of the dose. Following 2 days post-inoculation, mice were divided randomly into two sets: placebo (n=5) or compound 14 (n=5). Mice were then treated with compound 14 (10 mg/kg, 3 times per week) or equivalent volume of placebo (100 µl of PBS and <0.1% tween 80). They were then monitored 3 times per week by measuring body weight, tumor volume (Length/2×Width$^2$) and other clinical observations.

2.2.15. Statistical Analysis

The data were expressed as an average of mean±SEM (standard error of the mean) of triplicates from three independent experiments, unless otherwise indicated. Statistical analysis of the data was conducted using GraphPad Prism version 7. Differences between compounds 1-14 and controls were determined based on One-way analysis of variance (ANOVA) followed by Tukey's post-hoc test. For the tumor growth in vivo experiment, differences between placebo and compound 14 were determent based on student's t-test. Results were considered statistically significant when P-values were <0.05. Kaplan-Meier survival analysis was performed to demonstrate the effect on survival of compound 14 and placebo treated mice. IC$_{50}$ and LD$_{50}$ values were computed using nonlinear regression test.

3. Results 3.1. Chemical Synthesis and Structural Elucidation 3.1.1. Synthesis

Novel chalcone derivatives were synthesized through the Claisen-Schmidt condensation reaction by reacting equimolar quantities of substituted acetophenones and appropriate benzaldehydes in methanol in presence of 3 equivalents NaOH at room temperature. The products were collected and purified by crystallization or column chromatography. Fourteen compounds (1-14) containing chloro, methylsulfonyl, methylthio, methoxy, methylenedioxy, piperazine, pyrrolidine, morpholine, piperidine and nitrogen mustard chemical moieties were successfully synthesized (FIG. 3.1).

3.1.2. Structural Elucidation

The structures of the synthesized analogs were confirmed using pertinent spectroscopic techniques. Liquid chromatography-mass spectrometry (LC/MS), melting points measurement, elemental analysis, Fourier-transform infrared (FT-IR) spectroscopy and nuclear magnetic resonance (NMR) spectroscopy were used to conduct the different characterization studies on the compounds. Overall, yields of the 14 chalcone analogs ranged between 42-86% with melting points (m.p.) recorded to be above 90° C. FT-IR analysis confirmed the presence of the major functional groups on the different analogs. Notably, carbonyl group appeared at a lower wavelength (1640-1670 cm$^{-1}$) than what is usually observed with ketones (1715 cm$^1$). This confirmed the existence of the carbonyl group conjugated with the double bond in chalcone structure. The calculated molecular weights of the compounds were confirmed by the presence of [M+1]+ molecular ion peaks by LC-MS. This was further confirmed through analyzing elemental C, N and H contents in the products, which were found to be relatively similar to the ones calculated for each molecular formula. 1D NMR ($^1$H-NMR and $^{13}$C-NMR) analysis confirmed the expected chemical shifts of the different H and C present in each compound. Additionally, $^1$H-NMR analysis confirmed the existence of the chalcone products in (E) configuration, which was evident by the presence of a large coupling constant (~16 Hz) of the α and β-olefinic protons. Compounds 13 and 14 structural configurations were further confirmed through 2D NMR (COSY, HMBC and HSQC/HMQC) for full assignments of all protons and carbons. The results of the characterization studies for compounds 1-14 are summarized below. Spectra of Compound 14 are included in FIG. 4.1 to FIG. 4.7.

Compound 1, (E)-1-(3-chlorophenyl)-3-(4-(pyrrolidin-1-yl) phenyl) prop-2-en-1-one

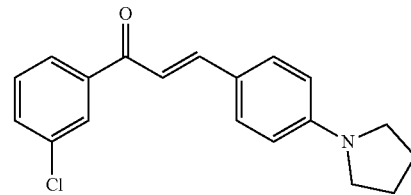

Yellow solid; yield=53.4%; m.p.=100.8-101.8° C.; $^1$H-NMR (600 MHz, CDCl$_3$) δ 7.97 (s, 1H, H-2), 7.88 (d, J=7.2 Hz, 1H, H-4), 7.82 (d, J=15 Hz, 1H, β-olefinic), 7.56 (d, J=8.4, 2H, H-2' and H-6'), 7.52 (d, J=7.8, 1H, H-6), 7.43 (m, J=7.8 Hz, 1H, H-5), 7.26 (d, J=15.6 Hz, 1H, α-olefinic), 6.56 (d, J=7.8 Hz, 2H, H-3' and H-5'), 3.38 (s, 4H, H-2" and H-5"), 2.05 (s, 4H, H-3" and H-4"); $^{13}$C-NMR (150 MHz, CDCl$_3$) δ 189.2, 149.9, 147.1, 141.0, 134.8, 130.9, 129.8, 128.5, 126.4, 122.0, 115.6, 111.9, 47.7, 25.5; FT-IR: 3100 (C=C—H), 2965 (C—C—H), 1643 (C=O), 1613 (C=C), 1574, 1524 (C=C, aryl), 1178 (C—N) cm$^{-1}$; Anal. calcd. for C$_{19}$H$_{18}$ClNO: C, 73.19; H, 5.82; N, 4.49; Found: C, 71.46; H, 5.27; N, 4.45. LC-MS (+)-ESI (m/z): calculated 311.11, observed 312.1 [M+1]$^+$.

Compound 2, (E)-1-(4-(methylsulfonyl) phenyl)-3-(4-(pyrrolidin-1-yl) phenyl) prop-2-en-1-one

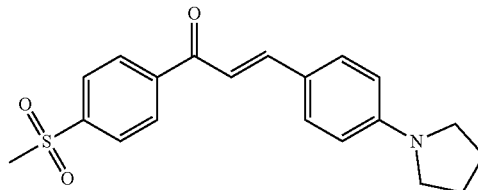

Orange-red solid; yield=45%; m.p.=89.7-90.7° C.; $^1$H-NMR (600 MHz, CDCl$_3$) δ 8.10 (d, J=8.4 Hz, 2H, H-2 and H-6), 8.02 (d, J=8.4 Hz, 2H, H-3 and H-5), 7.78 (d, J=15.6 Hz, 1H, β-olefinic), 7.52 (d, J=9, 2H, H-2' and H-6'), 7.20 (d, J=15.6 Hz, 1H, α-olefinic), 6.53 (d, J=9 Hz, 2H, H-3', H-5'), 3.34 (s, 3H, SO$_2$CH$_3$), 3.07 (m, J=5.4 Hz, 4H, H-2" and H-5"), 2.23 (m, J=5.4 Hz, 4H, H-3" and H-4"); $^{13}$C-NMR (150 MHz, CDCl$_3$) δ 189.4, 150.2, 148.2, 143.9, 143.0, 131.2, 129.1, 127.7, 121.6, 115.4, 47.7, 44.5, 25.5; FT-IR: 3100 (C=C—H), 2967 (C—C—H), 1670 (C=C), 1650 (C=O), 1613, 1519 (C=C, aryl), 1149 (C—N) cm$^{-1}$; Anal. calcd. for C$_{20}$H$_{21}$NO$_3$S: C, 67.58; H, 5.96; N, 3.94; Found: C, 67.20; H, 5.87; N, 4.08. LC-MS (+)-ESI (m/z): calculated 355.12, observed 356.1 [M+1]$^+$.

Compound 3, (E)-1-(4-(methylsulfonyl) phenyl)-3-(4-morpholinophenyl) prop-2-en-1-one

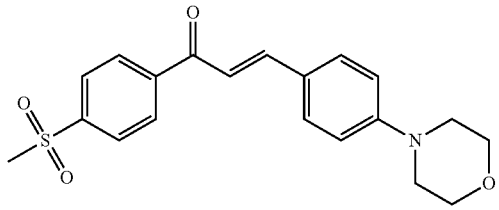 [SMILES: CS(=O)(=O)c1ccc(C(=O)/C=C/c2ccc(N3CCOCC3)cc2)cc1]

Pale orange solid; yield=84.5%; m.p.=115.5-116.5° C.; $^1$H-NMR (600 MHz, CDCl$_3$) δ 8.13 (d, J=8.4 Hz, 2H, H-2 and H-6), 8.06 (d, J=8.4 Hz, 2H, H-3 and H-5), 7.78 (d, J=15.6 Hz, 1H, β-olefinic), 7.57 (d, J=9, 2H, H-2' and H-6'), 7.20 (d, J=15.6 Hz, 1H, α-olefinic), 6.89 (d, J=9 Hz, 2H, H-3' and H-5'), 3.86 (m, J=4.8 Hz, 4H, H-2" and H-6"), 3.29 (m, J=5.4 Hz, 4H, H-3" and H-5"), 3.10 (s, 3H, SO$_2$CH$_3$); $^{13}$C-NMR (150 MHz, CDCl$_3$) δ 189.5, 153.2, 147.0, 143.4, 143.2, 130.6, 129.2, 127.8, 125.2, 118.0, 114.6, 66.7, 47.8, 44.5; FT-IR: 3089 (C=C—H), 2971 (C—C—H), 1654 (C=O), 1567 (C=C), 1594, 1514 (C=C, aryl), 1178 (C—N) cm$^{-1}$; Anal. calcd. for C$_{20}$H$_{21}$NO$_4$S: C, 64.67; H, 5.70; N, 3.77; Found: C, 64.60; H, 5.69; N, 3.91. LC-MS (+)-ESI (m/z): calculated 371.12, observed 372.1 [M+1]$^+$.

Compound 4, (E)-1-(4-(methylsulfonyl) phenyl)-3-(4-(piperidin-1-yl) phenyl) prop-2-en-1-one

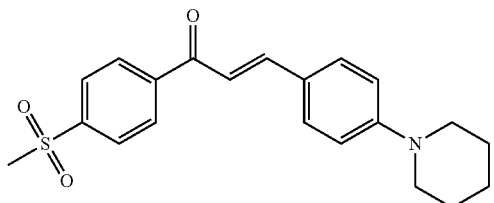

Orange solid; yield=81.2%; m.p. decomposed; $^1$H-NMR (600 MHz, CDCl$_3$) δ 8.12 (d, J=8.4 Hz, 2H, H-2 and H-6), 8.05 (d, J=8.4 Hz, 2H, H-3 and H-5), 7.77 (d, J=15.6 Hz, 1H, β-olefinic), 7.53 (d, J=9, 2H, H-2' and H-6'), 7.26 (d, J=16.2 Hz, 1H, α-olefinic), 6.87 (d, J=9 Hz, 2H, H-3' and H-5'), 3.34 (m, J=4.8, 4H, H-3" and H-5"), 1.67 (m, 4H, H-2" and H-6"), 3.08 (m, 3H, SO$_2$CH$_3$), 1.64 (m, 2H, H-4"); $^{13}$C-NMR (150 MHz, CDCl$_3$) δ 189.5, 153.6, 147.5, 143.6, 143.2, 130.8, 129.2, 127.7, 123.6, 116.9, 114.6, 48.9, 44.5, 25.5, 24.4; FT-IR: 3011 (C=C—H), 2926 (C—C—H), 1670 (C=C), 1653 (C=O), 1579, 1513 (C=C, aryl), 1152 (C—N) cm$^{-1}$; Anal. calcd. for C$_{21}$H$_{23}$NO$_3$S: C, 68.27; H, 6.27; N, 3.79; Found: C, 68.11; H, 6.50; N, 3.85. LC-MS (+)-ESI (m/z): calculated 369.14, observed 370.2 [M+1]$^+$.

Compound 5, (E)-1-(4-(methylthio) phenyl)-3-(4-morpholinophenyl) prop-2-en-1-one

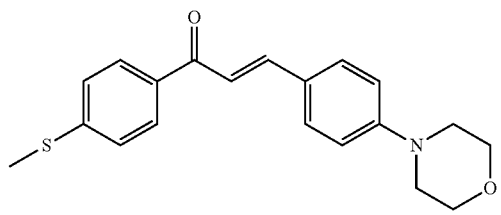 [SMILES: CSc1ccc(C(=O)/C=C/c2ccc(N3CCOCC3)cc2)cc1]

Orange solid; yield=81.2%; m.p.=129.1-130.1° C.; $^1$H-NMR (600 MHz, CDCl$_3$) δ 7.94 (d, J=8.4 Hz, 2H, H-3 and H-5), 7.76 (d, J=15.6 Hz, 1H, β-olefinic), 7.55 (d, J=9, 2H, H-2' and H-6'), 7.36 (d, J=15.0 Hz, 1H, α-olefinic), 7.28 (d, J=8.4 Hz, 2H, H-2 and H-6), 6.87 (d, J=9 Hz, 2H, H-3' and H-5'), 3.84 (m, J=4.8, 4H, H-2" and H-6"), 3.25 (m, J=4.8, 4H, H-3" and H-5"), 2.52 (s, 3H, SCH$_3$); $^{13}$C-NMR (150 MHz, CDCl$_3$) δ 189.3, 152.8, 145.1, 144.7, 135.1, 130.2, 128.9, 126.0, 125.2, 118.4, 114.7, 66.7, 48.1, 15.0; FT-IR: 3100 (C=C—H), 2956 (C—C—H), 1670 (C=C), 1645 (C=O), 1588, 1513 (C=C, aryl), 1175 (C—N) cm$^{-1}$; Anal. calcd. for C$_{20}$H$_{21}$NO$_2$S: C, 70.77; H, 6.24; N, 4.13; Found: C, 69.76; H, 6.36; N, 4.17. LC-MS (+)-ESI (m/z): calculated 339.13, observed 340.60 [M+1]$^+$.

Compound 6, (E)-1-(4-(methylthio) phenyl)-3-(4-(piperidin-1-yl) phenyl) prop-2-en-1-one

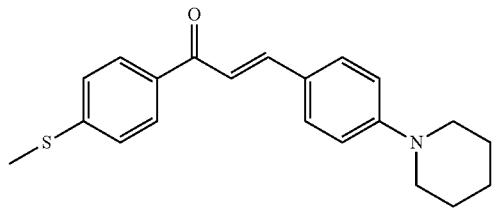 [SMILES: CSc1ccc(C(=O)/C=C/c2ccc(N3CCCCC3)cc2)cc1]

Yellow solid; yield=65.8%; m.p. decomposed; $^1$H-NMR (600 MHz, CDCl$_3$) δ 7.94 (d, J=8.4 Hz, 2H, H-3 and H-5), 7.76 (d, J=15.0 Hz, 1H, β-olefinic), 7.52 (d, J=8.4 Hz, 2H, H-2 and H-6), 7.34 (d, J=16.2 Hz, 1H, α-olefinic), 7.28 (d, J=9, 2H, H-2' and H-6'), 6.87 (d, J=9 Hz, 2H, H-3' and H-5'), 3.29 (m, J=4.8, 4H, H-2" and H-6"), 2.52 (s, 3H, SCH$_3$), 1.66 (m, J=4.2, 4H, H-3" and H-5"), 1.62 (m, 2H, H-4"); $^{13}$C-NMR (150 MHz, CDCl$_3$) δ 189.4, 153.3, 145.0, 144.7, 135.3, 130.3, 128.9, 125.2, 124.5, 117.5, 114.9, 49.1, 25.5, 24.4, 15.0; FT-IR: 3032 (C=C—H), 2929 (C—C—H), 1666 (C=O), 1646 (C=C), 1584, 1514 (C=C, aryl), (C—N) cm$^{-1}$; Anal. calcd. for C$_{21}$H$_{23}$NOS: C, 74.74; H, 6.87; N, 4.15; Found: C, 70.98; H, 6.99; N, 4.86. LC-MS (+)-ESI (m/z): calculated 337.15, observed 338.7 [M+1]$^+$.

Compound 7, (E)-1-(4-(methylthio) phenyl)-3-(4-(pyrrolidin-1-yl) phenyl) prop-2-en-1-one

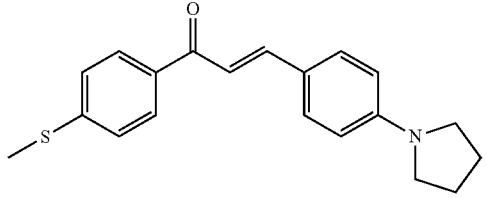 [SMILES: CSc1ccc(C(=O)/C=C/c2ccc(N3CCCC3)cc2)cc1]

Yellow solid; yield=86.6%; m.p. decomposed; ¹H-NMR (600 MHz, CDCl₃) δ 7.93 (d, J=7.8 Hz, 2H, H-2 and H-6), 7.85 (d, J=8.4 Hz, 2H, H-3 and H-5), 7.79 (d, J=16.2 Hz, 1H, β-olefinic), 7.52 (d, J=8.4, 2H, H-2' and H-6'), 7.29 (d, J=15 Hz, 1H, α-olefinic), 6.54 (d, J=8.4 Hz, 2H, H-3' and H-5'), 3.35 (m, J=6.6, 4H, H-2" and H-5"), 2.55 (s, 3H, SO₂CH₃), 2.03 (m, J=1, 4H, H-3" and H-4"); ¹³C-NMR (150 MHz, CDCl₃) δ 189.4, 152.0, 146.0, 144.6, 135.4, 130.7, 128.8, 125.1, 124.9, 116.0, 111.9, 47.7, 25.5, 15.0; FT-IR: 3000 (C=C—H), 2967 (C—C—H), 1667 (C=O), 1638 (C=C), 1584, 1525 (C=C, aryl), 1158 (C—N) cm¹; Anal. calcd. for C₂₀H₂₁NOS: C, 74.27; H, 6.54; N, 4.33; Found: C, 70.91; H, 5.11; N, 5.70. LC-MS (+)-ESI (m/z): calculated 323.13, observed 324.7 [M+1]⁺.

Compound 8, (E)-1-(3-methoxyphenyl)-3-(4-(pyrrolidin-1-yl) phenyl) prop-2-en-1-one

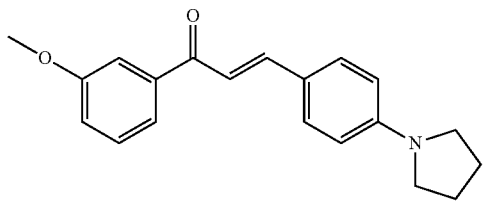 [SMILES: COc1cccc(C(=O)/C=C/c2ccc(N3CCCC3)cc2)c1]

Orange-yellow solid; yield=86.6%; m.p.=165.4-166.3° C.; ¹H-NMR (600 MHz, CDCl₃) δ 7.79 (d, J=15.6 Hz, 1H, β-olefinic), 7.57 (d, J=7.8 Hz, 1H, H-6), 7.53 (d, J=9, 2H, H-2' and H-6'), 7.38 (m, J=4.0, 1H, H-5), 7.28 (d, J=14.4 Hz, 1H, α-olefinic), 7.25 (s, 1H, H-2), 7.08 (dd, J=9, 3 Hz, 1H, H-4), 6.55 (d, J=8.4 Hz, 2H, H-3' and H-5'), 3.87 (s, 3H, OCH₃), 3.35 (m, J=6.6, 4H, H-2" and H-5"), 2.03 (m, 4H, H-3" and H-4"); ¹³C-NMR (150 MHz, CDCl₃) δ 190.4, 159.9, 152.0, 146.3, 140.7, 130.7, 129.5, 124.9, 120.9, 118.7, 116.5, 112.8, 55.6, 47.8, 25.5; FT-IR: 3100 (C=C—H), 2861 (C—C—H), 1660 (C=O), 1641 (C=C), 1597, 1525 (C=C, aryl), 1157 (C—N) cm⁻¹; Anal. calcd. for C₂₀H₂₁NO₂: C, 78.15; H, 6.89; N, 4.56; Found: C, 76.255; H, 6.082; N, 4.283. LC-MS (+)-ESI (m/z): calculated 307.16, observed 308.3 [M+1]⁺.

Compound 9, (E)-1-(3-methoxyphenyl)-3-(4-(piperidin-1-yl)phenyl)prop-2-en-1-one

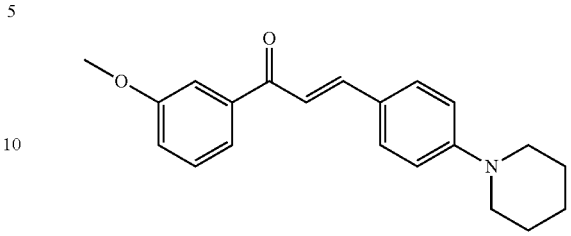

Yellow solid; yield=58.25%; m.p.=150.4-151.4° C.; ¹H-NMR (600 MHz, CDCl₃) δ 7.77 (d, J=15.0 Hz, 1H, β-olefinic), 7.58 (d, J=7.2 Hz, 1H, H-6), 7.52 (d, J=8.4, 2H, H-2' and H-6'), 7.38 (m, J=7.8 Hz, 1H, H-5), 7.32 (d, J=15.0 Hz, 1H, α-olefinic), 7.25 (s, 1H, H-2), 7.09 (dd, J=7.8, 2.4 Hz, 1H, H-4), 6.87 (d, J=9 Hz, 2H, H-3' and H-5'), 3.86 (s, 3H, OCH₃), 3.30 (m, J=4.8 Hz, 4H, H-2" and H-6"), 1.67 (m, 4H, H-3" and H-5"), 1.62 (m, 2H, H-3"); ¹³C-NMR (150 MHz, CDCl₃) δ 190.5, 159.9, 153.3, 145.6, 140.5, 130.2, 129.5, 124.4, 121.0, 118.8, 117.9, 114.7, 112.9, 55.5, 49.2, 25.5, 24.4; FT-IR: 3084 (C=C—H), 2921 (C—C—H), 1651 (C=O), 1609 (C=C), 1568, 1518 (C=C, aryl), 1166 (C—N) cm⁻¹; Anal. calcd. for C₂₁H₂₃NO₂: C, 78.47; H, 7.21; N, 4.36; Found: C, 78.44; H, 7.39; N, 4.47. LC-MS (+)-ESI (m/z): calculated 321.17, observed 322.7 [M+1]⁺.

Compound 10, (E)-1-(benzo[d][1,3] dioxol-5-yl)-3-(4-(pyrrolidin-1-yl) phenyl) prop-2-en-1-one

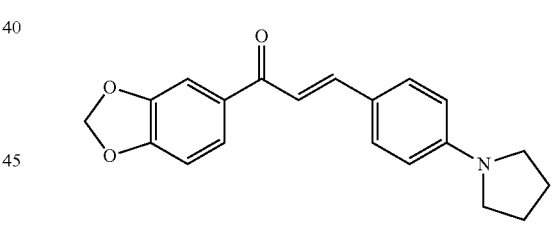

Orange solid; yield=46.9%; m.p.=135.3-136.3° C.; ¹H-NMR (600 MHz, CDCl₃) δ 7.77 (d, J=15.0 Hz, 1H, β-olefinic), 7.62 (dd, J=7.8, 1.2 Hz, 1H, H-6), 7.51 (d, J=9, 2H, H-7), 7.39-7.52 (s, 1H, H-4), 7.26 (d, J=15.0 Hz, 1H, α-olefinic), 6.86 (d, J=7.8 Hz, 2H, H-2' and H-6'), 6.53 (d, J=8.4 Hz, 2H, H-3' and H-5'), 6.03 (s, 2H, CH₂O₂), 3.33 (m, J=4.2 Hz, 4H, H-3" and H-4"), 2.01 (m, 4H, H-2" and H-5"); ¹³C-NMR (150 MHz, CDCl₃) δ 188.5, 151.2, 149.6, 148.2, 145.7, 134.0, 130.6, 124.2, 122.3, 115.9, 111.9, 108.5, 107.9, 101.8, 47.7, 25.5; FT-IR: 3100 (C=C—H), 2862 (C—C—H), 1661 (C=O), 1634 (C=C), 1600, 1504 (C=C, aryl), 1110 (C—N) cm⁻¹; Anal. calcd. for C₂₀H₁₉NO₃: C, 74.75; H, 5.96; N, 4.36; Found: C, 74.37; H, 5.98; N, 4.29. LC-MS (+)-ESI (m/z): calculated 321.14, observed 322.2 [M+1]⁺.

Compound 11, (E)-3-(4-morpholinophenyl)-1-(4-(piperazin-1-yl) phenyl) prop-2-en-1-one

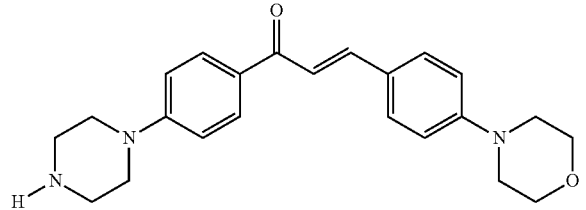 [SMILES: O=C(/C=C/c1ccc(N2CCOCC2)cc1)c1ccc(N2CCNCC2)cc1]

Orange solid; yield=42.4%; m.p.=135.4-136.4° C.; $^1$H-NMR (600 MHz, CDCl$_3$) δ 7.99 (d, J=9 Hz, 2H, H-2 and H-6), 7.75 (d, J=16.2 Hz, 1H, β-olefinic), 7.56 (d, J=8.4, 2H, H-2' and H-6'), 7.41 (d, J=15.0 Hz, 1H, α-olefinic), 6.90 (d, J=9 Hz, 2H, H-3 and H-5), 6.89 (d, J=7.8 Hz, 2H, H-3' and H-5'), 3.85 (m, J=4.8 Hz, 4H, H-2" and H-6"), 3.43 (m, J=5.4 Hz, 4H, H-2" and H-6'''), 3.25 (m, J=4.8 Hz, 4H, H-3" and H-5"), 3.13 (m, J=5.4 Hz, 4H, H-3" and H-5'''), 2.53 (s, 1H, NH); $^{13}$C-NMR (150 MHz, CDCl$_3$) δ 188.4, 152.5, 143.6, 130.6, 130.0, 129.5, 126.3, 118.7, 114.8, 114.0, 113.4, 66.8, 48.2, 47.7, 45.2, 26.3; FT-IR: 3450 (N—H), 3100 (C=C—H), 2833 (C—C—H), 1650 (C=C), 1645 (C=O), 1595, 1513 (C=C, aryl), 1181 (C—N) cm$^{-1}$; LC-MS (+)-ESI (m/z): calculated 377.21, observed 378.5 [M+1]$^+$.

Compound 12, (E)-3-(4-(Bis(2-chloroethyl) amino) phenyl)-1-(2-methoxyphenyl) prop-2-en-1-one

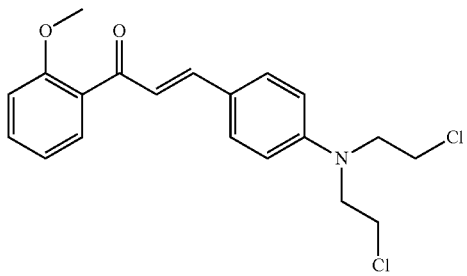 [SMILES: COc1ccccc1C(=O)/C=C/c1ccc(N(CCCl)CCCl)cc1]

Dark orange solid; yield=79.0%; m.p. decomposed; $^1$H-NMR (600 MHz, CDCl$_3$) δ 7.56 (dd, J=7.8, 1.8 Hz, 1H, H-6), 7.52 (d, J=16.2 Hz, 1H, β-olefinic), 7.48 (d, J=9 Hz, 2H, H-2' and H-6'), 7.44 (ddd, J=13.8, 8.4, 1.8 Hz, 1H, H-4), 7.16 (d, J=16.2 Hz, 1H, α-olefinic), 7.02 (m, J=7.8 Hz, 1H, H-5), 7.98 (d, 1H, H-3), 6.66 (d, J=9 Hz, 2H, H-3' and H-5'), 3.87 (s, 3H, OCH$_3$), 3.77 (m, J=7.8 Hz, 4H, H-1" and H-3"), 3.64 (m, J=7.8 Hz, 4H, H-2" and H-4"); $^{13}$C-NMR (150 MHz, CDCl$_3$) δ 193.4, 157.9, 148.0, 143.9, 132.4, 130.7, 130.2, 129.9, 124.5, 123.6, 120.7, 111.8, 111.5, 55.8, 53.4, 40.2; FT-IR: 3100 (C=C—H), 2963 (C—C—H), 1670 (C=C), 1665 (C=O), 1587, 1518 (C=C, aryl), 1162 (C—N) cm$^{-1}$.

Compound 13, (E)-3-(4-(Bis(2-chloroethyl) amino) phenyl)-1-(4-(methylsulfonyl) phenyl) prop-2-en-1-one

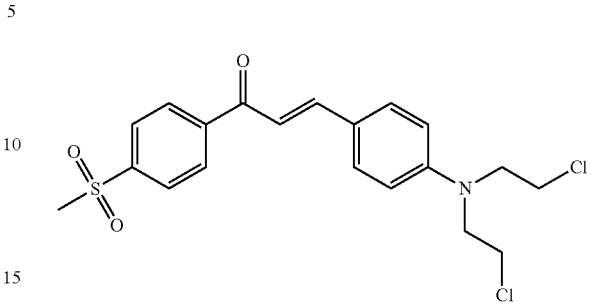

Dark gold solid; yield=84.5%; m.p.=134.8-135.8° C.; $^1$H-NMR (600 MHz, CDCl$_3$) δ 8.12 (d, J=8.4 Hz, 2H, H-2 and H-6), 8.05 (d, J=8.4 Hz, 2H, H-3 and H-5), 7.76 (d, J=15.6 Hz, 1H, β-olefinic), 7.56 (d, J=9, 2H, H-2' and H-6'), 7.27 (d, J=16.2 Hz, 1H, α-olefinic), 6.70 (d, J=7.8 Hz, 2H, H-3' and H-5'), 3.80 (m, J=7.2 Hz, 4H, H-1" and H-3"), 3.66 (m, J=6.6 Hz, 4H, H-2" and H-4"), 3.09 (s, 3H, SO$_2$CH$_3$); $^{13}$C-NMR (150 MHz, CDCl$_3$) δ 189.5, 148.7, 146.9, 144.3, 143.4, 131.2, 129.2, 127.8, 123.8, 117.5, 111.4, 53.5, 44.4, 40.1; FT-IR: 3100 (C=C—H), 2965 (C—C—H), 1687 (C=C), 1649 (C=O), 1575, 1514 (C=C, aryl), 1173 (C—N) cm$^{-1}$; Anal. calcd. for C$_{20}$H$_{21}$C$_{12}$NO$_3$S: 56.34; H, 4.96; N, 3.29; Found: C, 55.06; H, 4.91; N, 3.12. LC-MS (+)-ESI (m/z): calculated 425.06, observed 425.4 [M]$^+$.

Compound 14, (E)-3-(4-(Bis(2-chloroethyl) amino) phenyl)-1-(3-methoxyphenyl) prop-2-en-1-one

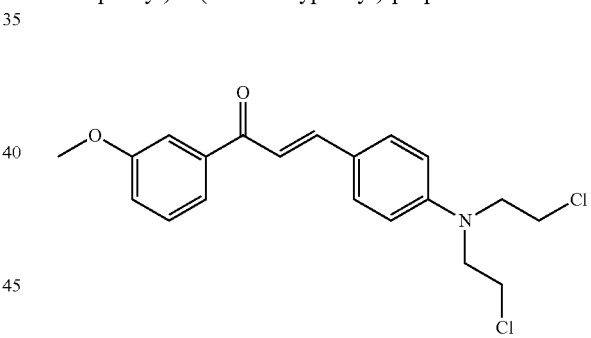

Yellow-brown, hygroscopic, semi-solid; yield=79.3%; m.p. decomposed; $^1$H-NMR (600 MHz, CDCl$_3$) δ 7.74 (d, J=15.6 Hz, 1H, β-olefinic), 7.58 (ddd, 1H, H-6), 7.55 (d, J=9 Hz, 2H, H-2' and H-6'), 7.52 (dd, 1H, H-2), 7.38 (m, J=7.8 Hz, 1H, H-5), 7.32 (d, J=15.0 Hz, 1H, α-olefinic), 7.09 (dd, J=7.8, 1.8 Hz 1H, H-4), 6.58 (d, J=9 Hz, 2H, H-3' and H-5'), 3.86 (s, 3H, OCH$_3$), 3.77 (m, J=6.2 Hz, 4H, H-1" and H-3"), 3.64 (m, J=7.8 Hz, 4H, H2" and H4"); $^{13}$C-NMR (150 MHz, CDCl$_3$) δ 190.4, 159.9, 148.2, 145.0, 140.3, 130.8, 129.6, 124.4, 121.0, 119.0, 118.3, 113.0, 112.0, 55.6, 53.4, 40.3; FT-IR: 3100 (C=C—H), 2960 (C—C—H), 1661 (C=O), 1670 (C=C), 1573, 1515 (C=C, aryl), 1167 (C—N) cm$^{-1}$; Anal. calcd. for C$_{20}$H$_{21}$C$_{12}$NO$_2$: C, 63.50; H, 5.60; N, 3.70; Found: C, 62.46; H, 5.65; N, 3.76. LC-MS (+)-ESI (m/z): calculated 377.09, observed 378.4 [M+1]$^+$.

3.2. Pharmacological Anticancer Screening 3.2.1. Screening on Compound 14

Based on the general screening conducted on the fourteen synthesized chalcones at 10 μM, compounds 13 and 14 had the most optimum activity in terms of their effect on cell morphology and cytotoxicity as compared to the rest of the compounds. Therefore, they were selected for further experimentation for their antitumor effects on breast cancers with a special focus on triple negative breast cancer. They were screened in vitro against a panel of five breast cancer cell lines: invasive triple negative breast cancers (MDA-MB-231 and MDA-MB-468, estrogen positive (MCF-7 and HER2 positive (SK-BR-3 cell lines. The in vitro screening was conducted to determine the mechanisms of action on colony formation and tumor growth, apoptosis, cell cycle, tubulin polymerization, invasion, metastasis, EMT and angiogenesis. Selected experiments were performed on the other compounds to compare potential anticancer activities. In addition, 4-[Bis-(2-chloroethyl) amino] benzaldehyde was screened for its effect on cell migration to predict whether compounds 12, 13 and 14 exerted their effects because of its presence in their structures. The compounds were also tested in vivo in two animal models, the CAM of chicken embryos and Nude mice, to confirm their effects on angiogenesis and tumor growth. They were also investigated for their potential safety in vitro in one immortalized normal breast cancer (HNME-E6/NE7) cell line and in vivo for their survival effect on the two animal models used. Colchicine and paclitaxel are two conventional anticancer medications that were included as positive controls in selected experiments. Molecular docking studies were performed on some molecular targets to confirm the compounds activities in silico. All experiments were done in triplicates and were repeated three times unless otherwise specified.

3.2.1.1. Effects on Cell Morphology

The effect of compounds 13 and 14 on triple negative (MDA-MB-231 and MDA-MB-468) as well as estrogen positive (MCF-7) cells was compared at two time points, 24 hours and 48 hours post treatment, at a concentration of 10 μM. In addition, the effect of the compounds on normal cell morphology was studied on HNME (E6/E7) cells.

Untreated and DMSO treated MDA-MB-468, MDA-MB-231 and MCF-7 cells had good morphology and were in their regular shapes at 24 and 48 hours (FIG. 3.3, FIG. 3.4 and FIG. 3.5, respectively). For instance, MDA-MB-231, cells looked more fibroblastic and elongated in shape with loose interactions between the cells indicating that control cells were healthy and in their usual morphology. Compound 13 at 10 μM caused MDA-MB-231 cells to look more spherical in shape and to lose their mesenchymal fibroblastic property. Cells became more adherent to each other with cohesive interaction at 24 hours post treatment (FIG. 3.3A). This effect was less clear at 48 hours as cells started to die and proliferation decreased. Mainly single circular cells were obvious at 48 hours. On the other hand, compound 14 did not induce a significant difference in MDA-MB-231 cells at 24 hours unlike compound 13. However, at 48 hours there was a change in cell shape as compared to the controls (FIG. 3.3B). Generally, at 48 hours there were many floating live cells in control cells due to their ability of proliferation and invasion. Therefore, the differences were not that obvious between treated and untreated cells at 24 hours.

On the other hand, MDA-MB-468 were more in contact and had good integrity in the controls. However, both compounds caused an obvious change in cell shape at 24 hours. Cells became larger in shape and looked more epithelial. Remarkably, less colonies were noticed with treated cells as they were growing as singlets and lost the contact colonies character seen in the untreated cells (FIG. 3.4A). This effect became more obvious at 48 hours with higher reduction in proliferation rate as compared to the controls.

In MCF-7 cells, microscopic examination revealed some loss of outer membranes in treated cells at 48 hours of treatment with compounds 13 and 14 (FIG. 3.5B). Both compounds caused changes in cell integrity and shape at 48 hours mainly and less changes at 24 hours. At 48 hours, cells started growing as singlets with less proliferative rate and more cell death. In particular, compound 13 triggered cells to become larger in shape, while compound 14 induced cell shrinkage. As with MDA-MB-468, cells lost colony formation ability seen with the controls and were growing as discrete single cells.

3.2.1.2. $IC_{50}$, $LD_{50}$ and Selectivity Determination

The ultimate goal when designing a drug is to have an excellent efficacy and lower toxicity. To determine if compounds 13 and 14 can serve as potential optimal therapeutic options with good efficacy and safety profiles, the $IC_{50}$ and $LD_{50}$ were calculated based on 6-8 different concentrations tested on three breast cancer cell lines and one immortalized human normal mammary epithelial cell immortalized with E6/E7 (HNME-E6/E7). The selective index was then estimated based on the $IC_{50}$ values of the two compounds on breast cancer cell lines as compared to their $LD_{50}$ on the normal cell line calculated at 48 hours. As shown in Table 3.1, both compounds showed potent activities on cancer cells with compound 14 being more potent than compound 13 in all breast cancer cell lines. On the other hand, both compounds exhibited greater selectivity towards cancerous cells as compared to normal ones. Compound 13 selectivity was approximately similar between different breast cancer cell lines (~3). However, compound 14 was more selective towards MCF-7 (>5) as compared to MDA-MB-231 and MDA-MB-468 (3.2 and 2.36, respectively). Moreover, a morphology study was conducted on immortalized HNME-E6/E7 to observe any potential changes after 48 hours of treatment with compounds 13 and 14 at 5 μM. Interestingly, both compounds, 13 and 14, induced morphological changes to immortalized HNME-E6/E7 cells causing them to become larger in size and gain back their normal epithelial cell morphology (FIG. 3.6).

TABLE 3.1

$IC_{50}$, $LD_{50}$, and selective index of compounds 13 and 14

|  | 13 | 14 |
|---|---|---|
| MDA-MB-231(μM) | 9.67 ± 0.68 | 6.30 ± 0.78 |
| MDA-MB-468 (μM) | 9.29 ± 0.68 | 8.73 ± 0.67 |
| MCF-7 (μM) | 8.95 ± 1.46 | 3.96 ± 1.87 |
| BT-474 (μM) | NA | 9.22 ± 0.78 |
| HNME-E6/E7 (μM) | 32.32 ± 3.93 | 20.67 ± 1.50 |
| SI of HNME/MDA-231 | 3.34 | 3.20 |
| SI of HNME/MDA-468 | 3.48 | 2.36 |
| SI of HNME/MCF-7 | 3.61 | 5.22 |
| SI of HNME/BT-474 | NA | 2.24 |

NA = Not Applicable; SI: selective index; each $LD_{50}/EC_{50}$ was calculated based on 5-8 different concentrations following 48 hours of treatment; Results are expressed as Mean ± SEM (n = 3 x 3) and were computed using non-linear regression test. Selective index was calculated based on the ratio of $LD_{50}$ on HNME-E6/E7 relative to the $IC_{50}$ of the different breast cancer cell lines 3.2.1.3. Effects on Carcinogenesis and Colony Formation Carcinogenesis is characterized by the ability of transformed cells to grow in an anchorage-independent manner. In this sort of growth, cells would lose their cell cycle control and acquire the ability to grow in colonies independent of a solid surface and proliferate without adhesion to the extracellular matrix proteins (ECM). Based on the microscopic examination on MDA-MB-231, MDA-MB-468 and MCF-7, it was noticed that cells had less proliferative rate when treated with compounds 13 and 14 and were unusually growing as singlets in MDA-MB-468 and MCF-7 suggesting that the compounds might be playing a role in preventing malignant transformations. Therefore, it was hypothesized that the new compounds may play a role in preventing cancer colony formation and proliferation.

Soft agar colony formation assay was used to assess this hypothesis. It is a robust and validated in vitro test to assess the ability of cells to form colonies and is comparable to the in vivo test conducted in nude mice. Therefore, it was chosen to study the effect of chalcone derivatives 13 and 14 on breast cancer colony formation. As presented in FIG. 3.7, FIG. 3.8 and FIG. 3.9, there was almost 100% less colonies in all investigated breast cancer cell lines treated with compounds 13 and 14 at 5 and 10 μM as compared to untreated ones (p-value <0.0001). This confirmed the hypothesis that the two compounds play a role in preventing tumor growth and malignant transformations. Colchicine and paclitaxel were used as positive controls to compare their effects to compounds 13 and 14. As seen in all cell lines, both drugs had significantly inhibited the ability of cells to form colonies as compared to untreated cells. However, compounds 13 and 14 had better effects on MDA-MB-231 as compared to colchicine and paclitaxel (P-value 0.0014 and 0.0012, respectively) and better effects on MCF-7 as compared to colchicine (P-value 0.0009).

3.2.1.4. Effects of Compound 14 on Cancer Cells Apoptosis

As noticed with previously conducted experiments, there was strong antiproliferative effects seen with compound 14. In addition, morphological investigations showed some membrane loss and high numbers of apoptotic bodies and cell death. These findings strongly support the hypothesis that the compounds are inducing apoptosis. Thus, Annexin V apoptosis test was conducted at 24 h and 48 h on a representative TNBC cell line, MDA-MB-468, to investigate the levels of apoptosis for compound 14 (FIG. 3.10B). During the early stages of apoptosis, phospholipid phosphatidylserine (PS) is known for its translocation from the inner to the outer plasma membrane of the cell, thus subjecting PS to the external cellular environment where Annexin V can strongly bind. This externalization of PS occurs in the earlier stages of apoptosis only; therefore, PE Annexin V can identify apoptosis at this stage alone, but not based on nuclear changes such as DNA fragmentation. The results showed that early and late apoptosis induced by compound 14 were time dependent. In addition, the rate of apoptosis was significantly higher than that noticed with the DMSO vehicle controls in triple negative breast cancer cells at 48 hours (28.00% vs 4.15%; respectively). To confirm the role of compound 14 in apoptosis, the expression of the pro-apoptotic BAX and pre-apoptotic bcl-2 proteins was studied following 48 h of treatment with 5 and 10 μM of the compound and were compared to DMSO as a negative control and colchicine as a positive control FIG. 3.11 and FIG. 3.12). As seen, the western blot analysis releveled a positive increase in BAX/bcl-2 ratio in the cells treated with compound 14 as compared to the both controls.

3.2.1.5. Effects on Cancer Cells Cycle Progression

To confirm compounds 13 and 14 activities in cell proliferation and cell cycle progression, a cell cycle study was conducted on three cell lines (MDA-MB-231, MDA-MB-468 and MCF-7) (FIG. 3.13, FIG. 3.14 and FIG. 3.15). The DNA content in the different cell cycle phases was quantified using flow cytometer. The first peak denotes cells arrested at G0/G1 phase, the second represents cells arrested at the S phase, and the third peak represents DNA content of cells arrested in the G2/M phase. As shown, in MDA-MB-231 and MDA-MB-468 invasive cell lines, compound 13 induced a statistically significant cell cycle arrest at the S phase after 48 hours of treatment (28.7±1.87% and 46.8±5.39%, respectively; P-values 0.0002 and 0.0165). On the other hand, compound 14 arrested the cells at the G2/M phase in MDA-MB-231 and MD-MB-468 cells (47.27±7.869% and 66.45±4.25%, respectively; P-values 0.0006 and 0.0009) with an effect similar to colchicine and paclitaxel. Interestingly, these effects were mainly noticed in the invasive cell lines but not in the noninvasive, MCF-7, cells. To investigate whether compounds 13 and 14 exerted their cell cycle activities due to the presence of nitrogen mustard group in their chemical structures, other synthetic chalcone derivatives (2, 5, and 9) with no nitrogen mustard were tested for the effect on cell cycle on MDA-MB-231 triple negative breast cancer cell line. As can be seen in FIG. 3.16, no major cell cycle shifts were noted with these chalone derivatives, except for compound 2 which induced a slight S phase arrest. This compound has a 4-(methylsulfonyl) substitution at ring A, similar to compound 13.

3.2.1.6. Effects on Cancer Cells Invasion

Based on the previous results, the effects of the compounds were more predominant in invasive breast cancer cell lines. Therefore, we hypothesized that the compounds may play a significant role in inhibiting cell invasion and metastasis. Hence, we investigated the role of compounds 13 and 14 on cell invasion using Matrigel invasion assay on MDA-MB-231 (FIG. 3.17), MDA-MB-468 (FIG. 3.18) and MCF-7 (FIG. 3.19) cells. This test allows for thorough examination of cells migration and invasion ability by testing their capability of invading through physical barrier toward a chemoattractant, such as serum. As shown, no differences were noted between untreated and DMSO treated controls indicating DMSO does not have a role in compounds 13 and 14 anti-invasion activities. On the other hand, both compounds had significantly reduced cancer cells invasion in MDA-MB-231 (79.57% and 82.54% reductions, respectively; P-value 0.0181) and MDA-MB-468 (48.45% and 59.28% reductions, respectively; P-value 0.0087) TNBCs cells as compared to DMSO control. On the other hand, the findings on the noninvasive cell line, MCF-7, showed that both compounds significantly inhibited cell invasion and motility; particularly, with a close effect (45.70% and 57.26% reductions, respectively; P-value 0.0161) to that noticed on MDA-MB-468.

3.2.1.7. Effects on Cancer Cells Migration

The effects of compounds 13 and 14 were also investigated on cell migration in MDA-MB-231 cells and were compared with the rest of synthesized chalcone derivatives in addition to colchicine and paclitaxel using wound healing assay (FIG. 3.20). Compounds 5, 8, 10, 12-14 caused the highest inhibition in cell migration as compared to the rest of the compounds (Table 3.2). Therefore, they were tested on different concentrations and their $IC_{50}$ values were calculated and reported in Table 3.3. Compounds 12 and 14 were the most potent among the rest ($IC_{50}$=1.998±0.1885 μM and 2.857±0.1969 μM, respectively). The effect of compound 14 at different concentrations is presented at FIG. 3.21. Since all of the compounds bearing the nitrogen mustered functional group, 12-14, caused a significant inhibition in cell motility, we hypothesized that nitrogen mustard can promote this effect. To confirm this, we tested the anti-migration effect of 4-[Bis-(2-chloroethyl) amino] benzaldehyde, which contains nitrogen mustard and is part of compounds 12-14 chemical structures. Interestingly, the effect of compounds 12-14 was statistically significant from the effect noticed with 4-[Bis-(2-chloroethyl) amino] benzaldehyde in MDA-MB-231 cells. For instance, compound 14 inhibited cell migration by 67.89±0.17% compared to 29.5±1.95% inhibition with 4-[Bis-(2-chloroethyl) amino] benzaldehyde (P-value <0.0001). To investigate whether compound 14 effects on migration are limited to triple negative breast cancer, its effect was studied on estrogen positive (MCF-7) and HER2 positive (SK-BR-2) cells at different concentrations (FIG. 3.22 and FIG. 3.23; respectively) and its $IC_{50}$ values were calculated and reported (Table 3.3). The results showed a potent inhibition, very close to the effect reported on MDA-MB-231, on both cell lines, MCF-7 and SK-BR-3 ($IC_{50}$=2.44±0.39 µM and 2.79=0.45 µM, respectively).

TABLE 3.2

Effects of compounds 1-14 on MDA-MB-231 cell migration

| Compounds | % migration | P-value |
|---|---|---|
| Control | 100 | |
| 1 | 74.65 ± 5.8 | 0.0094 |
| 2 | 67.33 ± 53.85 | 0.0006 |
| 3 | 65.66 ± 52.35 | 0.0003 |
| 4 | 70.66 ± 55.85 | 0.0020 |
| 5 | 64.27 ± 3.32 | 0.0002 |
| 6 | 69.53 ± 3.92 | 0.0013 |
| 7 | 71.8 ± 0.06 | 0.0031 |
| 8 | 48.67 ± 2.85 | <0.0001 |
| 9 | 74.98 ± 0.86 | 0.0106 |
| 10 | 53.49 ± 5.98 | <0.0001 |
| 11 | 75.08 ± 0.86 | 0.0111 |
| 12 | 32.8 ± 0.68 | <0.0001 |
| 13 | 59.53 ± 2.75 | <0.0001 |
| 14 | 32.11 ± 0.17 | <0.0001 |
| Colchicine | 47.45 ± 0.25 | <0.0001 |
| Paclitaxel | 39.33 ± 5.16 | <0.0001 |
| NM | 70.53 ± 1.95 | 0.0019 |

NM = Nitrogen mustard; Results were expressed as Mean ± SEM (N = 2 × 2) collected at 24 hours post treatment; One-way ANOVA followed by Tukey's post-hoc test were used to compare the treatment groups

TABLE 3.3

Migratory $IC_{50}$ of the most effective compounds against cell migration

| | MDA-MB-231 (µM) | MCF-7 (µM) | SK-BR-3 (µM) |
|---|---|---|---|
| 5 | 6.14 ± 0.62 | NA | NA |
| 8 | 3 ± 0.46 | NA | NA |
| 10 | 4.80 ± 0.72 | NA | NA |
| 12 | 1.99 ± 0.19 | NA | NA |
| 13 | 5.71 ± 0.57 | NA | NA |
| 14 | 2.86 ± 0.20 | 2.44 ± 0.39 | 2.79 ± 0.45 |
| Colchicine | 2.75 ± 0.20 | NA | NA |
| Paclitaxel | 2.01 ± 0.22 | NA | NA |

NA = Not Applicable; $IC_{50}$ values were calculated based on 5 different concentrations following 24 hours of treatment using non-linear regression test; Results were expressed as Mean ± SEM and were based on two independent experiments for MDA-MB-231 and three independent experiments for MCF-7 and SK-BR-3.

3.2.1.8. Effects of Compound 14 on EMT

Based on the previous investigations, compound 14 induced positive effects on cell invasion and migration and was noticed to induce morphological changes making MDA-MB-231 cells look more adherent and less mesenchymal in shape. Thus, we hypothesized that compound 14 is inducing possible reversal of the EMT process which is linked to cancer invasiveness and metastasis. To this end, the protein expressions of five different EMT biomarkers, E-cadherin, pan-cadherin, total and phosphorylated 3-catenin and FAK were studied on MDA-MB-231 triple negative cell lines (FIG. 3. 24) and were compared with MCF-7 non-triple negative cell line (FIG. 3. 25). As seen, there was a concentration dependent upregulation of the epithelial marker E-cadherin on both cell lines. On the other hand, the expression of pan-cadherin was upregulated by compound 14 in a concentration dependent manner on both cell lines. No significant changes were observed with compound 14 on the expression of 3-catenin and its phosphorylated form unlike colchicine which had upregulated phospho-3-catenin. Furthermore, Focal adhesion kinase (FAK) expression was studied on MDA-MB-231 cell line and was shown to be downregulated by compound 14 in an effect comparable to colchicine (FIG. 3. 24).

3.2.1.9. Effects of Compound 14 on Tubulin Polymerization Dynamics

Tubulin is a critical protein involved in cellular trafficking, motility and cell division. Our previous findings on cell motility and cell cycle progression suggests that compound 14 might be targeting tubulin. Particularly, we hypothesized that it might be binding to the colchicine binding site of tubulin, because several chalcone derivatives were reported to act on tubulin polymerization through binding to this binding site. To justify this hypothesis, a computer aided molecular docking study was conducted to predict the binding affinity and binding mode of compound 14 on colchicine binding site located at the b-tubulin subunit (PDB code: 5LYJ). The compound showed good fitting into the binding pocket of the colchicine binding site with hydrogen bonding between the carbonyl and ASP251 amino acid residue (FIG. 3.26A). Virtual binding score of compounds 1-14 was calculated and compared to the binding score of colchicine and combretastatin as positive controls. Interestingly, all compounds resulted in very low binding score comparable to two positive controls, colchicine and combretastatin, indicating potentially high binding affinities. However, these are only virtual estimations and do not necessary correlates with reality. Therefore, tubulin free assay was conducted to confirm these findings. As seen in FIG. 3.26B, compound 14 acted in a mechanism opposite to paclitaxel which is known for enhancing tubulin polymerization. The effect was comparable to tubulin desterilizing agent, colchicine, confirming the molecular docking findings.

TABLE 3.4

Glide bind scores of compounds 1-14 (PCB code: 5LYJ)

| Compounds | Binding Score |
|---|---|
| 1 | −7.46 |
| 2 | −7.56 |
| 3 | −7.82 |
| 4 | −8.81 |
| 5 | −8.72 |
| 6 | −7.21 |
| 7 | −8.23 |
| 8 | −9.106 |
| 9 | −8.46 |
| 10 | −6.85 |
| 11 | −7.79 |
| 12 | −8.79 |
| 13 | −8.05 |
| 14 | −8.90 |
| Colchicine | −8.00 |
| Combretastatin | −9.21 |

3.2.1.10. Effects on Angiogenesis Using the CAM Model

Several studies had demonstrated the substantial role of angiogenesis in breast cancer proliferation, growth and metastasis. In TNBC, microvascular density is extremely high making breast tumors larger, more invasive and generally complicating disease treatment. On the other hand, several chalcone derivatives were reported to exert antiangiogenic effects. Therefore, we hypothesized that part of the seen effects of our compounds on inhibiting cancer proliferation, growth and metastasis could be linked to an effect on angiogenesis. To investigate this, CAM of chicken embryos was used to study the effect of compound 14 on angiogenesis and whether they can reduce blood vessels on the CAM of the embryos. The effects of compounds 5 and 13 were also investigated to confirm the hypothesis that chalcones can serve as antiangiogenic targeted medications.

The CAM is a well-established and widely used model to study the effects on angiogenesis and blood vessels formation, therefore, it was used in this study. Four days chicken embryos were treated with compounds 5, 13 and 14 and followed daily until embryonic day 8. As shown on FIG. 3.27A, all compounds had significantly diminished the amount of blood vessels. Particularly, they reduced smaller blood vessels formation and branching. Chicken embryos treated with compounds 13 and 14 were scarified by the end of the experiments and were noticed to have less blood vessel distribution as compared to the DMSO treated control (FIG. 3.27B). The numbers of blood vessel branches under the location of the treatment, the cover slip, were quantified manually and were compared to the branches at the untreated areas (FIG. 3.27C). The results show that all chalcone derivatives, 5, 13 and 14, had effectively reduced blood vessels development as compared to the control (68.49±4.42%, 55.6±6.04% and 60.20±8.47% inhibition, respectively; P-value <0.0001).

3.2.1.11. Effects of Compound 14 Tumor on Growth in Nude Mice

Compared to all synthesized compounds, compound 14 exerted the most promising anticancer effects suggesting its potential to serve as an excellent lead compound for further drug development as an anti-TNBC therapy. To support this, an in vivo study was conducted using nude mice xenografted with TNBC, MDA-MB-231, cells. First, compound 14 was tested for two weeks at a concentration of 10 mg/kg administered to the mice (n=5) intraperitoneally to determine if mice can tolerate the dose and that it is safe for use. Clinical observations did not show any changes in the mice food intake, weights, or shape. Therefore, we determined that the compound is safe for use and can be tolerated by animals. Following, subcutaneous inoculation of MDA-MB-231 cells was performed into the second mammary gland fat pad of nude mice and the tumor was allowed to develop and localize for 48 hours. The treatment group (n=5) was administered with compound 14 (10 mg/kg/day, i.p., three time per week), while the control mice were administered with an equivalent volume of placebo.

The tumor in the treated group started to grow on day 24, changes in tumor volume were then monitored and recoded on each treatment day (FIG. 3.28C). The experiment stopped at day 45 and the groups were compared. The results revealed 46.41% inhibition in tumor growth by compound 14 as compared to the placebo (FIG. 3.28B). As can be seen, there was a significant difference between the treated and control mice in terms of tumor weight (0.88±0.71 gm versus 1.58±0.283 gm, respectively; P-value 0.0437) and tumor volume (1350±1350 mm$^3$ versus 487.26±522.597 mm$^3$, respectively; P-value 0.0437). Compound 14 was also shown to delay tumor growth as can be noticed (FIG. 3.28D). Concerning compound 14 toxicity, the obtained results revealed no notable clinical toxicity to treated animals. Moreover, the administration of compound 14 into the systemic circulation did not affect the mice health nor it had induced any changes to the mice weight (FIG. 3.28E). Furthermore, the survival rate of the mice was 100% during the 45 days FIG. 3.28F). These findings suggest that compound 14 is potentially safe for use as an anticancer drug and that it is more selective towards cancer, but not normal cells, which confirms the in vitro selectivity results.

All publications and patent applications cited in this specification are herein incorporated by reference as if each individual publication or patent application were specifically and individually indicated to be incorporated by reference. While the claimed subject matter has been described in terms of various embodiments, the skilled artisan will appreciate that various modifications, substitutions, omissions, and changes may be made without departing from the spirit thereof. Accordingly, it is intended that the scope of the subject matter is limited solely by the scope of the following claims, including equivalents thereof.

LIST OF REFERENCES

Al Moustafa A E, Foulkes W D, Benlimame N, Wong A, Yen L, Bergeron J, et al., "E6/E7 proteins of HPV type 16 and ErbB-2 cooperate to induce neoplastic transformation of primary normal oral epithelial cells." Oncogene. 2004; 23(2):350-8.

Elmore S., "Apoptosis: a review of programmed cell death." Toxicologic pathology. 2007; 35(4):495-516.

Chan A, Reiter R, Wiese S, Fertig G, Gold R. "Plasma membrane phospholipid asymmetry precedes DNA fragmentation in different apoptotic cell models." Histochem Cell Biol. 1998; 110(6):553-8.

Nagata S. "Apoptotic DNA fragmentation." Exp Cell Res. 2000; 256(1):12-8.

Lindamulage I K, Vu H Y, Karthikeyan C, Knockleby J, Lee Y F, Trivedi P, et al. "Novel quinolone chalcones targeting colchicine-binding pocket kill multidrug-resistant cancer cells by inhibiting tubulin activity and MRP1 function." Scientific reports. 2017; 7(1):1029

Martel-Frachet V, Keramidas M, Nurisso A, DeBonis S, Rome C, Coll J L, et al. "IPP51, a chalcone acting as a microtubule inhibitor with in vivo antitumor activity against bladder carcinoma." Oncotarget. 2015; 6(16): 14669-86.

Yang J, Yan W, Yu Y, Wang Y, Yang T, Xue L, et al. "The compound millepachine and its derivatives inhibit tubulin polymerization by irreversibly binding to the colchicine-binding site in beta-tubulin." J Biol Chem. 2018; 293(24):9461-72.

Boumendjel A, McLeer-Florin A, Champelovier P, Allegro D, Muhammad D, Souard F, et al. "A novel chalcone derivative which acts as a microtubule depolymerising agent and an inhibitor of P-gp and BCRP in in-vitro and in-vivo glioblastoma models." BMC Cancer. 2009; 9:242.

Wang Y T, Qin Y J, Yang N, Zhang Y L, Liu C H, Zhu H L. "Synthesis, biological evaluation, and molecular docking studies of novel 1-benzene acyl-2-(1-methyl-indol-3-yl)-benzimidazole derivatives as potential tubulin."

Andrade S S, Sumikawa J T, Castro E D, Batista F P, Paredes-Gamero E, Oliveira L C, et al. "Interface between breast cancer cells and the tumor microenvironment using platelet-rich plasma to promote tumor angiogenesis—influence of platelets and fibrin bundles on the behavior of breast tumor cells." Oncotarget. 2017; 8(10):16851-74.

Ramanathan R, Olex A L, Dozmorov M, Bear H D, Fernandez L J, Takabe K. "Angiopoietin pathway gene expression associated with poor breast cancer survival. Breast cancer research and treatment."

Tsutsui S, Kume M, Era S. "Prognostic value of microvessel density in invasive ductal carcinoma of the breast." Breast cancer (Tokyo, Japan). 2003; 10(4):312-9.

Oikawa T, Hirotani K, Nakamura O, Shudo K, Hiragun A, Iwaguchi T. "A highly potent antiangiogenic activity of retinoids." Cancer letters. 1989; 48(2):157-62.

Mohamed M F, Mohamed M S, Fathi M M, Shouman S A, Abdelhamid I A. "Chalcones incorporated pyrazole ring inhibit proliferation, cell cycle progression, angiogenesis and induce apoptosis of MCF7 cell line." Anticancer Agents Med Chem. 2014; 14(9):1282-92.

Zhu X F, Xie B F, Zhou J M, Feng G K, Liu Z C, Wei X Y, et al. "Blockade of vascular endothelial growth factor receptor signal pathway and antitumor activity of ON-III (2',4'-dihydroxy-6'-methoxy-3',5'-dimethylchalcone), a component from Chinese herbal medicine." Mol Pharmacol. 2005; 67(5):1444-50.

Wang Z, Wang N, Han S, Wang D, Mo S, Yu L, et al. "Dietary compound isoliquiritigenin inhibits breast cancer neoangiogenesis via VEGF/VEGFR-2 signaling pathway." PLoS One. 2013; 8(7):e68566.

What is claimed is:

1. A compound of formula I:

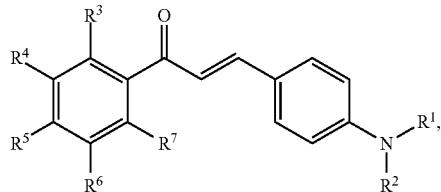

or a pharmaceutically acceptable salt or solvate thereof, wherein
$R^1$ and $R^2$ are each independently haloalkyl;
$R^4$ is selected from chloro, methylsulfonyl, methylthio, methoxy, piperazinyl, pyrrolidyl, morpholinyl, and piperidyl; and
$R^3$, $R^5$, $R^6$, and $R^7$ are each hydrogen.

2. The compound of claim 1, wherein $R^4$ is methoxy.

3. A compound selected from the following:

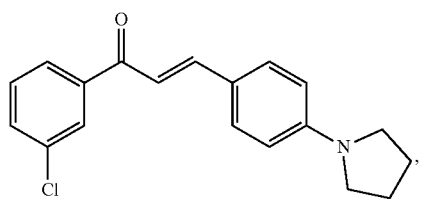

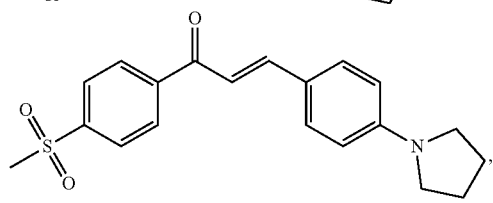

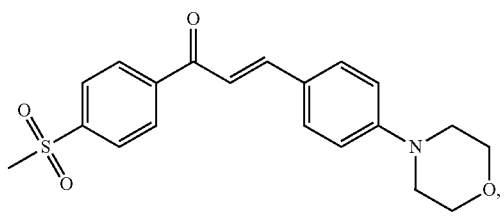

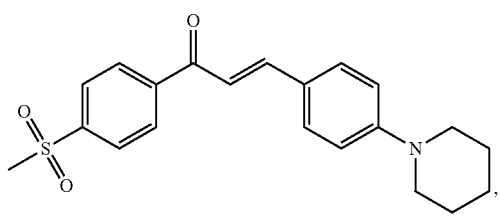

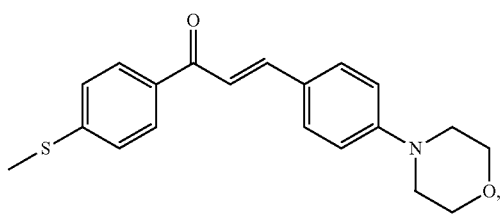

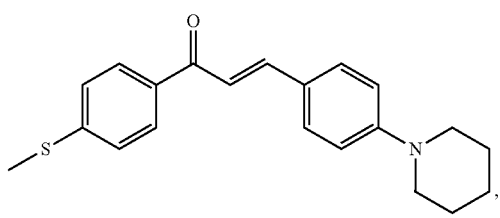

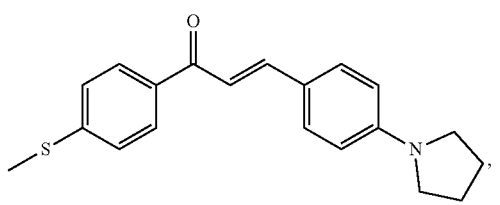

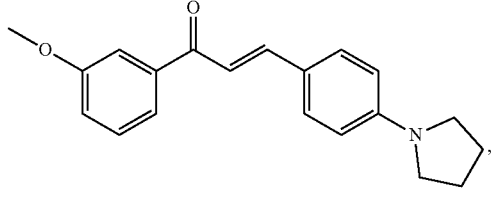

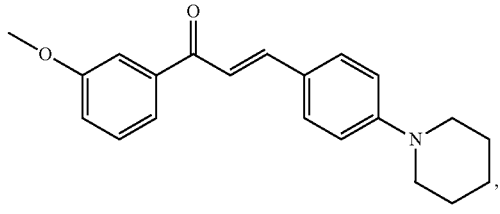

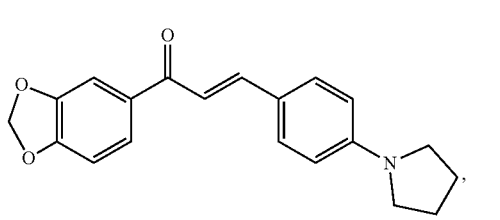

-continued

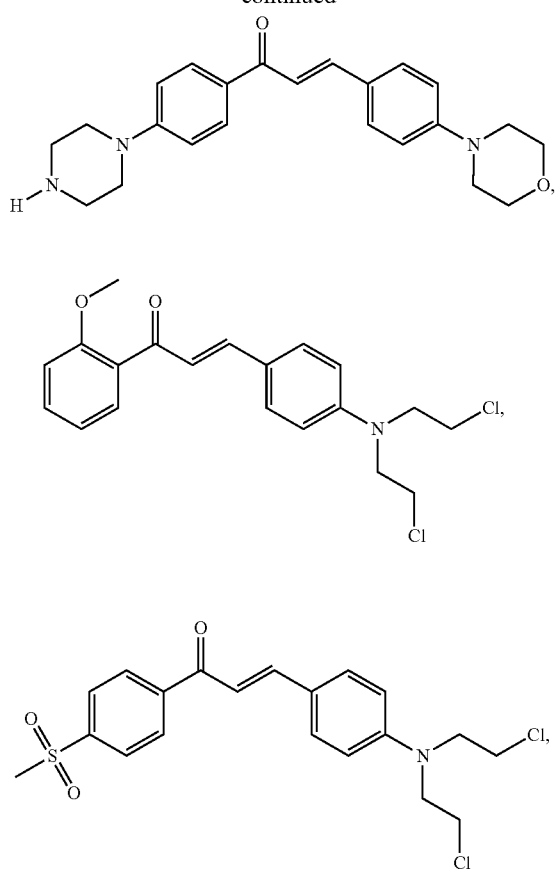

and

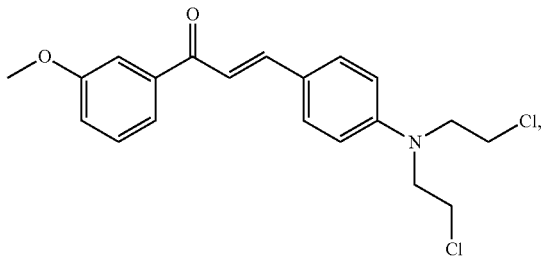 [SMILES: COc1cccc(C(=O)/C=C/c2ccc(N(CCCl)CCCl)cc2)c1]

or a pharmaceutically acceptable salt or solvate thereof.

4. The compound of claim 3, of formula:

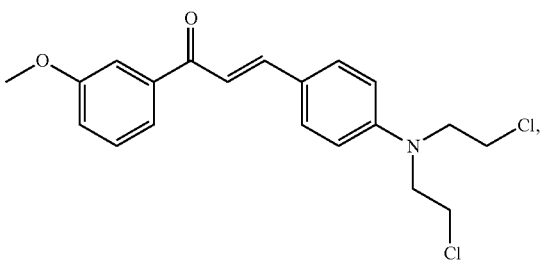 [SMILES: COc1cccc(C(=O)/C=C/c2ccc(N(CCCl)CCCl)cc2)c1]

or a pharmaceutically acceptable salt or solvate thereof.

5. A composition comprising the compound of claim 1.

6. A pharmaceutical composition comprising the compound of claim 3 and a pharmaceutically acceptable carrier and/or excipient.

7. A method of treating cancer in a subject in need thereof, comprising administering an effective amount of the compound of claim 1, to the subject.

8. A method of treating cancer in a subject in need thereof, comprising administering an effective amount of the composition of claim 5, to the subject.

9. A method of treating cancer in a subject in need thereof, comprising administering a pharmaceutically effective amount of the pharmaceutical composition of claim 6, to the subject.

10. The method of claim 7, wherein the cancer is breast cancer or triple negative breast cancer.

11. The method of claim 8, wherein the cancer is breast cancer or triple negative breast cancer.

12. The compound of claim 3, of formula:

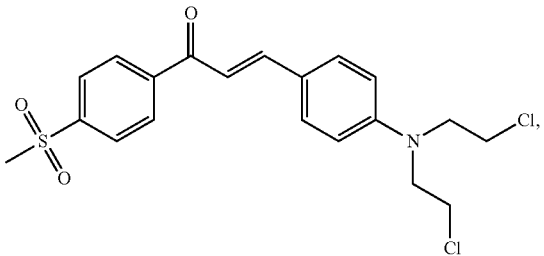 [SMILES: CS(=O)(=O)c1ccc(C(=O)/C=C/c2ccc(N(CCCl)CCCl)cc2)cc1]

or a pharmaceutically acceptable salt or solvate thereof.

* * * * *